(12) United States Patent
Goldsmith et al.

(10) Patent No.: US 8,101,610 B2
(45) Date of Patent: Jan. 24, 2012

(54) BISAMIDE INHIBITORS OF HEDGEHOG SIGNALING

(75) Inventors: Richard A. Goldsmith, Belmont, CA (US); Daniel P. Sutherlin, South San Francisco, CA (US); Kirk D. Robarge, San Francisco, CA (US); Alan G. Olivero, Half Moon Bay, CA (US)

(73) Assignees: Genentech, Inc., South San Francisco, CA (US); Curis Inc., Lexington, MA (US)

( * ) Notice: Subject to any disclaimer, the term of this patent is extended or adjusted under 35 U.S.C. 154(b) by 410 days.

(21) Appl. No.: 12/093,530

(22) PCT Filed: Nov. 14, 2006

(86) PCT No.: PCT/US2006/044240
§ 371 (c)(1),
(2), (4) Date: May 13, 2008

(87) PCT Pub. No.: WO2007/059157
PCT Pub. Date: May 24, 2007

(65) Prior Publication Data
US 2008/0269215 A1    Oct. 30, 2008

Related U.S. Application Data

(60) Provisional application No. 60/735,861, filed on Nov. 14, 2005.

(51) Int. Cl.
| | |
|---|---|
| *A61K 31/505* | (2006.01) |
| *A61K 31/4965* | (2006.01) |
| *A61K 31/4196* | (2006.01) |
| *A61K 31/4164* | (2006.01) |
| *C07D 213/81* | (2006.01) |

(52) U.S. Cl. .................. 514/247; 514/252.12; 514/256; 514/383; 514/396; 546/323

(58) Field of Classification Search .............. 514/247, 514/252, 12, 256, 383, 396
See application file for complete search history.

(56) References Cited

U.S. PATENT DOCUMENTS

| | | | |
|---|---|---|---|
| 7,342,037 | B2 | 3/2008 | Flynn et al. |
| 7,351,834 | B1 | 4/2008 | Riedl et al. |
| 2006/0025485 | A1 | 2/2006 | Holen et al. |
| 2007/0232661 | A1 | 10/2007 | Beachy et al. |

FOREIGN PATENT DOCUMENTS

| | | | |
|---|---|---|---|
| WO | WO 9822103 A | | 5/1998 |
| WO | 99/15164 | * | 4/1999 |
| WO | 99/59960 | * | 11/1999 |
| WO | WO 00/07991 | * | 2/2000 |
| WO | WO 0018738 A | | 4/2000 |
| WO | WO 2005/033288 A2 | * | 4/2005 |
| WO | WO 2005033288 A2 | | 4/2005 |
| WO | WO 2006007520 A | | 1/2006 |
| WO | WO 2006024836 A | | 3/2006 |
| WO | WO 2006040568 A | | 4/2006 |

OTHER PUBLICATIONS

Vippagunta, S.R. Adv. Drug Del. Rev., vol. 48, (2001), pp. 3-26.*
Sausville et al. Cancer Research, 2006, vol. 66, pp. 3351-3354.*
Johnson et al. British J. Of Cancer, 2001, 84(10):1424-1431.*

* cited by examiner

*Primary Examiner* — James D Anderson
(74) *Attorney, Agent, or Firm* — Millen, White, Zelano & Branigan, P.C.

(57) ABSTRACT

The invention provides inhibitors of hedgehog signaling that are useful as a therapeutic agents for treating malignancies where the compounds have the general formula I:

I wherein ring A, ring B, $R_1$, $R_2$, $R_3$, $R_4$, $R_5$, m and n are as defined herein.

20 Claims, No Drawings

BISAMIDE INHIBITORS OF HEDGEHOG SIGNALING

This application claims the benefit of the filing date of U.S. Provisional Application Ser. No. 60/735,861 filed Nov. 14, 2005.

FIELD OF THE INVENTION

The present invention relates to organic compounds useful for therapy and/or prophylaxis in a mammal, in particular to compounds that inhibit the hedgehog signaling pathway and are useful in the treatment of hyperproliferative diseases and angiogenesis mediated diseases.

BACKGROUND OF THE INVENTION

Hedgehog (Hh) protein was first identified in *Drosophila melanogaster* as a segment-polarity gene involved in embryo patterning (Nusslein-Volhard et al., Roux. Arch. Dev. Biol. 193: 267-282 (1984)). Three orthologs of *Drosophila* hedgehog (Sonic, Desert and Indian) were later identified to occur in all vertebrates including fish, birds and mammals. Desert hedgehog (DHh) is expressed principally in the testes, both in mouse embryonic development and in the adult rodent and human; Indian hedgehog (IHh) is involved in bone development during embryogenesis and in bone formation in the adult; and, Sonic hedgehog (SHh) is expressed at high levels in the notochord and floor plate of developing vertebrate embryos. In vitro explant assays as well as ectopic expression of SHh in transgenic animals have shown that SHh plays a key role in neuronal tube patterning (Echelard et al., supra.; Ericson et al., Cell 81: 747-56 (1995); Marti et al., Nature 375: 322-5 (1995); Krauss et al., Cell 75, 1432-44 (1993); Riddle et al., Cell 75: 1401-16 (1993); Roelink et al, Cell 81:445-55 (1995); Hynes et al., Neuron 19: 15-26 (1997)). Hh also plays a role in the development of limbs (Krauss et al., Cell 75: 1431-44 (1993); Laufer et al., Cell 79, 993-1003 (1994)), somites (Fan and Tessier-Lavigne, Cell 79, 1175-86 (1994); Johnson et al., Cell 79: 1165-73 (1994)), lungs (Bellusci et al., Develop. 124: 53-63 (1997) and skin (Oro et al., Science 276: 817-21 (1997)). Likewise, IHh and DHh are involved in bone, gut and germinal cell development (Apelqvist et al., Curr. Biol. 7: 801-4 (1997); Bellusci et al., Dev. Suppl. 124: 53-63 (1997); Bitgood et al., Curr. Biol. 6: 298-304 (1996); Roberts et al., Development 121: 3163-74 (1995)).

Human SHh is synthesized as a 45 kDa precursor protein that upon autocatalytic cleavage yields a 20 kDa N-terminal fragment that is responsible for normal hedgehog signaling activity; and a 25 kDa C-terminal fragment that is responsible for autoprocessing activity in which the N-terminal fragment is conjugated to a cholesterol moiety (Lee, J. J., et al. (1994) Science 266, 1528-1536; Bumcrot, D. A., et al. (1995), Mol. Cell. Biol. 15, 2294-2303; Porter, J. A., et al. (1995) Nature 374, 363-366). The N-terminal fragment consists of amino acid residues 24-197 of the full-length precursor sequence which remains membrane-associated through the cholesterol at its C-terminus (Porter, J. A., et al. (1996) Science 274, 255-258; Porter, J. A., et al. (1995) Cell 86, 21-34). Cholesterol conjugation is responsible for the tissue localization of the hedgehog signal.

At the cell surface, the Hh signal is thought to be relayed by the 12 transmembrane domain protein Patched (Ptc) (Hooper and Scott, Cell 59: 751-65 (1989); Nakano et al., Nature 341: 508-13 (1989)) and the G-protein-coupled-like receptor Smoothened (Smo) (Alcedo et al., Cell 86: 221-232 (1996); van den Heuvel and Ingham, Nature 382: 547-551 (1996)). Both genetic and biochemical evidence support a receptor model where Ptc and Smo are part of a multicomponent receptor complex (Chen and Struhl, Cell 87: 553-63 (1996); Marigo et al., Nature 384: 176-9 (1996); Stone et al., Nature 384: 129-34 (1996)). Upon binding of Hh to Ptc, the normal inhibitory effect of Ptc on Smo is relieved, allowing Smo to transduce the Hh signal across the plasma membrane. However, the exact mechanism by which Ptc controls Smo activity still has yet to be clarified.

The signaling cascade initiated by Smo results in activation of Gli transcription factors that translocate into the nucleus where they control transcription of target genes. Gli has been shown to influence transcription of Hh pathway inhibitors such as Ptc and Hip1 in a negative feedback loop indicating that tight control the Hh pathway activity is required for proper cellular differentiation and organ formation. Uncontrolled activation of Hh signaling pathway are associated with malignancies in particular those of the brain, skin and muscle as well as angiogenesis. An explanation for this is that Hh pathway has been shown to regulate cell proliferation in adults by activation of genes involved in cell cycle progression such as cyclin D which is involved in G1-S transition. Also, SHh blocks cell-cycle arrest mediated by p21, an inhibitor of cyclin dependent kinases. Hh signaling is further implicated in cancer by inducing components in the EGFR pathway (EGF, Her2) involved in proliferation as well as components in the PDGF (PDGFα) and VEGF pathways involved in angiogenesis. Loss of function mutations in the Ptc gene have been identified in patients with the basal cell nevus syndrome (BCNS), a hereditary disease characterized by multiple basal cell carcinomas (BCCs). Dysfunctional Ptc gene mutations have also been associated with a large percentage of sporadic basal cell carcinoma tumors (Chidambaram et al., Cancer Research 56: 4599-601 (1996); Gailani et al., Nature Genet. 14: 78-81 (1996); Hahn et al., Cell 85: 841-51 (1996); Johnson et al., Science 272: 1668-71 (1996); Unden et al., Cancer Res. 56: 4562-5; Wicking et al., Am. J. Hum. Genet. 60: 21-6 (1997)). Loss of Ptc function is thought to cause an uncontrolled Smo signaling in basal cell carcinoma. Similarly, activating Smo mutations have been identified in sporadic BCC tumors (Xie et al., Nature 391: 90-2 (1998)), emphasizing the role of Smo as the signaling subunit in the receptor complex for SHh.

Various inhibitors of hedgehog signaling have been investigated such as Cyclopamine, a natural alkaloid that has been shown to arrest cell cycle at G0-G1 and to induce apoptosis in SCLC. Cyclopamine is believed to inhibit Smo by binding to its heptahelical bundle. Forskolin has been shown to inhibit the Hh pathway downstream from Smo by activating protein kinase A (PKA) which maintains Gli transcription factors inactive. Despite advances with these and other compounds, there remains a need for potent inhibitors of the hedgehog signaling pathway.

SUMMARY OF THE INVENTION

In an aspect of the invention, there is provided a method for inhibiting hedgehog signaling in a cell comprising contacting said cell with a compound of formula I:

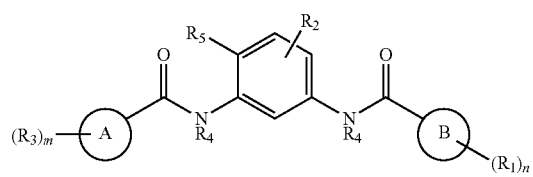

wherein
ring A is a carbocycle or heterocycle;
ring B is a carbocycle or heterocycle;

R₁ is hydroxyl, halogen, amino, nitro, cyano, alkyl, acyl, sulfonyl, sulfinyl, alkoxy, carbamoyl, acylamine, sulfamoyl or sulfonamide; wherein said amino, alkyl, acyl, sulfonyl, sulfinyl, alkoxy, carbamoyl, acylamine, sulfamoyl and sulfonamide substituent is optionally substituted with amino, halogen, hydroxyl, oxo, or is substituted with a carbocycle or heterocycle that is optionally substituted with hydroxyl, amino, halogen, haloalkyl, alkyl, alkoxy or acyl;

or R₁ is a carbocycle and a heterocycle that is optionally substituted with hydroxyl, halogen, amino, nitro, cyano, alkyl, acyl, sulfonyl, sulfinyl, alkoxy, carbamoyl, acylamine, sulfamoyl, sulfonamide, a carbocycle or heterocycle; wherein said amino, alkyl, acyl, sulfonyl, sulfinyl, alkoxy, carbamoyl, acylamine, sulfamoyl, sulfonamide, carbocycle and heterocycle substituent is optionally substituted with amino, halogen, hydroxyl, oxo, or is substituted with a carbocycle or heterocycle that is optionally substituted with hydroxyl, amino, halogen, haloalkyl, alkyl, alkoxy or acyl;

R₂ is halogen, hydroxyl, alkyl, acyl or alkoxy each optionally substituted with hydroxyl, halogen, amino, nitro, alkyl, acyl, sulfonyl or alkoxy;

R₃ is halogen, hydroxyl, carboxyl, alkyl, acyl, alkoxy, alkoxycarbonyl, carbamoyl, sulfide, sulfinyl, sulfonyl, a carbocycle or a heterocycle wherein each alkyl, acyl, alkoxy, alkoxycarbonyl, carbamoyl, sulfide, sulfinyl, sulfonyl, carbocycle and heterocycle is optionally substituted with hydroxyl, halogen, amino, nitro, alkyl, acyl, sulfonyl or alkoxy;

R₄ is H or alkyl;
R₅ is halogen, alkyl or haloalkyl;
m is 0-3;
n is 0-4;
and salts and solvates thereof.

In another aspect of the invention, there is provided a method for treating a disease or condition associated with the hedgehog signaling in a mammal, comprising administering to said mammal an effective amount of a compound of formula I.

In another aspect of the invention, there is provided a method for treating cancer comprising administering an effective amount of a compound of formula I to a mammal in need thereof.

In another aspect of the present invention there is provided novel compounds having the general formula (II)

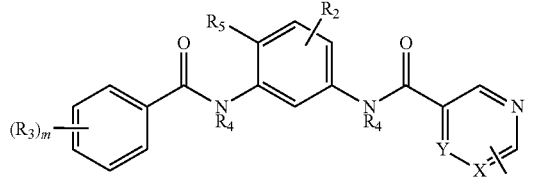

II wherein
X is CR₁, or N;
Y is CR₁, or N;
R₁ is hydroxyl, halogen, amino, nitro, cyano, alkyl, sulfonyl, sulfinyl, alkoxy, carbamoyl, acylamine, sulfamoyl or sulfonamide; wherein said amino, alkyl, acyl, sulfonyl, sulfinyl, alkoxy, carbamoyl, acylamine, sulfamoyl and sulfonamide substituent is optionally substituted with amino, halogen, hydroxyl, oxo, or is substituted with a carbocycle or heterocycle that is optionally substituted with hydroxyl, amino, halogen, haloalkyl, alkyl, alkoxy or acyl;

or R₁ is a carbocycle and a heterocycle that is optionally substituted with hydroxyl, halogen, amino, nitro, cyano, alkyl, acyl, sulfonyl, sulfinyl, alkoxy, carbamoyl, acylamine, sulfamoyl, sulfonamide, a carbocycle or heterocycle; wherein said amino, alkyl, acyl, sulfonyl, sulfinyl, alkoxy, carbamoyl, acylamine, sulfamoyl, sulfonamide, carbocycle and heterocycle substituent is optionally substituted with amino, halogen, hydroxyl, oxo, or is substituted with a carbocycle or heterocycle that is optionally substituted with hydroxyl, amino, halogen, haloalkyl, alkyl, alkoxy or acyl;

R₂ is halogen, hydroxyl, alkyl, acyl or alkoxy each optionally substituted with hydroxyl, halogen, amino, nitro, alkyl, acyl, sulfonyl or alkoxy;

R₃ is halogen, hydroxyl, carboxyl, alkyl, acyl, alkoxy, alkoxycarbonyl, carbamoyl, sulfide, sulfinyl, sulfonyl, a carbocycle or a heterocycle wherein each alkyl, acyl, alkoxy, alkoxycarbonyl, carbamoyl, sulfide, sulfinyl, sulfonyl, carbocycle and heterocycle is optionally substituted with hydroxyl, halogen, amino, nitro, alkyl, acyl, sulfonyl or alkoxy;

R₄ is H or alkyl;
R₅ is halogen, alkyl or haloalkyl;
m is 0-3;
n is 0-2;
and salts and solvates thereof.

In another aspect of the invention, there is provided compositions comprising compounds of formula II and a carrier, diluent or excipient.

In another aspect of the invention, there is provided processes for preparing compounds of the invention.

DETAILED DESCRIPTION OF THE PREFERRED EMBODIMENTS

"Acyl" means a carbonyl containing substituent represented by the formula —C(O)—R in which R is H, alkyl, a carbocycle, a heterocycle, carbocycle-substituted alkyl or heterocycle-substituted alkyl wherein the alkyl, alkoxy, carbocycle and heterocycle are as defined herein. Acyl groups include alkanoyl (e.g. acetyl), aroyl (e.g. benzoyl), and heteroaroyl.

"Alkyl" means a branched or unbranched, saturated or unsaturated (i.e. alkenyl, alkynyl) aliphatic hydrocarbon group, having up to 12 carbon atoms unless otherwise specified. When used as part of another term, for example "alkylamino", the alkyl portion is preferably a saturated hydrocarbon chain, however also includes unsaturated hydrocarbon carbon chains such as "alkenylamino" and "alkynylamino. "Alkylphosphinate" means a —P(O)R-alkyl group wherein R is H, alkyl, carbocycle-alkyl or heterocycle-alkyl. Examples of preferred alkyl groups include methyl, ethyl, n-propyl, isopropyl, n-butyl, iso-butyl, sec-butyl, tert-butyl, n-pentyl, 2-methylbutyl, 2,2-dimethylpropyl, n-hexyl, 2-methylpentyl, 2,2-dimethylbutyl, n-heptyl, 3-heptyl, 2-methylhexyl, and the like. The terms "lower alkyl" "C₁-C₄ alkyl" and "alkyl of 1 to 4 carbon atoms" are synonymous and used interchangeably to mean methyl, ethyl, 1-propyl, isopropyl, cyclopropyl, 1-butyl, sec-butyl or t-butyl. Unless specified, substituted, alkyl groups may contain one (preferably), two, three or four substituents which may be the same or different. Examples of the above substituted alkyl groups include, but are not limited to; cyanomethyl, nitromethyl, hydroxymethyl, trityloxymethyl, propionyloxymethyl, aminomethyl, carboxymethyl, carboxyethyl, carboxypropyl, alkyloxycarbonylmethyl, allyloxycarbonylaminomethyl, carbamoyloxymethyl, methoxymethyl, ethoxymethyl, t-butoxymethyl, acetoxymethyl, chloromethyl, bromomethyl, iodomethyl, trifluoromethyl, 6-hydroxyhexyl, 2,4-dichloro(n-butyl), 2-amino(iso-propyl), 2-carbamoyloxyethyl and the like. The alkyl group may also be substituted with a carbocycle group. Examples include cyclopropylmethyl, cyclobutylmethyl, cyclopentylmethyl, and cyclohexylmethyl groups, as well as the corresponding -ethyl, -propyl, -butyl, -pentyl, -hexyl groups, etc. Preferred substituted alkyls are substituted methyls e.g. a methyl group substituted by the same substituents as the "substituted $C_n$-$C_m$ alkyl" group. Examples of the substituted methyl group include groups such as hydroxymethyl, protected hydroxymethyl (e.g. tetrahydropyranyloxymethyl), acetoxymethyl, carbamoyloxymethyl, trifluoromethyl, chloromethyl, carboxymethyl, bromomethyl and iodomethyl.

"Amidine" or "amidino" means the group —C(NH)—NRR wherein each R is independently H, OH, alkyl, alkoxy, a carbocycle, a heterocycle, a carbocycle-substituted alkyl or a heterocycle-substituted alkyl; or both R groups together form a heterocycle. A preferred amidine is the group —C(NH)—NH$_2$.

"Amino" means primary (i.e. —NH$_2$), secondary (i.e. —NRH) and tertiary (i.e. —NRR) amines wherein R is independently alkyl, a carbocycle (e.g. aryl), a heterocycle (e.g. heteroaryl), carbocycle-substituted alkyl (e.g. benzyl) or a heterocycle-substituted alkyl or alternatively two R groups together with the nitrogen atom from which they depend form a heterocycle. Particular secondary and tertiary amines are alkylamine, dialkylamine, arylamine, diarylamine, aralkylamine and diaralkylamine. Particular secondary and tertiary amines are methylamine, ethylamine, propylamine, isopropylamine, phenylamine, benzylamine dimethylamine, diethylamine, dipropylamine and diisopropylamine.

"Amino-protecting group" as used herein refers to a derivative of the groups commonly employed to block or protect an amino group while reactions are carried out on other functional groups on the compound. Examples of such protecting groups include carbamates, amides, alkyl and aryl groups, imines, as well as many N-heteroatom derivatives which can be removed to regenerate the desired amine group. Preferred amino protecting groups are Boc, Fmoc and Cbz. Further examples of these groups are found in T. W. Greene and P. G. M. Wuts, "Protective Groups in Organic Synthesis", 2$^{nd}$ ed., John Wiley & Sons, Inc., New York, N.Y., 1991, chapter 7; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected amino" refers to an amino group substituted with one of the above amino-protecting groups.

"Aryl" when used alone or as part of another term means a carbocyclic aromatic group whether or not fused having the number of carbon atoms designated or if no number is designated, up to 14 carbon atoms. Aryl groups include phenyl, naphthyl, biphenyl, phenanthrenyl, naphthacenyl, and the like (see e.g. Lang's *Handbook of Chemistry* (Dean, J. A., ed) 13$^{th}$ ed. Table 7-2 [1985]). In a particular embodiment aryl may be phenyl. Substituted phenyl or substituted aryl denotes a phenyl group or aryl group substituted with one, two, three, four or five, such as 1-2, 1-3 or 1-4 substituents chosen, unless otherwise specified, from halogen (F, Cl, Br, I), hydroxy, protected hydroxy, cyano, nitro, alkyl (for example $C_1$-$C_6$ alkyl), alkoxy (for example $C_1$-$C_6$ alkoxy), benzyloxy, carboxy, protected carboxy, carboxymethyl, protected carboxymethyl, hydroxymethyl, protected hydroxymethyl, aminomethyl, protected aminomethyl, trifluoromethyl, alkylsulfonylamino, arylsulfonylamino, heterocyclylsulfonylamino, heterocyclyl, aryl, or other groups specified. One or more methane (CH) and/or methylene (CH$_2$) groups in these substituents may in turn be substituted with a similar group as those denoted above. Examples of the term "substituted phenyl" includes but is not limited to a mono- or di(halo) phenyl group such as 2-chlorophenyl, 2-bromophenyl, 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono- or di(hydroxy)phenyl group such as 4-hydroxyphenyl, 3-hydroxyphenyl, 2,4-dihydroxyphenyl, the protected-hydroxy derivatives thereof and the like; a nitrophenyl group such as 3- or 4-nitrophenyl; a cyanophenyl group, for example, 4-cyanophenyl; a mono- or di(lower alkyl)phenyl group such as 4-methylphenyl, 2,4-dimethylphenyl, 2-methylphenyl, 4-(iso-propyl)phenyl, 4-ethylphenyl, 3-(n-propyl)phenyl and the like; a mono or di(alkoxy)phenyl group, for example, 3,4-dimethoxyphenyl, 3-methoxy-4-benzyloxyphenyl, 3-methoxy-4-(1-chloromethyl)benzyloxy-phenyl, 3-ethoxyphenyl, 4-(isopropoxy) phenyl, 4-(t-butoxy)phenyl, 3-ethoxy-4-methoxyphenyl and the like; 3- or 4-trifluoromethylphenyl; a mono- or dicarboxyphenyl or (protected carboxy)phenyl group such 4-carboxyphenyl; a mono- or di(hydroxymethyl)phenyl or (protected hydroxymethyl)phenyl such as 3-(protected hydroxymethyl) phenyl or 3,4-di(hydroxymethyl)phenyl; a mono- or di(aminomethyl)phenyl or (protected aminomethyl)phenyl such as 2-(aminomethyl)phenyl or 2,4-(protected aminomethyl)phenyl; or a mono- or di(N-(methylsulfonylamino))phenyl such as 3-(N-methylsulfonylamino))phenyl. Also, the term "substituted phenyl" represents disubstituted phenyl groups where the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, and the like, as well as trisubstituted phenyl groups where the substituents are different, for example 3-methoxy-4-benzyloxy-6-methyl sulfonylamino, 3-methoxy-4-benzyloxy-6-phenyl sulfonylamino, and tetrasubstituted phenyl groups where the substituents are different such as 3-methoxy-4-benzyloxy-5-methyl-6-phenyl sulfonylamino. Substituted phenyl groups include 2-chlorophenyl, 2-aminophenyl, 2-bromophenyl, 3-methoxyphenyl, 3-ethoxy-phenyl, 4-benzyloxyphenyl, 4-methoxyphenyl, 3-ethoxy-4-benzyloxyphenyl, 3,4-diethoxyphenyl, 3-methoxy-4-benzyloxyphenyl, 3-methoxy-4-(1-chloromethyl)benzyloxy-phenyl, 3-methoxy-4-(1-chloromethyl)benzyloxy-6-methyl sulfonyl aminophenyl groups. Fused aryl rings may also be substituted with any (for example 1, 2 or 3) of the substituents specified herein in the same manner as substituted alkyl groups.

"Carbamoyl" means an aminocarbonyl containing substituent represented by the formula —C(O)N(R)$_2$ in which R is H, hydroxyl, alkoxy, alkyl, a carbocycle, a heterocycle, carbocycle-substituted alkyl or alkoxy, or heterocycle-substituted alkyl or alkoxy wherein the alkyl, alkoxy, carbocycle and heterocycle are as herein defined. Carbamoyl groups include alkylaminocarbonyl (e.g. ethylaminocarbonyl, Et-NH—CO—), arylaminocarbonyl (e.g. phenylaminocarbonyl), aralkylaminocarbonyl (e.g. benzylaminocarbonyl) a heterocycleaminocarbonyl (e.g. piperizinylaminocarbonyl), and in particular a heteroarylaminocarbonyl (e.g. pyridylaminocarbonyl).

"Carbocyclyl", "carbocyclic", "carbocycle" and "carbocycle" alone and when used as a moiety in a complex group such as a carbocycloalkyl group, refers to a mono-, bi-, or tricyclic aliphatic ring having 3 to 14 carbon atoms and preferably 3 to 7 carbon atoms which may be saturated or unsaturated, aromatic or non-aromatic. Preferred saturated carbocyclic groups include cyclopropyl, cyclobutyl, cyclopentyl and cyclohexyl groups and more preferred are cyclopropyl and cyclohexyl and most preferred is cyclohexyl. Preferred unsaturated carbocycles are aromatic e.g. aryl groups as previously defined, the most preferred being phenyl. The terms "substituted carbocyclyl", "substituted carbocycle" and "substituted carbocycle" unless otherwise specified mean these groups substituted by the same substituents as the "substituted alkyl" group.

"Carboxy-protecting group" as used herein refers to one of the ester derivatives of the carboxylic acid group commonly employed to block or protect the carboxylic acid group while reactions are carried out on other functional groups on the compound. Examples of such carboxylic acid protecting groups include 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, alkyl such as t-butyl or t-amyl, trityl, 4-methoxytrityl, 4,4'-dimethoxytrityl, 4,4',4"-trimethoxytrityl, 2-phenylprop-2-yl, trimethylsilyl, t-butyldimethylsilyl, phenacyl, 2,2,2-trichloroethyl, beta-(trimethylsilyl)ethyl, beta-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl, and like moieties. The species of carboxy-protecting group employed is not critical so long as the derivatized carboxylic acid is stable to the condition of subsequent reaction(s) on other positions of the molecule and can be removed at the appropriate point without disrupting the remainder of the molecule. In particular, it is important not to subject a carboxy-protected molecule to strong nucleophilic bases, such as lithium hydroxide or NaOH, or reductive conditions employing highly activated metal hydrides such as $LiAlH_4$. (Such harsh removal conditions are also to be avoided when removing amino-protecting groups and hydroxy-protecting groups, discussed below.) Preferred carboxylic acid protecting groups are the alkyl (e.g. methyl, ethyl, t-butyl), allyl, benzyl and p-nitrobenzyl groups. Similar carboxy-protecting groups used in the cephalosporin, penicillin and peptide arts can also be used to protect a carboxy group substituents. Further examples of these groups are found in T. W. Greene and P. G. M. Wuts, "Protective Groups in Organic Synthesis", $2^{nd}$ ed., John Wiley & Sons, Inc., New York, N.Y., 1991, chapter 5; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5. The term "protected carboxy" refers to a carboxy group substituted with one of the above carboxy-protecting groups.

"Guanidine" means the group —NH—C(NH)—NHR wherein R is H, alkyl, a carbocycle, a heterocycle, a carbocycle-substituted alkyl, or a heterocycle-substituted alkyl. A particular guanidine group is —NH—C(NH)—$NH_2$.

"Heterocyclic group", "heterocyclic", "heterocycle", "heterocyclyl", or "heterocyclo" alone and when used as a moiety in a complex group such as a heterocycloalkyl group, are used interchangeably and refer to any mono-, bi-, or tricyclic, saturated or unsaturated, aromatic (heteroaryl) or non-aromatic ring having the number of atoms designated, generally from 5 to about 14 ring atoms, where the ring atoms are carbon and at least one heteroatom (nitrogen, sulfur or oxygen) and preferably 1 to 4 heteroatoms. "Heterocyclosulfonyl" means a —$SO_2$-heterocycle group; "heterocyclosulfinyl" means a —SO-heterocycle group. Typically, a 5-membered ring has 0 to 2 double bonds and 6- or 7-membered ring has 0 to 3 double bonds and the nitrogen or sulfur heteroatoms may optionally be oxidized (e.g. SO, $SO_2$), and any nitrogen heteroatom may optionally be quaternized. Preferred non-aromatic heterocycles include morpholinyl (morpholino), pyrrolidinyl, oxiranyl, oxetanyl, tetrahydrofuranyl, 2,3-dihydrofuranyl, 2H-pyranyl, tetrahydropyranyl, thioranyl, thietanyl, tetrahydrothietanyl, aziridinyl, azetidinyl, 1-methyl-2-pyrrolyl, piperazinyl and piperidinyl. A "heterocycloalkyl" group is a heterocycle group as defined above covalently bonded to an alkyl group as defined above. Preferred 5-membered heterocycles containing a sulfur or oxygen atom and one to three nitrogen atoms include thiazolyl, in particular thiazol-2-yl and thiazol-2-yl N-oxide, thiadiazolyl, in particular 1,3,4-thiadiazol-5-yl and 1,2,4-thiadiazol-5-yl, oxazolyl, preferably oxazol-2-yl, and oxadiazolyl, such as 1,3,4-oxadiazol-5-yl, and 1,2,4-oxadiazol-5-yl. Preferred 5-membered ring heterocycles containing 2 to 4 nitrogen atoms include imidazolyl, preferably imidazol-2-yl; triazolyl, preferably 1,3,4-triazol-5-yl; 1,2,3-triazol-5-yl, 1,2,4-triazol-5-yl, and tetrazolyl, preferably 1H-tetrazol-5-yl. Preferred benzo-fused 5-membered heterocycles are benzoxazol-2-yl, benzthiazole-2-yl and benzimidazol-2-yl. Preferred 6-membered heterocycles contain one to three nitrogen atoms and optionally a sulfur or oxygen atom, for example pyridyl, such as pyrid-2-yl, pyrid-3-yl, and pyrid-4-yl; pyrimidyl, preferably pyramid-2-yl and pyrimid-4-yl; triazinyl, preferably 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are a preferred group. Substituents for optionally substituted heterocycles, and further examples of the 5- and 6-membered ring systems discussed above can be found in W. Druckheimer et al., U.S. Pat. No. 4,278,793.

"Heteroaryl" alone and when used as a moiety in a complex group such as a heteroaralkyl group, refers to any mono-, bi-, or tricyclic aromatic ring system having the number of atoms designated where at least one ring is a 5-, 6- or 7-membered ring containing from one to four heteroatoms selected from the group nitrogen, oxygen, and sulfur, and preferably at least one heteroatom is nitrogen (*Lang's Handbook of Chemistry*, supra). Included in the definition are any bicyclic groups where any of the above heteroaryl rings are fused to a benzene ring. Heteroaryls in which nitrogen or oxygen is the heteroatom are preferred. The following ring systems are examples of the heteroaryl (whether substituted or unsubstituted) groups denoted by the term "heteroaryl": thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxozinyl, oxathiazinyl, tetrazinyl, thiatriazinyl, oxatriazinyl, dithiadiazinyl, imidazolinyl, dihydropyrimidyl, tetrahydropyrimidyl, tetrazolo[1,5-b]pyridazinyl and purinyl, as well as benzo-fused derivatives, for example benzoxazolyl, benzofuryl, benzothiazolyl, benzothiadiazolyl, benzotriazolyl, benzoimidazolyl and indolyl. A particularly preferred group of "heteroaryl" include; 1,3-thiazol-2-yl, 4-(carboxymethyl)-5-methyl-1,3-thiazol-2-yl, 4-(carboxymethyl)-5-methyl-1,3-thiazol-2-yl sodium salt, 1,2,4-thiadiazol-5-yl, 3-methyl-1,2,4-thiadiazol-5-yl, 1,3,4-triazol-5-yl, 2-methyl-1,3,4-triazol-5-yl, 2-hydroxy-1,3,4-triazol-5-yl, 2-carboxy-4-methyl-1,3,4-triazol-5-yl sodium salt, 2-carboxy-4-methyl-1,3,4-triazol-5-yl, 1,3-oxazol-2-yl, 1,3,4-oxadiazol-5-yl, 2-methyl-1,3,4-oxadiazol-5-yl, 2-(hydroxymethyl)-1,3,4-oxadiazol-5-yl, 1,2,4-oxadiazol-5-yl, 1,3,4-thiadiazol-5-yl, 2-thiol-1,3,4-thiadiazol-5-yl, 2-(methylthio)-1,3,4-thiadiazol-5-yl, 2-amino-1,3,4-thiadiazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 2-methyl-1H-tetrazol-5-yl, 1,2,3-triazol-5-yl, 1-methyl-1,2,3-triazol-5-yl, 2-methyl-1,2,3-triazol-5-yl, 4-methyl-1,2,3-triazol-5-yl, pyrid-2-yl N-oxide, 6-methoxy-2-(n-oxide)-pyridaz-3-yl, 6-hydroxypyridaz-3-yl, 1-methylpyrid-2-yl, 1-methylpyrid-4-yl, 2-hydroxypyrimid-4-yl, 1,4,5,6-tetrahydro-5,6-dioxo-4-methyl-as-triazin-3-yl, 1,4,5,6-tetrahydro-4-(formylmethyl)-5,6-dioxo-as-triazin-3-yl, 2,5-dihydro-5-oxo-6-hydroxy-astriazin-3-yl, 2,5-dihydro-5-oxo-6-hydroxy-astriazin-3-yl sodium salt, 2,5-dihydro-5-oxo-6-hydroxy-2-methyl-astriazin-3-yl sodium salt, 2,5-dihydro-5-oxo-6-hydroxy-2-methyl-as-triazin-3-yl, 2,5-dihydro-5-oxo-6-methoxy-2-methyl-as-triazin-3-yl, 2,5-dihydro-5-oxo-as-triazin-3-yl, 2,5-dihydro-5-oxo-2-methyl-as-triazin-3-yl, 2,5-dihydro-5-oxo-2,6-dimethyl-as-triazin-3-yl, tetrazolo[1,5-b]pyridazin-6-yl and 8-aminotetrazolo[1,5-b]-pyridazin-6-yl. An alternative group of "heteroaryl" includes; 4-(carboxymethyl)-5-methyl-1,3-thiazol-2-yl, 4-(carboxymethyl)-5-methyl-1,3-thiazol-2-yl sodium salt, 1,3,4-triazol-5-yl, 2-methyl-1,3,4-triazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 1,2,3-triazol-5-yl, 1,4,5,6-tetrahydro-5,6-dioxo-4-methyl-as-triazin-3-yl, 1,4,5,6-tetrahydro-4-(2-formylmethyl)-5,6-dioxo-as-triazin-3-yl, 2,5-dihydro-5-oxo-6-hydroxy-2-methyl-as-triazin-3-yl sodium salt, 2,5-dihydro-5-oxo-6-hydroxy-2-methyl-as-triazin-3-yl, tetrazolo[1,5-b]pyridazin-6-yl, and 8-aminotetrazolo[1,5-b]pyridazin-6-yl.

"Hydroxy-protecting group" as used herein refers to a derivative of the hydroxy group commonly employed to block or protect the hydroxy group while reactions are carried out on other functional groups on the compound. Examples of such protecting groups include tetrahydropyranyloxy, benzoyl, acetoxy, carbamoyloxy, benzyl, and silylether (e.g. TBS, TBDPS) groups. Further examples of these groups are found in T. W. Greene and P. G. M. Wuts, "Protective Groups in Organic Synthesis", $2^{nd}$ ed., John Wiley & Sons, Inc., New York, N.Y., 1991, chapters 2-3; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected hydroxy" refers to a hydroxy group substituted with one of the above hydroxy-protecting groups.

"Optionally substituted" unless otherwise specified means that a group may be substituted by one or more (e.g. 0, 1, 2, 3 or 4) of the substituents listed for that group in which said substituents may be the same or different. In an embodiment an optionally substituted group has 1 substituent. In another embodiment an optionally substituted group has 2 substituents. In another embodiment an optionally substituted group has 3 substituents.

"Pharmaceutically acceptable salts" include both acid and base addition salts. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, TEA, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, trimethamine, dicyclohexylamine, choline, and caffeine.

"Phosphinate" means —P(O)R—OR wherein each R is independently H, alkyl, carbocycle, heterocycle, carbocycloalkyl or heterocycloalkyl. Particular phosphinate groups are alkylphosphinate (i.e. —P(O)R—O-alkyl), for example —P(O)Me-OEt.

"Sulfamoyl" means —SO$_2$—N(R)$_2$ wherein each R is independently H, alkyl, carbocycle, heterocycle, carbocycloalkyl or heterocycloalkyl. Particular sulfamoyl groups are alkylsulfamoyl, for example methylsulfamoyl (—SO$_2$—NHMe); arylsulfamoyl, for example phenylsulfamoyl; aralkylsulfamoyl, for example benzylsulfamoyl.

"Sulfide" means —S—R wherein R is H, alkyl, carbocycle, heterocycle, carbocycloalkyl or heterocycloalkyl. Particular sulfide groups are mercapto, alkylsulfide, for example methylsulfide (—S-Me); arylsulfide, for example phenylsulfide; aralkylsulfide, for example benzylsulfide.

"Sulfinyl" means a —SO—R group wherein R is alkyl, carbocycle, heterocycle, carbocycloalkyl or heterocycloalkyl. Particular sulfinyl groups are alkylsulfinyl (i.e. —SO-alkyl), for example methylsulfinyl; arylsulfinyl (i.e. —SO-aryl) for example phenylsulfinyl; aralkylsulfinyl, for example benzylsulfinyl.

"Sulfonamide" means —NR—SO$_2$—R wherein each R is independently H, alkyl, carbocycle, heterocycle, carbocycloalkyl or heterocycloalkyl), a carbocycle or a heterocycle. Particular sulfonamide groups are alkylsulfonamido (e.g. —NH—SO$_2$-alkyl), for example methylsulfonamide; acylsulfonamide (i.e. —NH—SO$_2$-aryl) for example phenylsulfonamide; aralkylsulfonamide, for example benzylsulfonamide.

"Sulfonyl" means a —SO$_2$—R group wherein R is alkyl, carbocycle, heterocycle, carbocycloalkyl or heterocycloalkyl. Particular sulfonyl groups are alkylsulfonyl (i.e. —SO$_2$-alkyl), for example methylsulfonyl; arylsulfonyl, for example phenylsulfonyl; aralkylsulfonyl, for example benzylsulfonyl.

The phrase "and salts and solvates thereof" as used herein means that compounds of the inventions may exist in one or a mixture of salts and solvate forms. For example a compound of the invention may be substantially pure in one particular salt or solvate form or else may be mixtures of two or more salt or solvate forms.

The present invention provides a method for inhibiting hedgehog signaling in a cell comprising contacting said cell with a compounds having the general formula I:

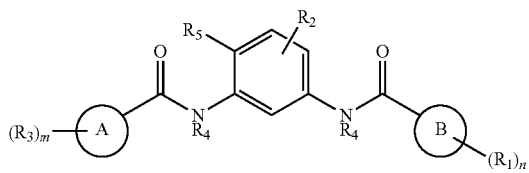

wherein ring A, ring B, $R_1$, $R_2$, $R_3$, $R_4$, $R_5$, m and n are as defined herein.

In another aspect of the invention, there are provided novel compounds having the general formula (I).

Ring A is a carbocycle or heterocycle substituted with 0 to 3 (i.e. m is 0-3) $R_3$ which are independently halogen, hydroxyl, carboxyl, alkyl, acyl, alkoxy, alkoxycarbonyl, carbamoyl, sulfide, sulfinyl, sulfonyl, a carbocycle or a heterocycle wherein each alkyl, acyl, alkoxy, alkoxycarbonyl, carbamoyl, sulfide, sulfinyl, sulfonyl, carbocycle and heterocycle is optionally substituted with hydroxyl, halogen, amino, nitro, alkyl, acyl, sulfonyl or alkoxy. In a particular embodiment, A is optionally substituted aryl or heteroaryl. In particular embodiment ring A is optionally substituted benzene, pyridine, pyrimidine, pyrazine, thiophene, thiazole, imidazole, pyrrole or pyrazole. In a particular embodiment ring A is benzene.

Ring B is a carbocycle or heterocycle substituted with 0 to 4 (i.e. n is 0-4) $R_1$ which are independently hydroxyl, halogen, amino, nitro, cyano, alkyl, acyl, sulfonyl, sulfinyl, alkoxy, carbamoyl, acylamine, sulfamoyl or sulfonamide; wherein said amino, alkyl, acyl, sulfonyl, sulfinyl, alkoxy, carbamoyl, acylamine, sulfamoyl and sulfonamide substituent is optionally substituted with amino, halogen, hydroxyl, oxo (=O), or is substituted with a carbocycle or heterocycle that is optionally substituted with hydroxyl, amino, halogen, haloalkyl, alkyl, alkoxy or acyl; or $R_1$ is a carbocycle and a heterocycle that is optionally substituted with hydroxyl, halogen, amino, nitro, cyano, alkyl, acyl, sulfonyl, sulfinyl, alkoxy, carbamoyl, acylamine, sulfamoyl, sulfonamide, a carbocycle or heterocycle; wherein said amino, alkyl, acyl, sulfonyl, sulfinyl, alkoxy, carbamoyl, acylamine, sulfamoyl, sulfonamide, carbocycle and heterocycle substituent is optionally substituted with amino, halogen, hydroxyl, oxo, or is substituted with a carbocycle or heterocycle that is optionally substituted with hydroxyl, amino, halogen, haloalkyl, alkyl, alkoxy or acyl;

In an embodiment ring B is aryl or heteroaryl. In a particular embodiment ring B is benzene. In a particular embodiment ring B is pyridine, pyrazine, pyrimidine, pyrazine, 1,2,4-triazine, thiophene, thiazole, imidazole, pyrrole or pyrazole. In a particular embodiment ring B is pyridin-2-yl. In a particular embodiment ring B is 1,2,4-triazin-3-yl. In a particular embodiment ring B is pyrimidin-3-yl. In a particular embodiment ring B is pyrazin-2-yl. In a particular embodiment ring B is 1H-pyrazol-3-yl. In a particular embodiment ring B is thiazol-4-yl.

In particular embodiments, the heterocycle (in all instances, e.g., for A, B, $R_1$, $R_3$ and as a substituent) has only N heteroatoms, only O heteroatoms or only S heteroatoms, or has a combination of heteroatoms, e.g., N and S atoms, N and O atoms, O and S atoms, or N, O and S atoms.

$R_1$ is hydroxyl, halogen, amino, nitro, cyano, alkyl, sulfonyl, sulfinyl, alkoxy, carbamoyl, acylamine, sulfamoyl or sulfonamide; wherein said amino, alkyl, acyl, sulfonyl, sulfinyl, alkoxy, carbamoyl, acylamine, sulfamoyl and sulfonamide substituent is optionally substituted with amino, halogen, hydroxyl, oxo, or is substituted with a carbocycle or heterocycle that is optionally substituted with hydroxyl, amino, halogen, haloalkyl, alkyl, alkoxy or acyl. In an embodiment, $R_1$ is halogen, alkyl, alkoxy, alkylsulfonyl, haloalkyl or alkylsulfonylalkyl. In a particular embodiment $R_1$ is Cl, methyl, methoxy, methylsulfonyl, trifluoromethylsulfonyl, $CF_3$, bromomethyl, methylsulfonylmethyl. In another embodiment $R_1$ is heterocyclyalkyl, heterocycleaminoalkyl. In a particular embodiment $R_1$ is piperazinylmethyl, piperidinylmethyl, morpholinomethyl optionally substituted with methyl or ethyl. In another particular embodiment $R_1$ is 4-methylpiperidin-4-ylaminomethyl.

Alternatively, $R_1$ is a carbocycle and a heterocycle that is optionally substituted with hydroxyl, halogen, amino, nitro, cyano, alkyl, acyl, sulfonyl, sulfinyl, alkoxy, carbamoyl, acylamine, sulfamoyl, sulfonamide, a carbocycle or heterocycle; wherein said amino, alkyl, acyl, sulfonyl, sulfinyl, alkoxy, carbamoyl, acylamine, sulfamoyl, sulfonamide, carbocycle and heterocycle substituent is optionally substituted with amino, halogen, hydroxyl, oxo, or is substituted with a carbocycle or heterocycle that is optionally substituted with hydroxyl, amino, halogen, haloalkyl, alkyl, alkoxy or acyl. In an embodiment, $R_1$ is piperazine optionally substituted with alkyl, acyl, or hydroxyalkyl. In a particular embodiment $R_1$ is methyl, ethyl, acetyl, propanoyl, butanoyl, 3-methylbutanoyl, cyclopropylcarbonyl or hydroxyethyl. In another embodiment $R_1$ is 1,2,4-triazol-1-yl. In another embodiment $R_1$ is piperidine optionally substituted with hydroxyl. In a particular embodiment $R_1$ is 4-hydroxypiperidin-1-yl. In another embodiment $R_1$ is morpholino. In another embodiment $R_1$ is phenyl.

In an embodiment, $R_1$ is alkyl, haloalkyl, aryl, a heterocycle or a heterocycloalkyl wherein said aryl, heterocycle and heterocycloalkyl is optionally substituted with hydroxy, halogen, alkyl, alkanoyl or hydroxyalkyl. In an embodiment, $R_1$ is a heterocycle optionally substituted with alkyl or alkanoyl. In an embodiment, $R_1$ is alkyl or haloalkyl. In an embodiment, $R_1$ is Me, $CF_3$, Ph, 4-F-phenyl, piperazin-1-yl, 4-methylpiperazin-1-yl, 4-ethylpiperazin-1-yl, 4-acetylpiperazin-1-yl, 3,5-dimethylpiperazine-1-yl, 4-(2-hydroxyethyl)-piperazin-1-yl, (4-methylpiperazin-1-yl)methyl, (4-ethylpiperazin-1-yl)methyl, (4-acetylpiperazin-1-yl)methyl, (3,5-dimethylpiperazine-1-yl)methyl, 4-hydroxypiperidin-1-yl, (piperidin-1-yl)methyl, (1-methylpiperidin-4-ylamino)methyl, morpholino, (3,5-dimethyl)morpholino, morpholinomethyl or 1H-1,2,4-triazol-1-yl.

$R_2$ is halogen, hydroxyl, alkyl, acyl or alkoxy each optionally substituted with hydroxyl, halogen, amino, nitro, alkyl, acyl, sulfonyl or alkoxy. In a particular embodiment $R_2$ is H.

$R_3$ is halogen, hydroxyl, carboxyl, alkyl, acyl, alkoxy, alkoxycarbonyl, carbamoyl, sulfide, sulfinyl, sulfonyl, a carbocycle or a heterocycle wherein each alkyl, acyl, alkoxy, alkoxycarbonyl, carbamoyl, sulfide, sulfinyl, sulfonyl, carbocycle and heterocycle is optionally substituted with hydroxyl, halogen, amino, nitro, alkyl, acyl, sulfonyl or alkoxy. In a particular embodiment, $R_3$ is halogen (e.g. F or Cl), alkyl, alkylsulfonyl, alkylsulfonylalkyl or a heterocycle. In a particular embodiment, $R_3$ is Me, F, Cl, —$CH_2$—$SO_2$—Me, —$SO_2$-Me, 1H-1,2,4-triazol-1-yl, 1H-imidazol-1-yl, morpholino, thiomorpholino-methyl (in which S is in the oxidized form $SO_2$), 1,2,3-thiadiazol-4-yl or N-methyl-piperizinyl. In a particular embodiment, ring A is substituted with $R_3$ groups as follows: o-Me, m-Me, p-Me, p-F, o-F, m-F, m-F and p-F, o—Cl, m—Cl, p—Cl, p-F and m—Cl, p-CH$_2$—SO$_2$-Me, p-SO$_2$-Me, o—Cl, p-1H-1,2,4-triazol-1-yl, p-1H-imidazol-1-yl, o-morpholino, p-thiomorpholino-methyl (in which S is in the oxidized form SO$_2$), p-1,2,3-thiadiazol-4-yl or p-N-methyl-piperizinyl.

In a particular embodiment m is 0, i.e. R$_3$ is absent. In another particular embodiment m is 1-3. In a particular embodiment R$_3$ is 1.

R$_4$ in each occurrence is independently H or alkyl. In an embodiment R$_4$ is independently H or methyl. In an embodiment R$_4$ is H in each occurrence. In another embodiment R$_4$ is methyl in each occurrence.

R$_5$ is halogen, alkyl or haloalkyl. In a particular embodiment R$_5$ is chloro. In another embodiment R$_5$ is fluoro. In another embodiment R$_5$ is methyl. In another embodiment R$_5$ is trifluoromethyl.

In another aspect of the invention there is provided compounds having the general formula II:

II wherein R$_1$, R$_2$, R$_3$, R$_4$, R$_5$, m and n are as defined herein and
X is CR$_1$, or N;
Y is CR$_1$, or N; and
solvates and solvates thereof.

In a particular embodiment X and Y are both CR$_1$. In a particular embodiment X is N and Y is CR$_1$. In a particular embodiment X is CR$_1$ and Y is N. In another particular embodiment X and Y are both N.

In a particular embodiment, compounds of the invention have the general formula IIa:

IIa wherein R$_2$, R$_3$, R$_4$, R$_5$ and m are as defined herein;
R$_6$ is independently H or alkyl; and
R$_7$ is H, alkyl, hydroxy substituted alkyl or alkanoyl.

In a particular embodiment both R$_6$ are H. In a particular embodiment both R$_6$ are methyl. In a particular embodiment R$_7$ is H. In a particular embodiment R$_7$ is acetyl.

In a particular embodiment, compounds of the invention have the general formula IIb:

IIb wherein R$_2$, R$_3$, R$_4$, R$_5$ and m are as defined herein and R$_6$ is independently H or alkyl. In a particular embodiment both R$_6$ are H. In a particular embodiment both R$_6$ are methyl.

In a particular embodiment, compounds of the invention have the general formula IIc:

IIc wherein R$_2$, R$_3$, R$_4$, R$_5$ and m are as defined herein.

In a particular embodiment, compounds of the invention have the general formula III:

III wherein R$_1$, R$_2$, R$_3$, R$_4$, R$_5$ and m are as defined herein and R$_6$ is H or alkyl. In a particular embodiment R$_6$ is H. In a particular embodiment R$_6$ is methyl.

In a particular embodiment, compounds of the invention have the general formula IV:

IV wherein R$_1$, R$_2$, R$_3$, R$_4$, R$_5$ and m are as defined herein. In a particular embodiment R$_1$ is aryl. In a particular embodiment R$_1$ is phenyl.

In a particular embodiment, compounds of the invention have the general formula V:

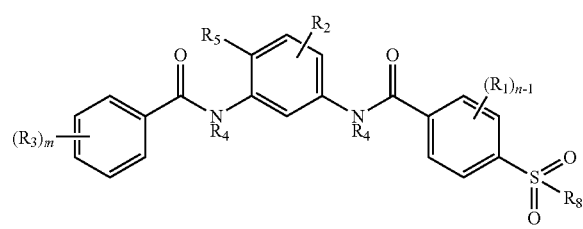

V wherein $R_1$, $R_2$, $R_3$, $R_4$, $R_5$, m and n are as defined herein; and $R_8$ is H, alkyl or haloalkyl. In a particular embodiment, $R_8$ is methyl or $CF_3$. In a particular embodiment n is 2 and $R_1$ is H or Cl.

In a particular embodiment, compounds of the invention have the general formula VI:

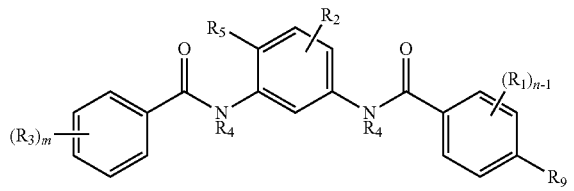

VI wherein $R_1$, $R_2$, $R_3$, $R_4$, $R_5$, m and n are as defined herein; and $R_9$ is heteroaryl. In a particular embodiment, $R_9$ is 1H-imidazol-1-yl. In a particular embodiment $R_9$ is 1H-1,2,4-triazol-1-yl.

In another aspect of the invention, there is provided a method for inhibiting hedgehog signaling in a cell comprising contacting said cell with a compound of any one of formulae I, II, IIa-IIc and III-VI.

In another aspect of the invention, there is provided a method for treating cancer comprising administering to a mammal in need thereof an effective amount of a compound of any one of formulae I, II, IIa-IIc and III-VI.

In another aspect of the invention, there is provided a method for treating a disease or condition associated with the hedgehog signaling in a mammal, comprising administering to said mammal an effective amount of a compound of any one of formulae I, II, IIa-IIc and III-VI.

Particular compounds of the invention include, but are not limited to the following:

1

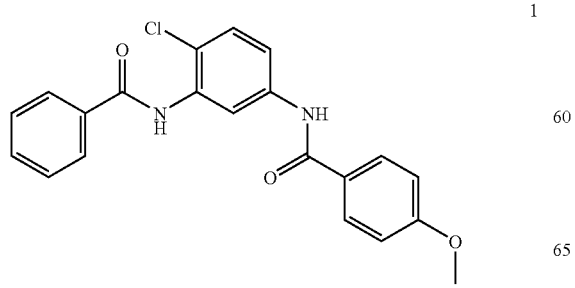

-continued

2

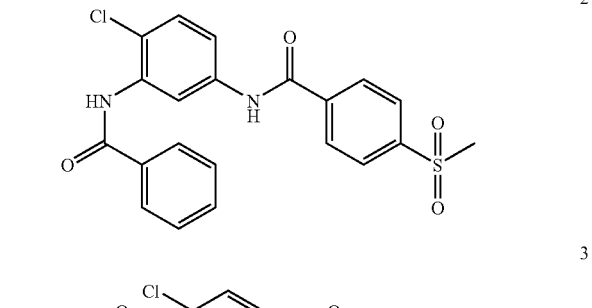

3

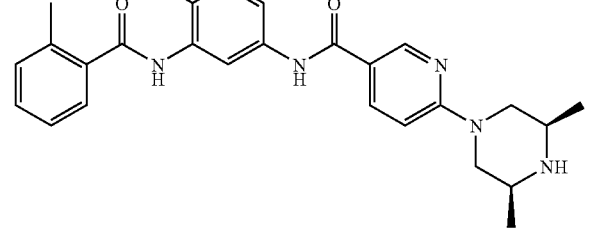

4

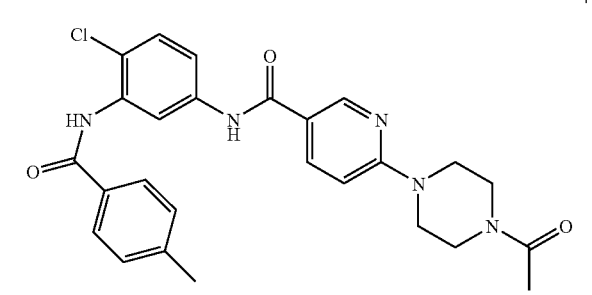

5

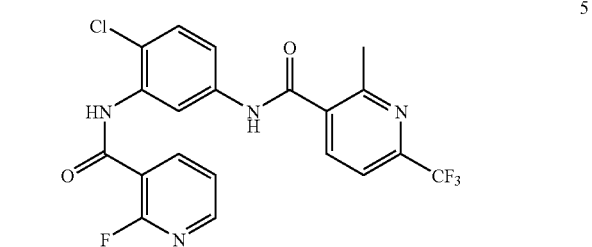

6

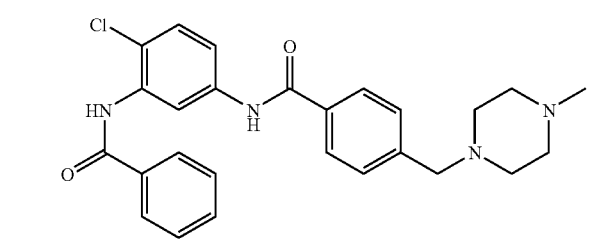

7

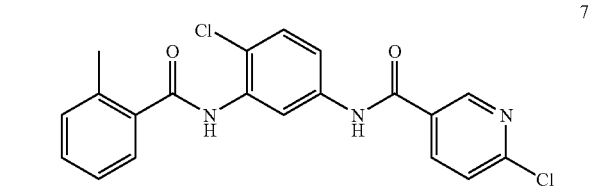

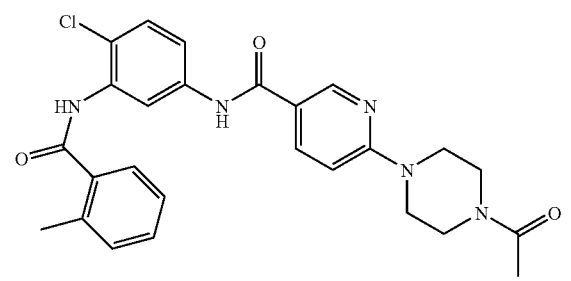
8
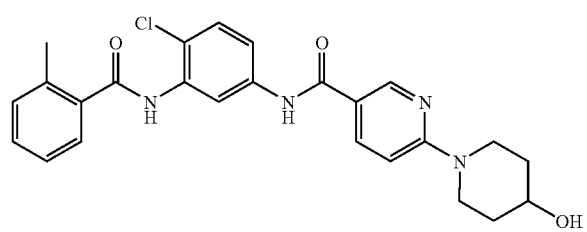
9
10
11
12
13
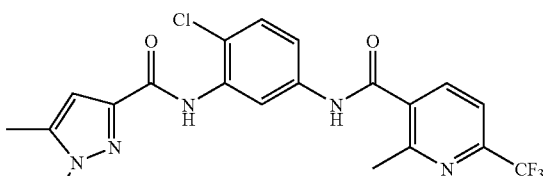
14
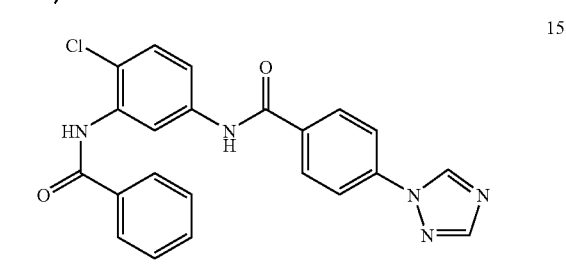
15
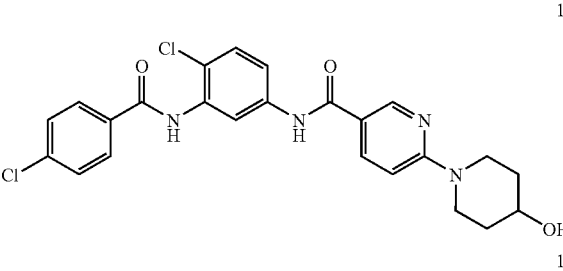
16
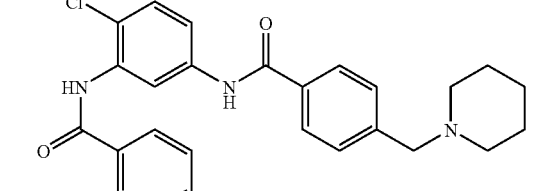
17
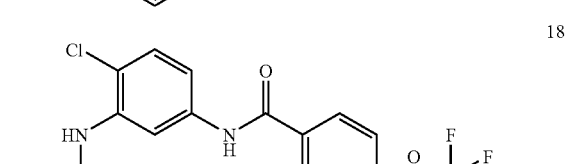
18
19
20

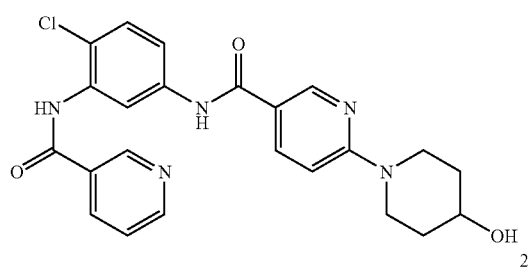
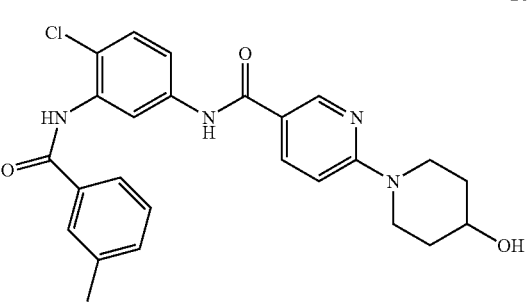
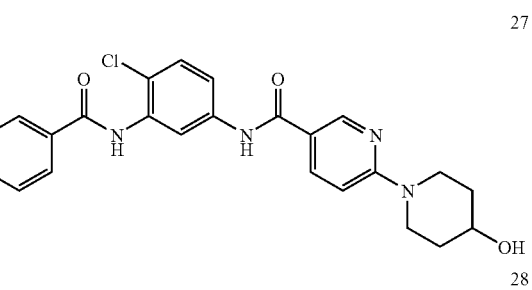
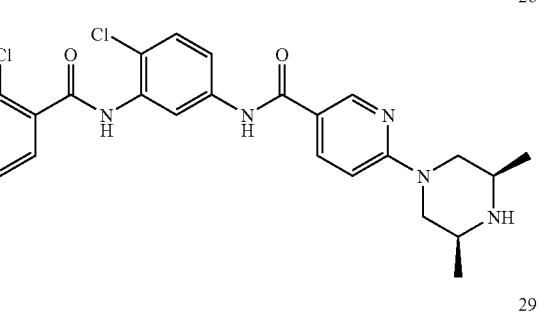
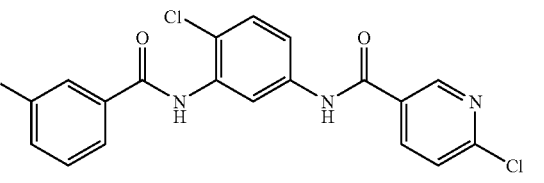
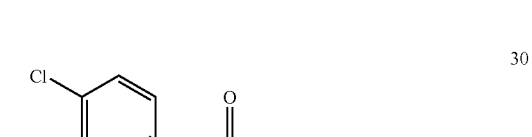
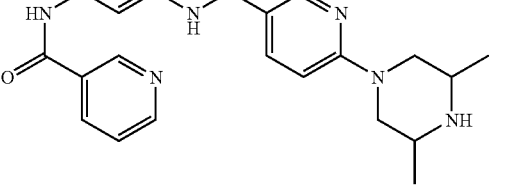

-continued
32
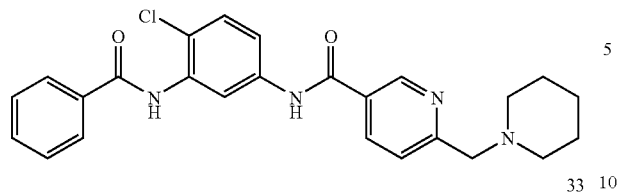
33
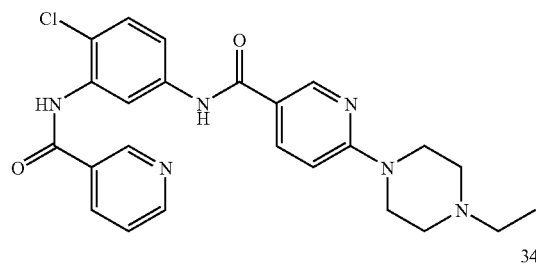
34
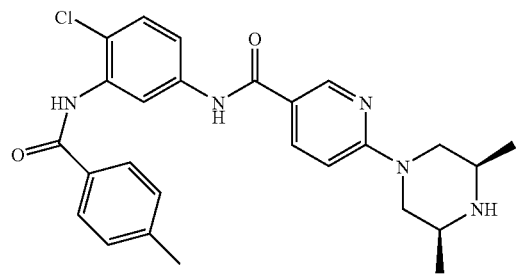
35
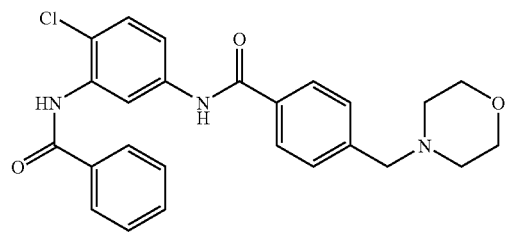
36
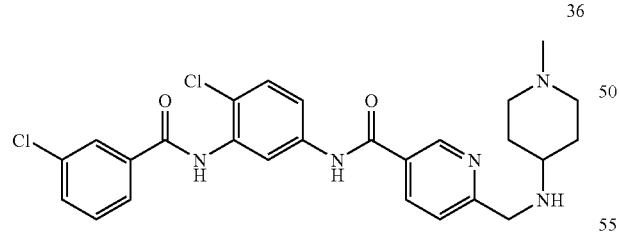
37
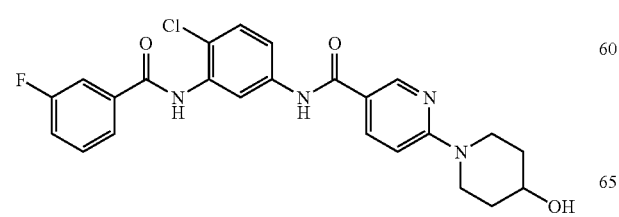
-continued
38
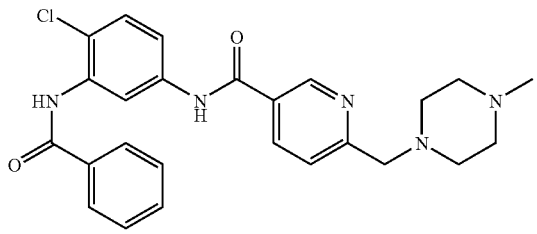
39
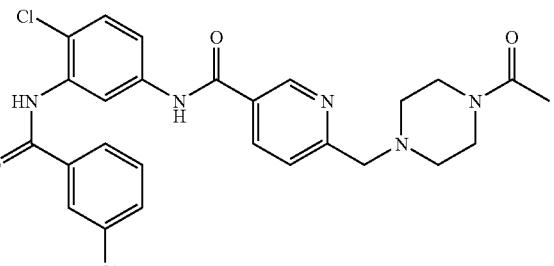
40
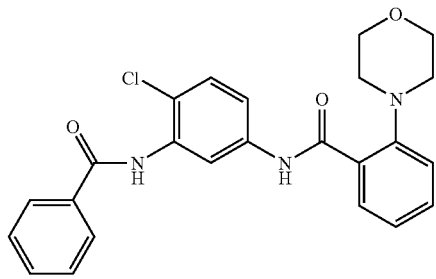
41
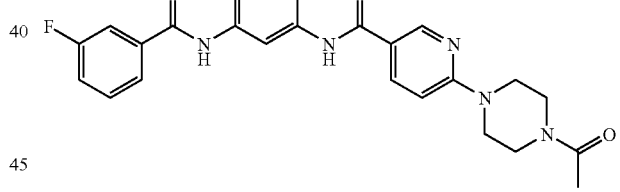
42
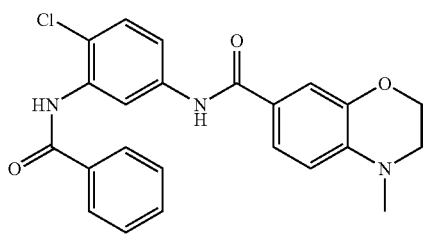
43
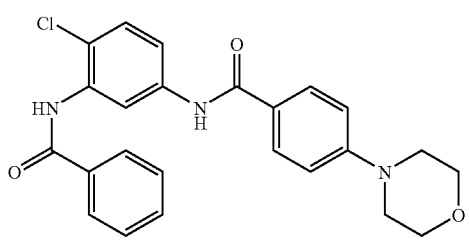

44
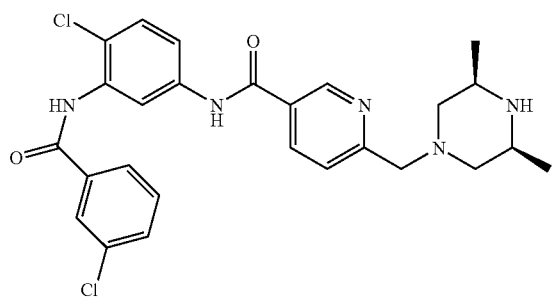
45
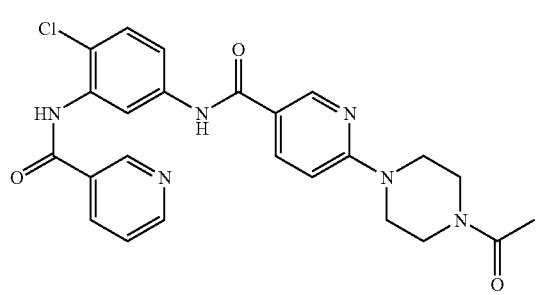
46
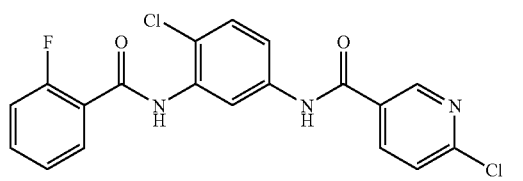
47
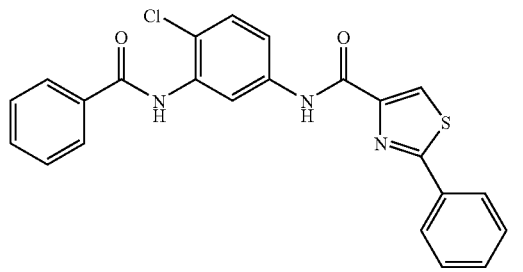
48
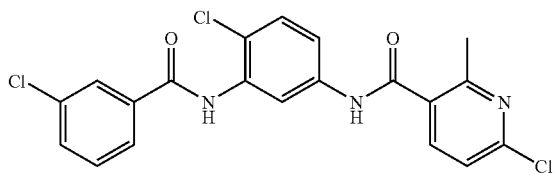
49
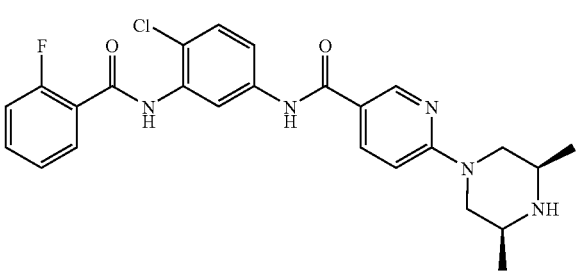
50
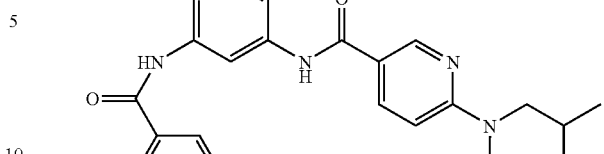
51
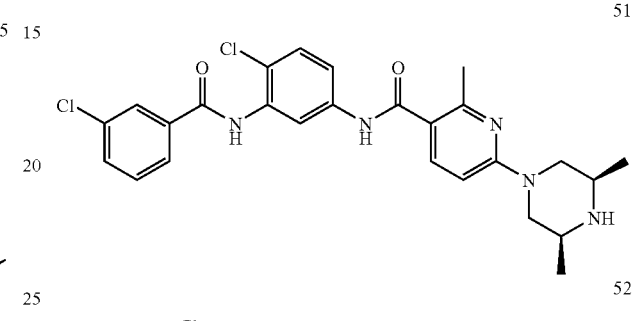
52
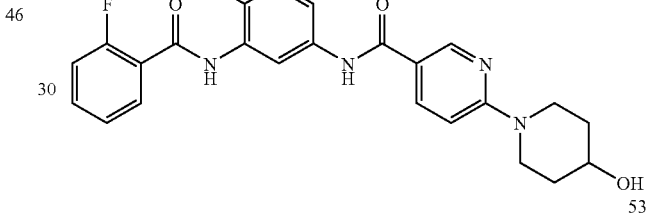
53
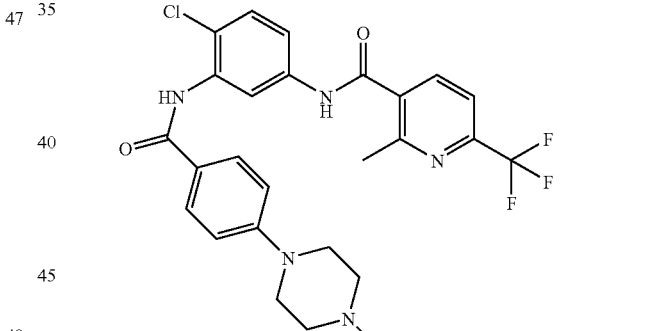
54
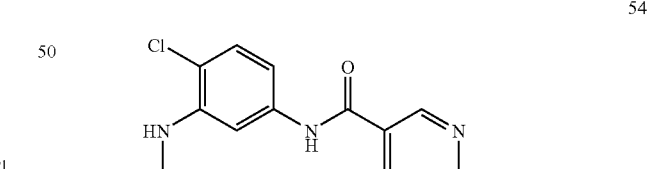
55
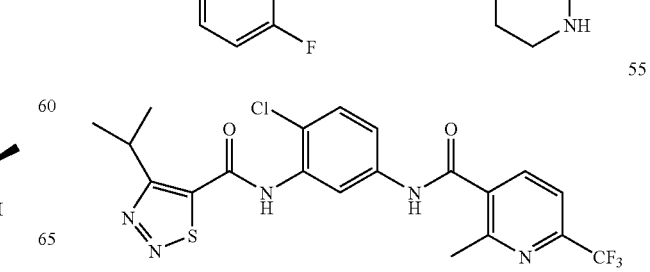

-continued
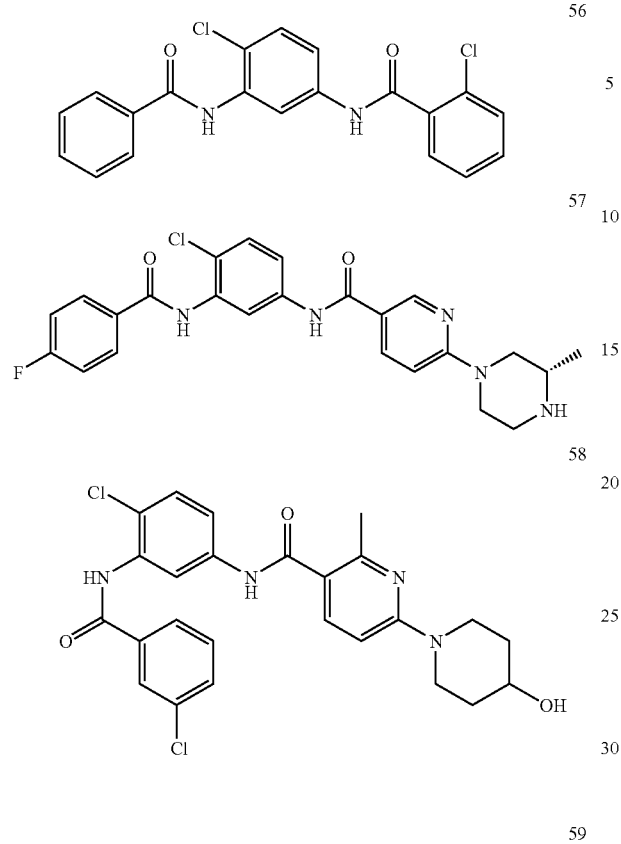
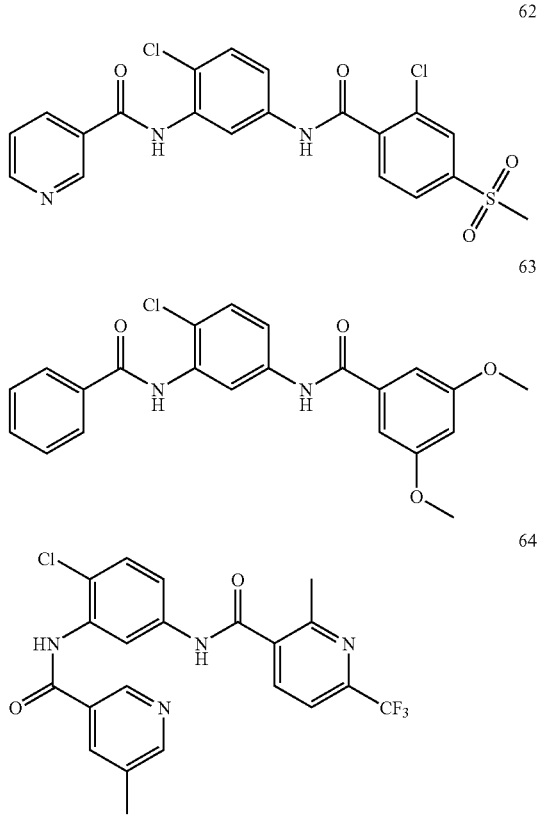
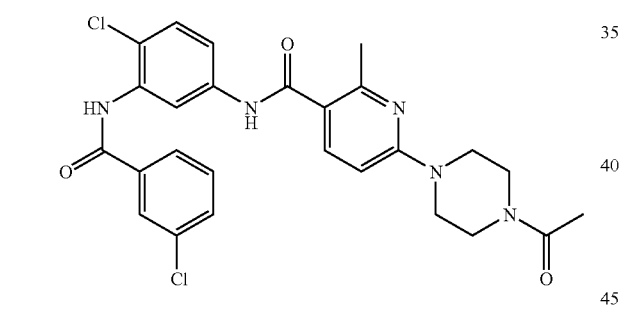
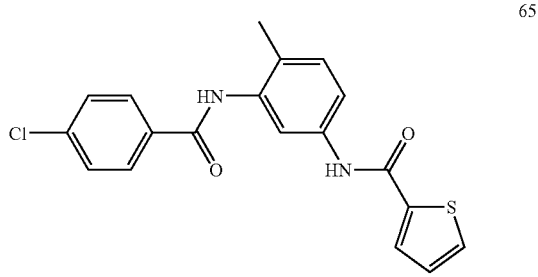
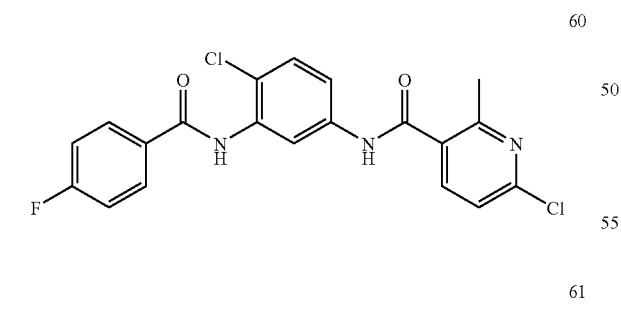
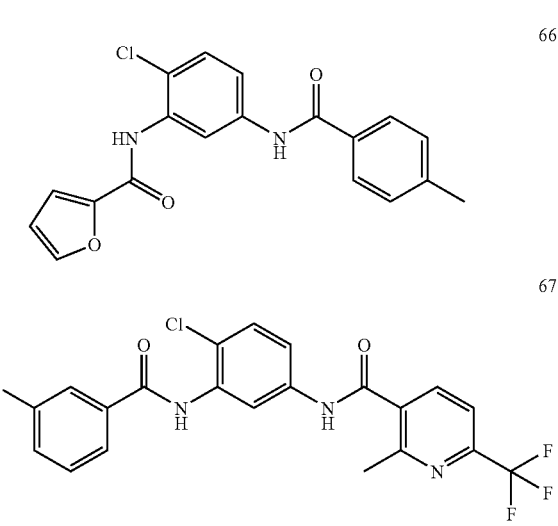

68
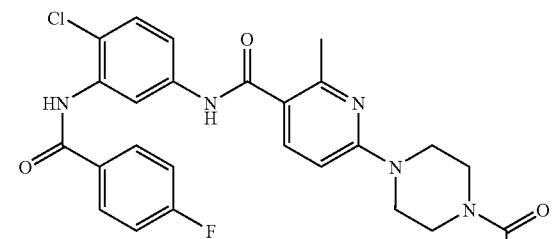
69
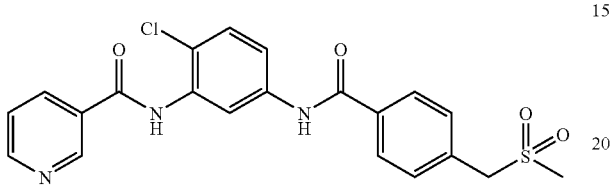
70
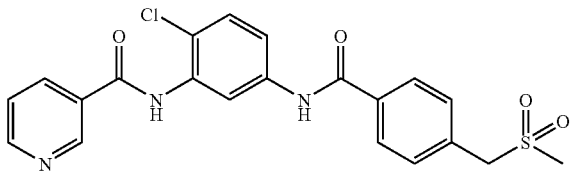
71
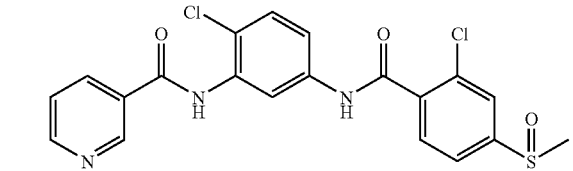
72
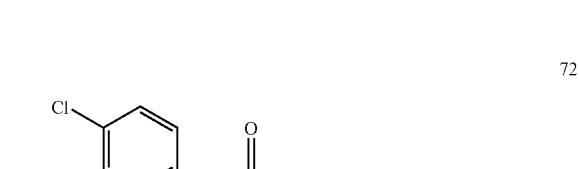
73
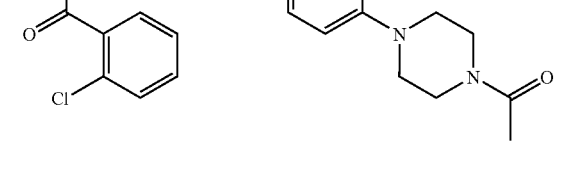
74
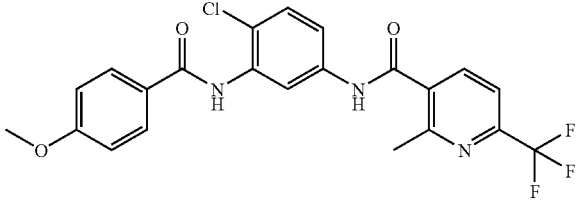
75
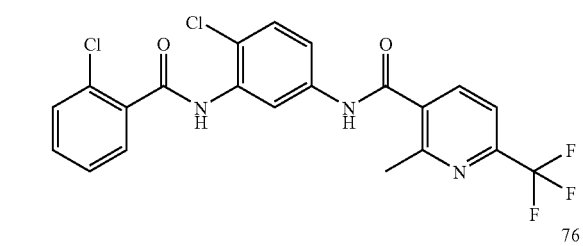
76
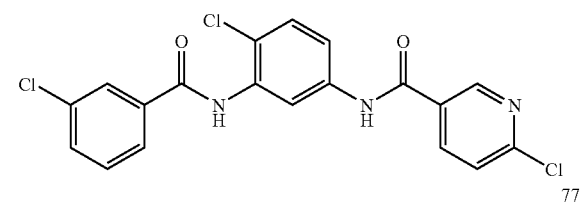
77
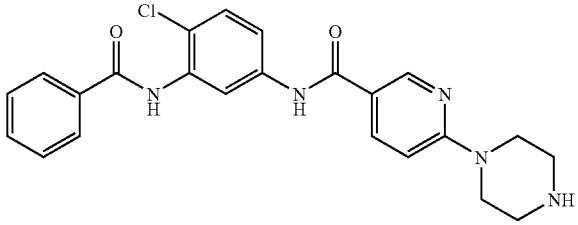
78
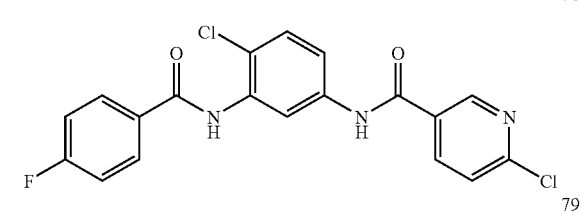
79
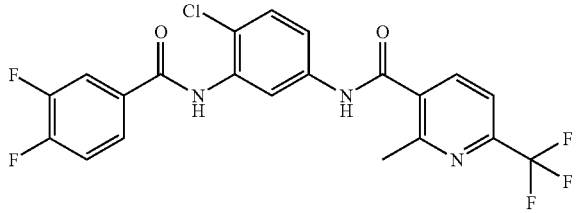
80
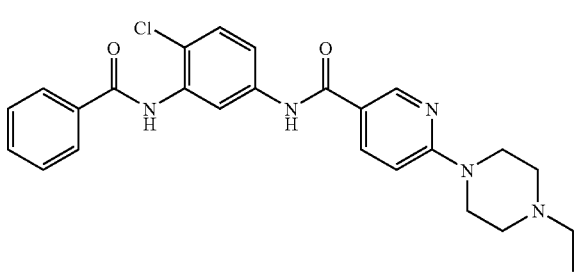

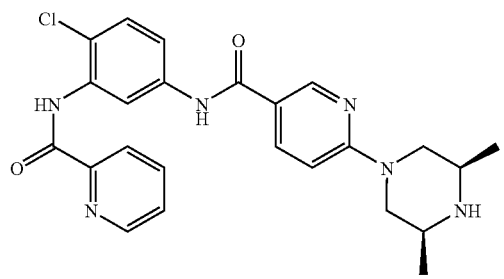
81
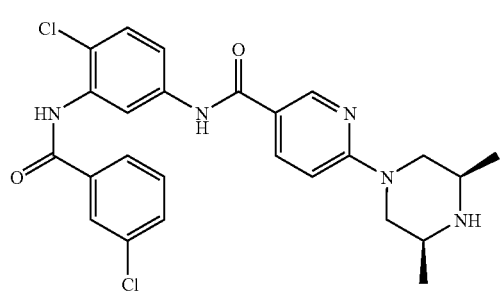
82
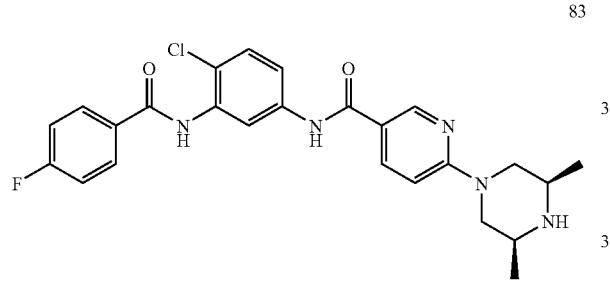
83
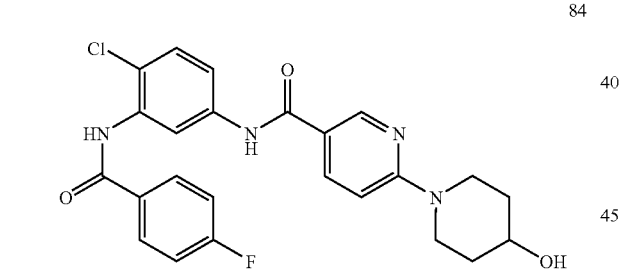
84
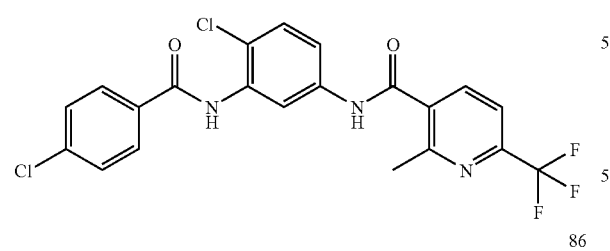
85
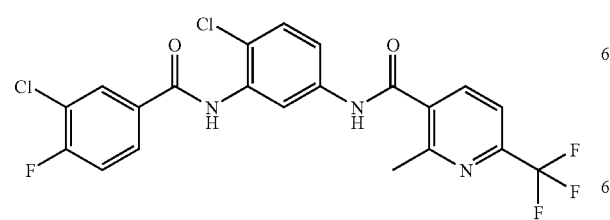
86
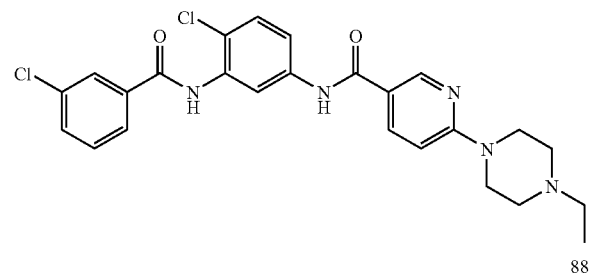
87
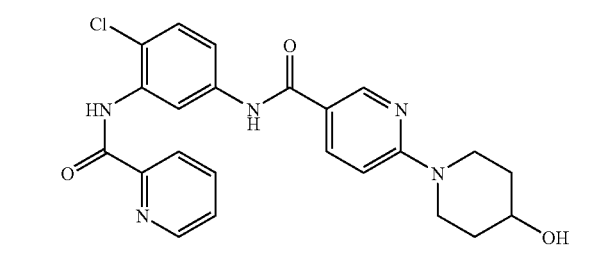
88
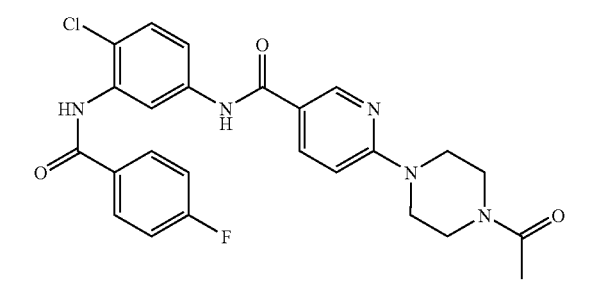
89
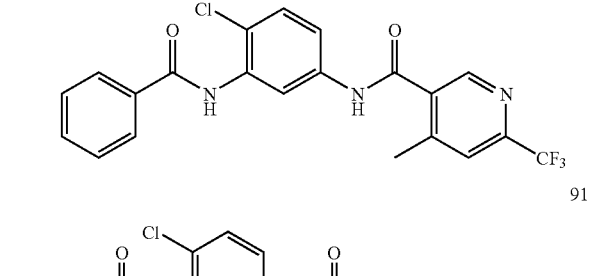
90
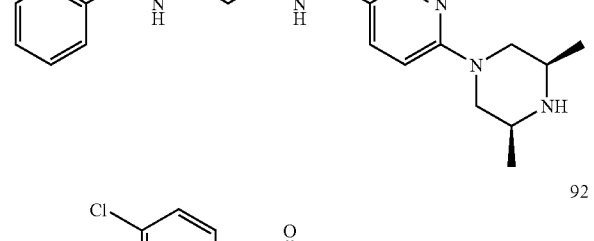
91
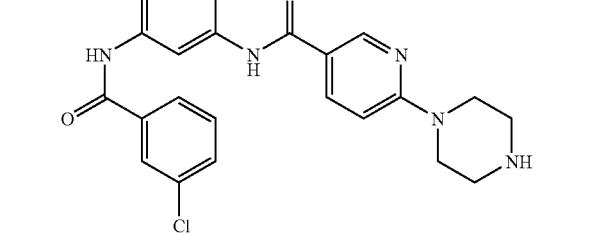
92

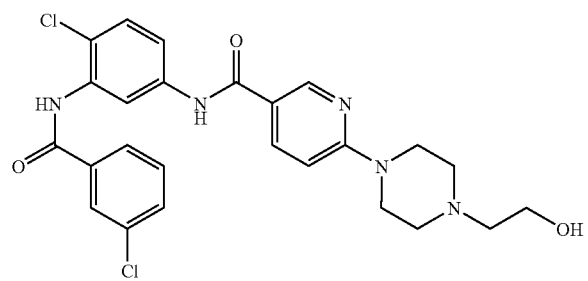
93
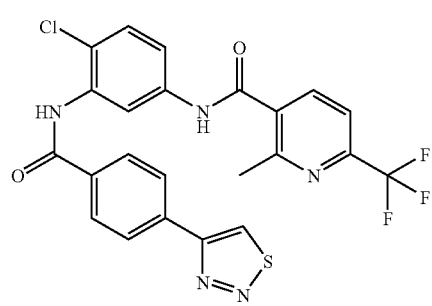
94
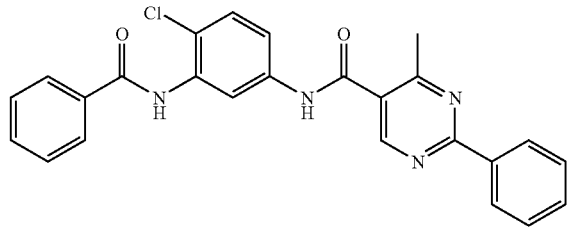
95
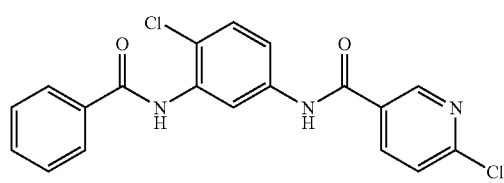
96
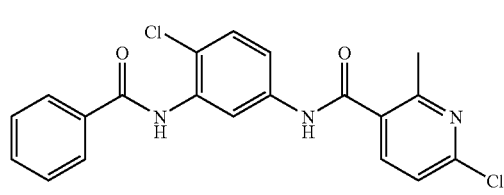
97
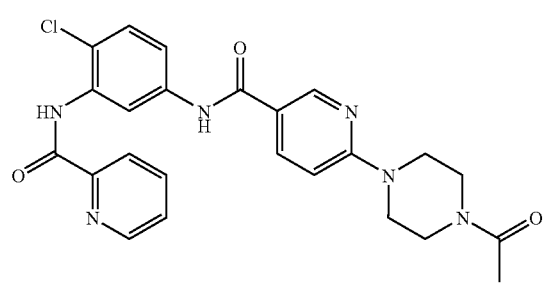
98
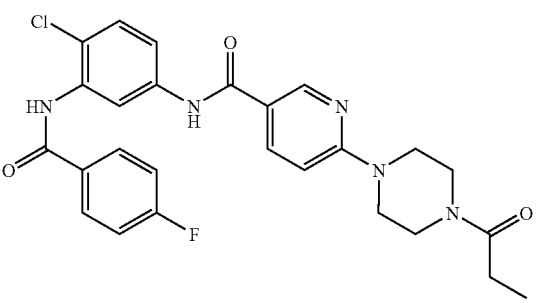
99
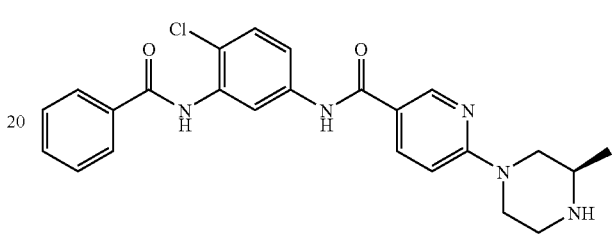
100
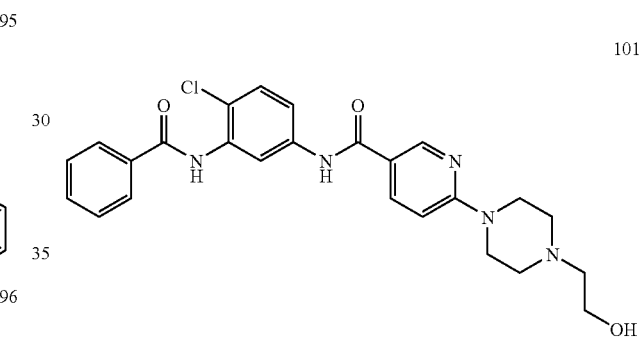
101
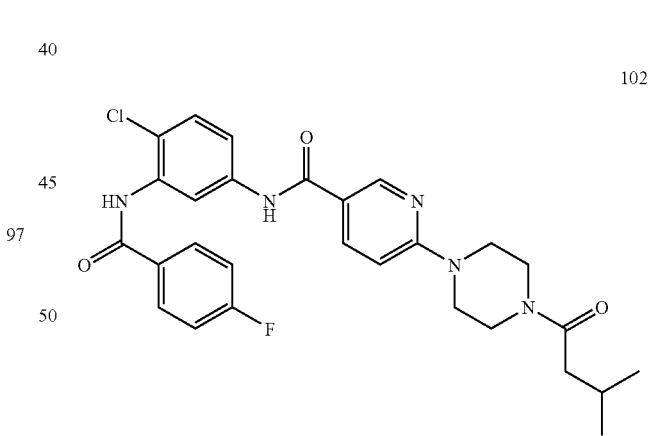
102
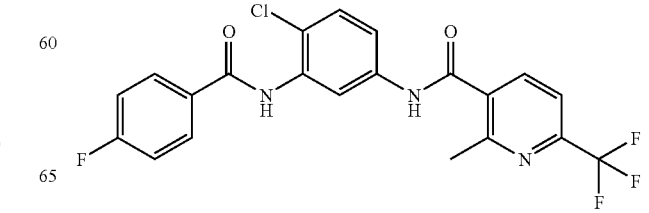
103

-continued

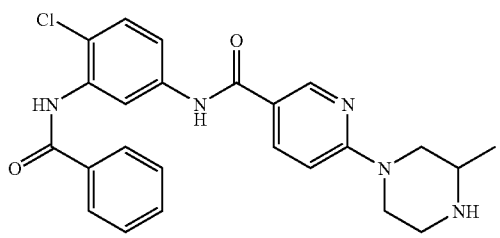
114
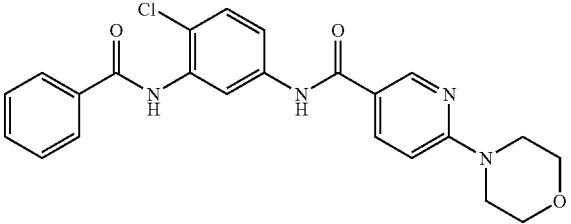
120
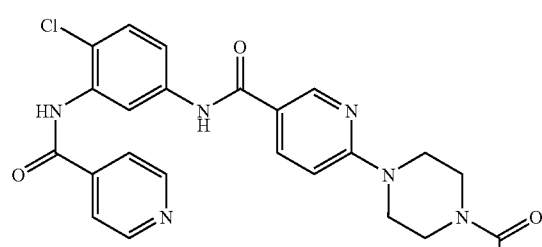
115
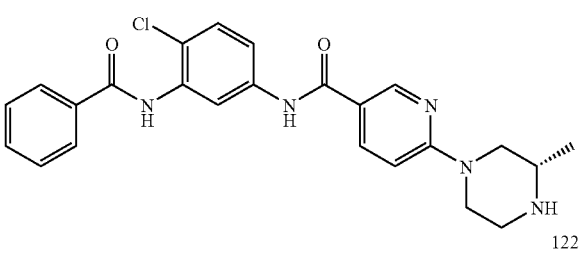
121
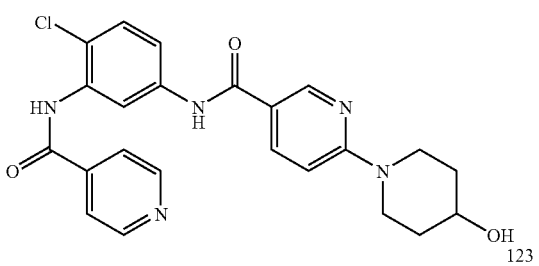
122
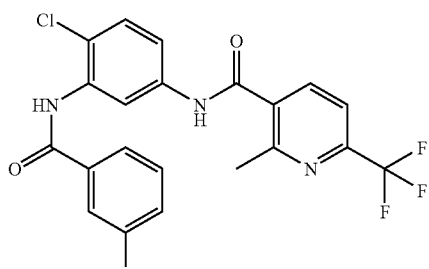
116
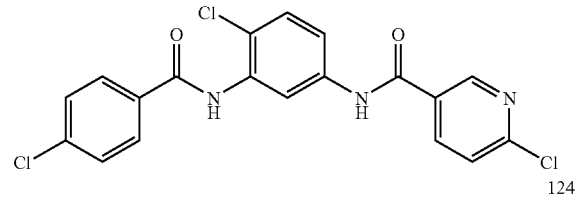
123
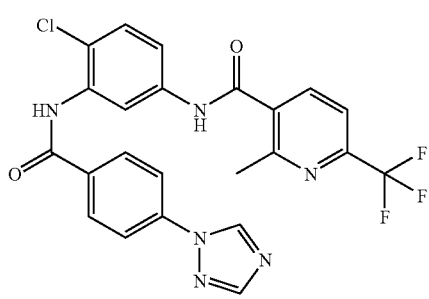
117
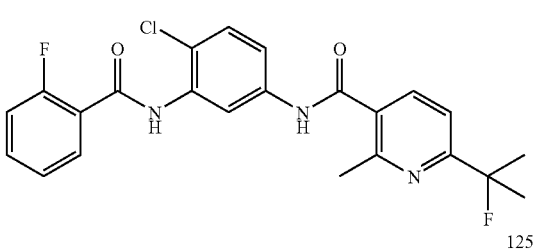
124
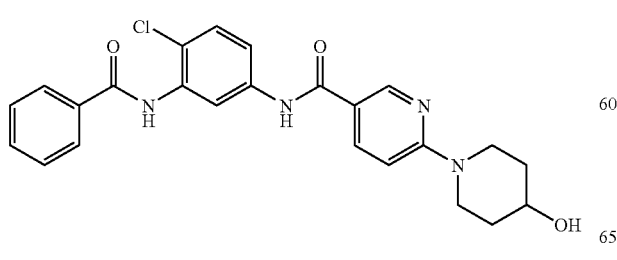
118
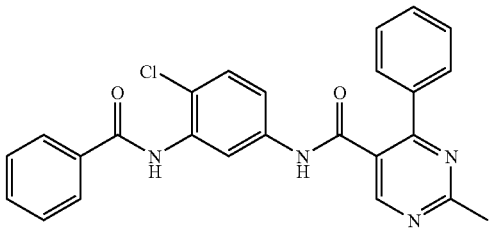
125
119
126

127
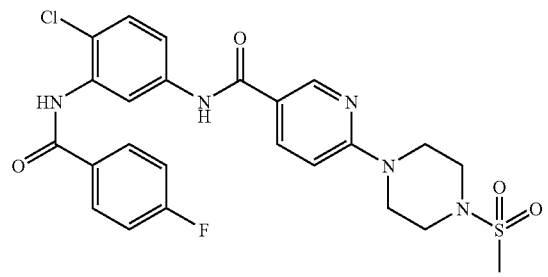
128
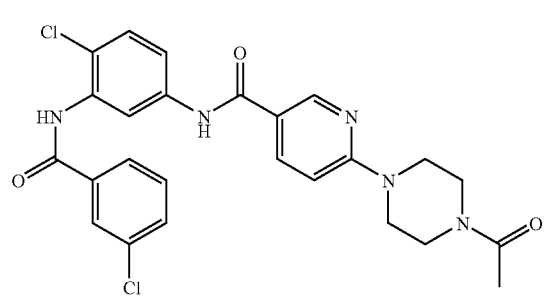
129
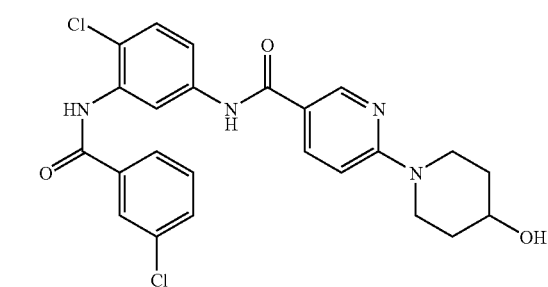
130
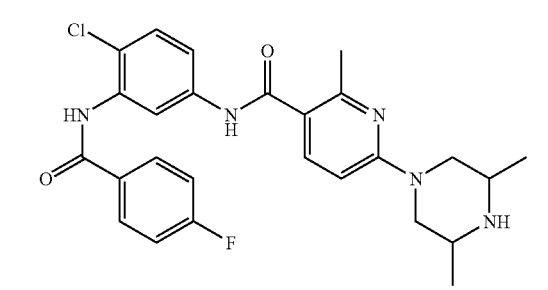
131
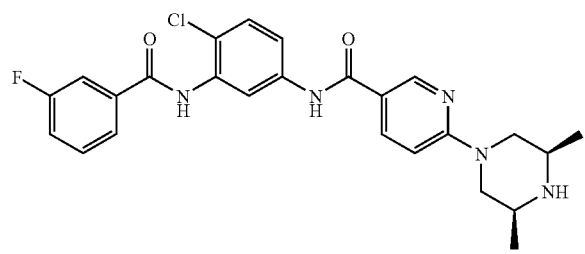
132
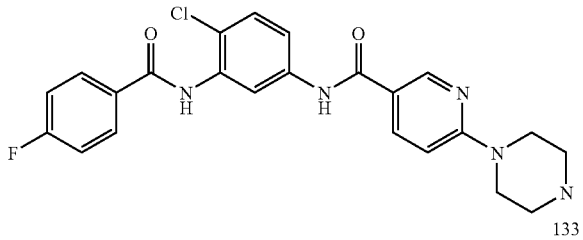
133
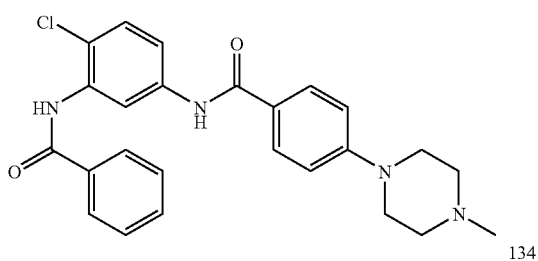
134
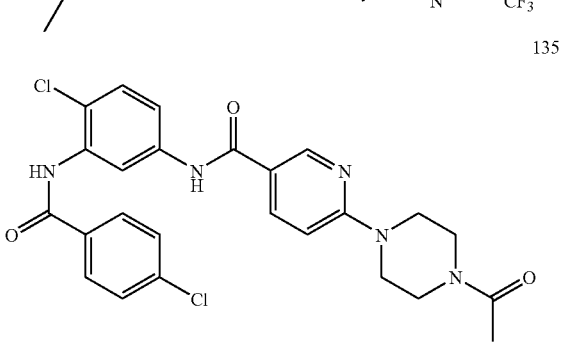
135
136
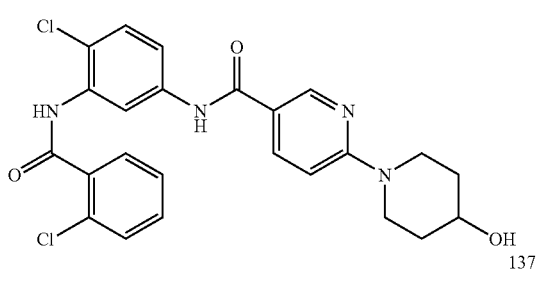
137
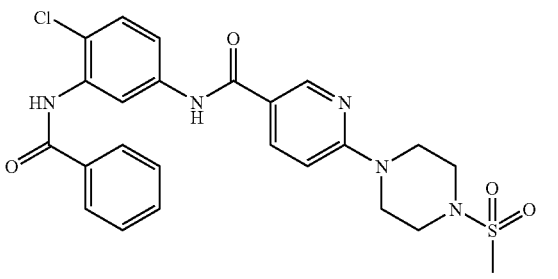
Compounds of the invention are prepared using standard organic synthetic techniques from commercially available starting materials and reagents. It will be appreciated that synthetic procedures employed in the preparation of compounds of the invention will depend on the particular substituents present in a compound and that various protection and deprotection procedures may be required as is standard in organic synthesis. Compounds of the invention may be prepared by coupling the A, B and central rings via established amide bond formation procedures according to the following general scheme 1:

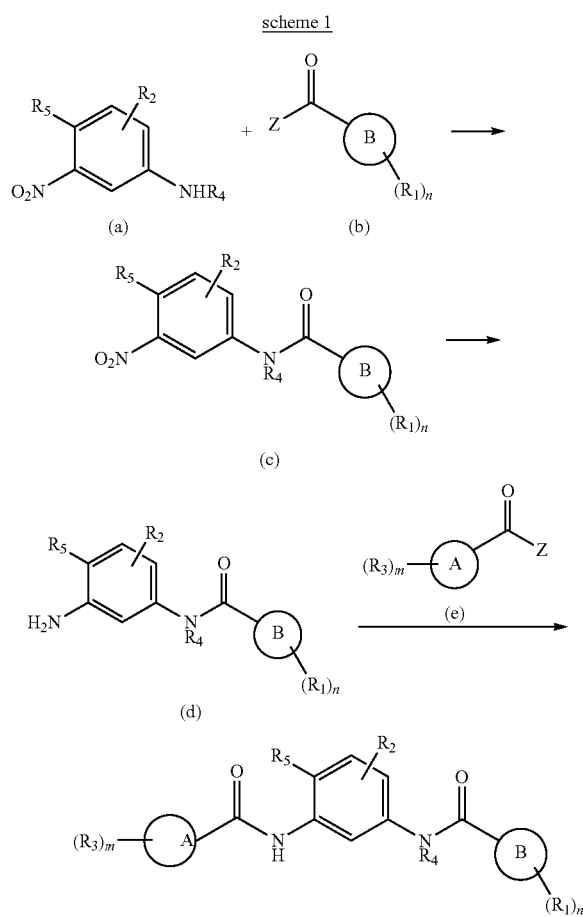

wherein Z is either a halide (such as chloro) or hydroxyl. Nitroaniline (a) is coupled to acid halide or carboxylic acid (b) to give intermediate (c) which is subsequently reduced to give amine (d). Amine (d) is then coupled with acid halide or carboxylic acid (e) to give the final compound.

Compounds of the invention may also be prepared by coupling the rings in an alternate sequence according to general procedure 2:

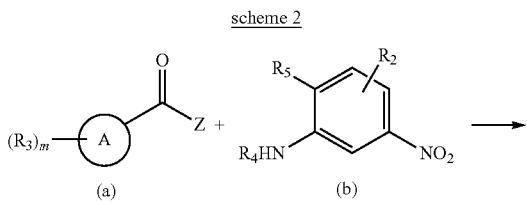

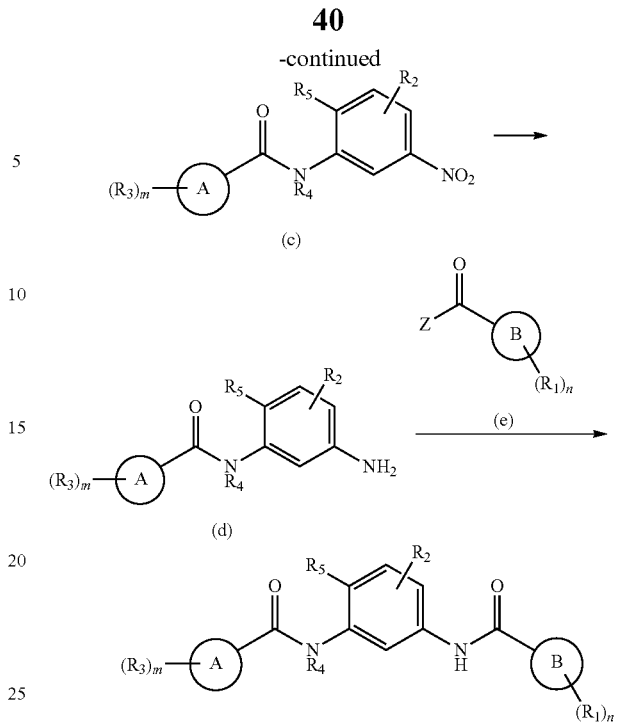

in which nitroaniline (b) is coupled to acid halide or carboxylic acid (a) to give intermediate (c) which is subsequently reduced to give amine (d). Amine (d) is then coupled with acid halide or carboxylic acid (e) to give the final compound.

Compounds of the invention may contain one or more asymmetric carbon atoms. Accordingly, the compounds may exist as diastereomers, enantiomers or mixtures thereof. The syntheses of the compounds may employ racemates, diastereomers or enantiomers as starting materials or as intermediates. Diastereomeric compounds may be separated by chromatographic or crystallization methods. Similarly, enantiomeric mixtures may be separated using the same techniques or others known in the art. Each of the asymmetric carbon atoms may be in the R or S configuration and both of these configurations are within the scope of the invention.

The invention also encompasses prodrugs of the compounds described above. Suitable prodrugs include known amino-protecting and carboxy-protecting groups which are released, for example hydrolyzed, to yield the parent compound under physiologic conditions. A particular class of prodrugs are compounds in which a nitrogen atom in an amino, amidino, aminoalkyleneamino, iminoalkyleneamino or guanidino group is substituted with a hydroxy (OH) group, an alkylcarbonyl (—CO—R) group, an alkoxycarbonyl (—CO—OR), an acyloxyalkyl-alkoxycarbonyl (—CO—O—R—O—CO—R) group where R is a monovalent or divalent group and as defined above or a group having the formula —C(O)—O—CP1P2-haloalkyl, where P1 and P2 are the same or different and are H, lower alkyl, lower alkoxy, cyano, halo lower alkyl or aryl. Prodrug compounds may be prepared by reacting the compounds of the invention described above with an activated acyl compound to bond a nitrogen atom in the compound of the invention to the carbonyl of the activated acyl compound. Suitable activated carbonyl compounds contain a good leaving group bonded to the carbonyl carbon and include acyl halides, acyl amines, acyl pyridinium salts, acyl alkoxides, in particular acyl phenoxides such as p-nitrophenoxy acyl, dinitrophenoxy acyl, fluorophenoxy acyl, and difluorophenoxy acyl. The reactions are generally exothermic and are carried out in inert solvents at reduced temperatures such as −78 to about 50° C. The reactions are usually also carried out in the presence of an inorganic base such as potassium carbonate or sodium bicarbonate, or an organic base such as an amine, including pyridine, TEA, etc. One manner of preparing prodrugs is described in U.S. Ser. No. 08/843,369 filed Apr. 15, 1997 (corresponding to PCT publication WO9846576) the contents of which are incorporated herein by reference in their entirety.

The compounds of the invention inhibit the hedgehog signaling and are useful for the treatment of cancers associated with aberrant hedgehog signaling, for example when Patched fails to, or inadequately, represses Smoothened (Ptc loss-of-function phenotype) and/or when Smoothened is active regardless of Patched repression (Smo gain-of-function phenotype). Examples of such cancer types include basal cell carcinoma, neuroectodermal tumors such as medulloblastoma, meningioma, hemangioma, glioblastoma, pancreatic adenocarcinoma, squamous lung carcinoma, small-cell lung carcinoma, non-small cell lung carcinoma, chondrosarcoma, breast carcinoma, rhabdomyosarcoma, oesophageal cancer, stomach cancer, biliary tract cancer, renal carcinoma, thyroid carcinoma. Compounds of the invention may be administered prior to, concomitantly with, or following administration of other anticancer treatments such as radiation therapy or chemotherapy. Suitable cytostatic chemotherapy compounds include, but are not limited to (i) antimetabolites, such as cytarabine, fludarabine, 5-fluoro-2'-deoxyuridine, gemcitabine, hydroxyurea or methotrexate; (ii) DNA-fragmenting agents, such as bleomycin, (iii) DNA-crosslinking agents, such as chlorambucil, cisplatin, cyclophosphamide or nitrogen mustard; (iv) intercalating agents such as adriamycin (doxorubicin) or mitoxantrone; (v) protein synthesis inhibitors, such as L-asparaginase, cycloheximide, puromycin or diphtheria toxin; (Vi) topoisomerase I poisons, such as camptothecin or topotecan; (vii) topoisomerase II poisons, such as etoposide (VP-16) or teniposide; (viii) microtubule-directed agents, such as colcemid, colchicine, paclitaxel, vinblastine or vincristine; (ix) kinase inhibitors such as flavopiridol, staurosporin, STI571 (CPG 57148B) or UCN-01 (7-hydroxystaurosporine); (x) miscellaneous investigational agents such as thioplatin, PS-341, phenylbutyrate, ET-18-OCH$_3$, or farnesyl transferase inhibitors (L-739749, L-744832); polyphenols such as quercetin, resveratrol, piceatannol, epigallocatechin gallate, theaflavins, flavanols, procyanidins, betulinic acid and derivatives thereof; (xi) hormones such as glucocorticoids or fenretinide; (xii) hormone antagonists, such as tamoxifen, finasteride or LHRH antagonists. In a particular embodiment, compounds of the present invention are coadministered with a cytostatic compound selected from the group consisting of cisplatin, doxorubicin, taxol, taxotere and mitomycin C.

Another class of active compounds which can be used in the present invention are those which are able to sensitize for or induce apoptosis by binding to death receptors ("death receptor agonists"). Such agonists of death receptors include death receptor ligands such as tumor necrosis factor a (TNF-α), tumor necrosis factor β (TNF-β, lymphotoxin-α), LT-β (lymphotoxin-β), TRAIL (Apo2L, DR4 ligand), CD95 (Fas, APO-1) ligand, TRAMP (DR3, Apo-3) ligand, DR6 ligand as well as fragments and derivatives of any of said ligands. In a particular embodiment, the death receptor ligand is TNF-α. In another particular embodiment the death receptor ligand is Apo2L/TRAIL. Furthermore, death receptors agonists comprise agonistic antibodies to death receptors such as anti-CD95 antibody, anti-TRAIL-R1 (DR4) antibody, anti-TRAIL-R2 (DR5) antibody, anti-TRAIL-R3 antibody, anti-TRAIL-R4 antibody, anti-DR6 antibody, anti-TNF-R1 antibody and anti-TRAMP (DR3) antibody as well as fragments and derivatives of any of said antibodies.

For the purpose of sensitizing cells for apoptosis, the compounds of the present invention can be also used in combination with radiation therapy. The phrase "radiation therapy" refers to the use of electromagnetic or particulate radiation in the treatment of neoplasia. Radiation therapy is based on the principle that high-dose radiation delivered to a target area will result in the death of reproducing cells in both tumor and normal tissues. The radiation dosage regimen is generally defined in terms of radiation absorbed dose (rad), time and fractionation, and must be carefully defined by the oncologist. The amount of radiation a patient receives will depend on various consideration including the location of the tumor in relation to other organs of the body, and the extent to which the tumor has spread. Examples of radiotherapeutic agents are provided in, but not limited to, radiation therapy and is known in the art (Hellman, Principles of Radiation Therapy, Cancer, in Principles I and Practice of Oncology, 24875 (Devita et al., 4th ed., vol 1, 1993). Recent advances in radiation therapy include three-dimensional conformal external beam radiation, intensity modulated radiation therapy (IMRT), stereotactic radiosurgery and brachytherapy (interstitial radiation therapy), the latter placing the source of radiation directly into the tumor as implanted "seeds". These newer treatment modalities deliver greater doses of radiation to the tumor, which accounts for their increased effectiveness when compared to standard external beam radiation therapy.

Ionizing radiation with beta-emitting radionuclides is considered the most useful for radiotherapeutic applications because of the moderate linear energy transfer (LET) of the ionizing particle (electron) and its intermediate range (typically several millimeters in tissue). Gamma rays deliver dosage at lower levels over much greater distances. Alpha particles represent the other extreme, they deliver very high LET dosage, but have an extremely limited range and must, therefore, be in intimate contact with the cells of the tissue to be treated. In addition, alpha emitters are generally heavy metals, which limits the possible chemistry and presents undue hazards from leakage of radionuclide from the area to be treated. Depending on the tumor to be treated all kinds of emitters are conceivable within the scope of the present invention. Furthermore, the present invention encompasses types of non-ionizing radiation like e.g. ultraviolet (UV) radiation, high energy visible light, microwave radiation (hyperthermia therapy), infrared (IR) radiation and lasers. In a particular embodiment of the present invention UV radiation is applied.

Compounds of the invention inhibit angiogenesis and are therefore useful in the treatment of diseases or conditions mediated by angiogenesis such as tumors, in particular solid tumors such as colon, lung, pancreatic, ovarian, breast and glioma. Furthermore, compounds of the invention are useful for treating macular degeneration e.g. wet age-related macular degeneration. Compounds of the invention are also useful for treating inflammatory/immune diseases such as Crohn's, inflammatory bowel disease, Sjogren's syndrome, asthma, organ transplant rejection, systemic lupus erythmatosis, rheumatoid arthritis, psoriatic arthritis, psoriasis and multiple sclerosis. Compounds of the invention are also useful as a depilatory.

The invention also includes pharmaceutical compositions or medicaments containing the compounds of the invention and a therapeutically inert carrier, diluent or excipient, as well as methods of using the compounds of the invention to prepare such compositions and medicaments. Typically, the compounds of the invention used in the methods of the invention are formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but may range from about 3 to about 8. A particular formulation is an acetate buffer at pH 5. The compounds for use herein may be in a sterile formulation. The compound may be stored as a solid composition, although lyophilized formulations or aqueous solutions are acceptable.

The composition of the invention will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to decrease hedgehog pathway signaling or else is the minimum amount necessary to cause reduction in size, volume or mass of a tumor that is responsive to hedgehog signaling, or a reduction in the increase in size, volume or mass of such a tumor relative to the increase in the absence of administering the compound of the invention. Alternatively "effective amount" of the compound means the amount necessary to reduce the number of malignant cells or the rate in increase of the number of malignant cells. Alternatively, "effective amount" is the amount of the compound of the invention required to increase survival of patients afflicted with an anti-hedgehog pathway sensitive tumor. Such amount may be below the amount that is toxic to normal cells, or the mammal as a whole. With respect to non-malignant indications, "effective amount" means the amount of compound of the invention required to decrease severity of the particular indication or symptoms thereof.

Generally, the initial pharmaceutically effective amount of the compound of the invention administered parenterally per dose will be in the range of about 0.01 to about 100 mg/kg, for example about 0.1 to about 20 mg/kg of patient body weight per day, for example about 0.3 to about 15 mg/kg/day. Oral unit dosage forms, such as tablets and capsules, may contain from about 25 to about 1000 mg of the compound of the invention.

The compound of the invention may be administered by any suitable means, including oral, topical, transdermal, parenteral, subcutaneous, rectal, intraperitoneal, intrapulmonary, and intranasal, and, if desired for local treatment, intralesional administration. Parenteral infusions include intramuscular, intravenous, intraarterial, intraperitoneal, or subcutaneous administration. An example of a suitable oral dosage form is a tablet containing about 25 mg, 50 mg, 100 mg, 250 mg, or 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An aerosol formulation can be prepared by dissolving the compound, for example 5-400 mg, of the invention in a suitable buffer solution, e.g. a phosphate buffer, adding a tonicifier, e.g. a salt such sodium chloride, if desired. The solution is typically filtered, e.g. using a 0.2 micron filter, to remove impurities and contaminants. Topical formulations include ointments, creams, lotions, powders, solutions, pessaries, sprays, aerosols and capsules. Ointments and creams may be formulated with an aqueous or oily base with the addition of suitable thickening and/or gelling agents and/or solvents. Such bases may include water and/or an oil such a liquid paraffin or a vegetable oil such as arachis oil or castor oil or a solvent such as a polyethylene glycol. Thickening agents which may be used include soft paraffin, aluminum stearate, cetostearyl alcohol, polyethylene glycols, microcrystalline wax and beeswax. Lotions may be formulated with an aqueous or oily base and may contain one or more emulsifying agents, stabilizing agents, dispersing agents, suspending agents or thickening agents. Powders for external application may be formed with the aid of any suitable powder base e.g. talc, lactose or starch. Drops may be formulated with an aqueous or non-aqueous base also comprising one or more dispersing agents, solubilizing agents or suspending agents.

EXAMPLES

The invention will be more fully understood by reference to the following examples. They should not, however, be construed as limiting the scope of the invention. Abbreviations used herein are as follows:
BuOH: butanol;
DIPEA: diisopropylethylamine;
DMA: N,N-dimethylacetamide;
DMAP: 4-dimethylaminopyridine;
DME: 1,2-dimethoxyethane;
DMF: dimethylformamide;
EDC: 1-ethyl-3-(3-dimethylaminopropyl)carbodiimide;
HATU: O-(7-Azobenzotriazol-1-yl)-1,1,3,3-tetramethyluronium hexafluorophosphate;
HPLC: high pressure liquid chromatography
MPLC: medium pressure liquid chromatography
NBS: N-Bromosuccinimide;
TEA: Triethylamine;
TASF: tris(dimethylamino)sulfonium difluorotrimethylsilicate;
THF: tetrahydrofuran;
EtOH: Ethanol;
MeOH: Methanol;
☐L: microliter All reagents were obtained commercially unless otherwise noted. Reactions were performed using oven-dried glassware under an atmosphere of nitrogen. Air and moisture sensitive liquids and solutions were transferred via syringe or stainless steel cannula. Organic solutions were concentrated under reduced pressure (ca. 15 mm Hg) by rotary evaporation. Unless otherwise noted all solvents used were obtained commercially. Chromatographic purification of products was accomplished by use of an Isco CombiFlash Companion and media. Reaction times are given for illustration only. The course of reactions was followed by thin-layer chromatography (TLC) and liquid chromatography-mass spectrometry (LC-MS). Thin-layer chromatography (TLC) was performed on EM Science silica gel 60 $F_{254}$ plates (250 µm). Visualization of the developed chromatogram was accomplished by fluorescence quenching. LC-MS were acquired with a Shimadzu 10 AD LC on a Phenomenex column (50×4.6 mm, 5 µm) operating at 3 mL/min. A Shimadzu SPD-10A detector monitoring at 214 and 254 nm was used. Single quadrupole mass spectrometry was performed on an Applied Biosystems mass spectrometer. Nuclear magnetic resonance (NMR)

spectra were acquired on a Varian Inova spectrometer operating at 400 MHz for $^1$H and are referenced internally to tetramethylsilane (TMS) in parts per million (ppm). Data for $^1$H NMR are recorded as follows: chemical shift (δ, ppm), multiplicity (s, singlet; bs, broad singlet; d, doublet; t, triplet; q, quartet; quint, quintet; sext, sextet; hept, heptet; m, multiplet; bm, broad multiplet), and integration. The structure and purity of all final products were assessed by at least one of the following techniques: LC-MS, NMR, TLC.

Example 1

General Procedures

1. Amide Bond Formation with Acid Chlorides volume of EtOAc. This mixture was washed with aq. NaHCO$_3$, then aq. NaCl and dried (Na$_2$SO$_4$) and concentrated.

2. Amide Bond Formation with HATU

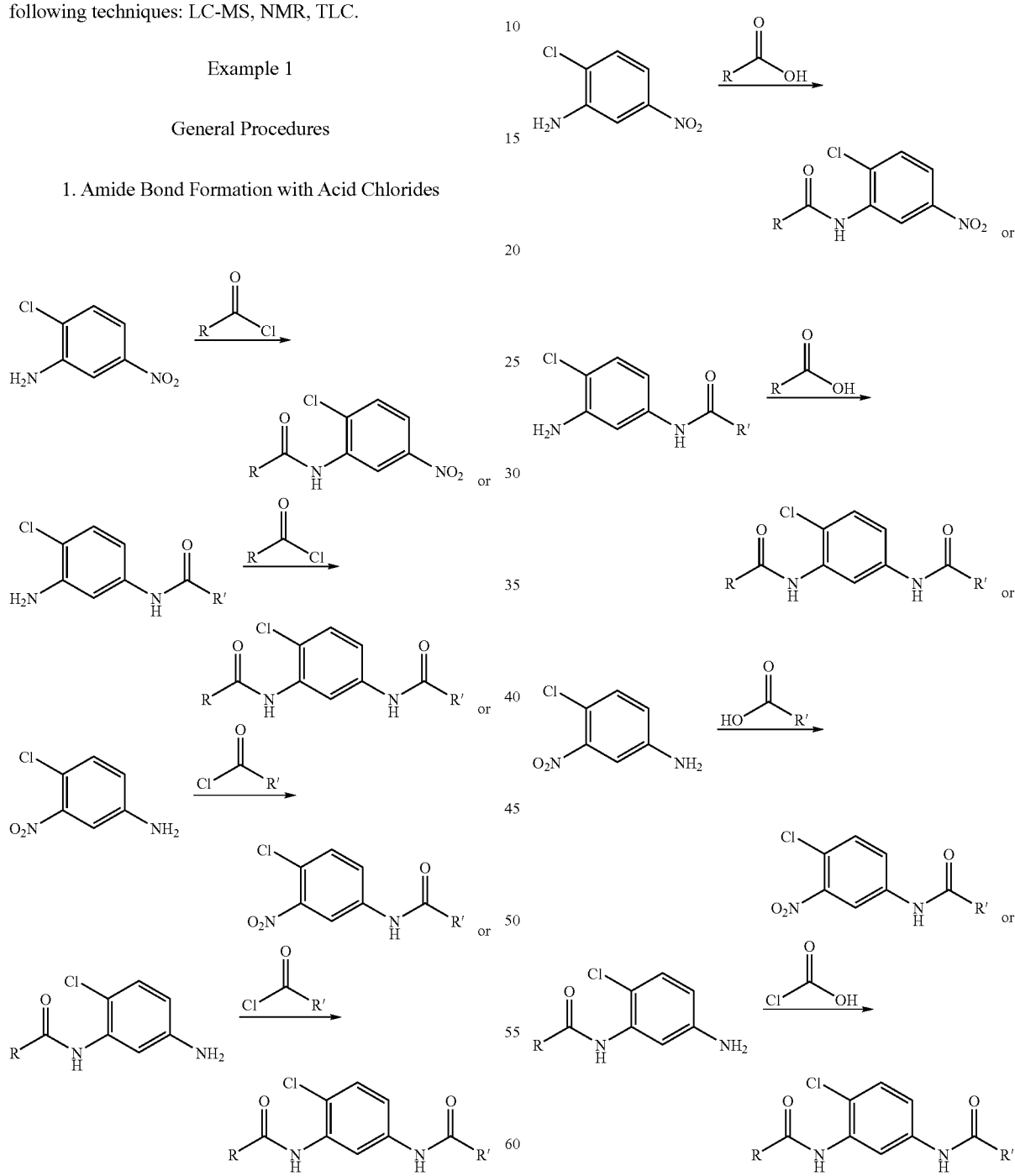

Acid chloride (1.1 eq.) was added to a solution of aniline (1.0 eq.) and either TEA or pyridine (1.5-2.0 eq.) in DMF at the indicated temperature. The solution was stirred for 0.5-15 hours. At rt the reaction mixture was diluted with a large Aniline (1.0 eq.) was added to a stirred mixture of carboxylic acid (1.1 eq.), HATU (1.1 eq.) and DIPEA (2.0 eq.) in DMF (0.25 to 0.5 M). The reaction was stirred at rt (2-15 hours) then diluted with a large volume of EtOAc. The reaction mixture was washed with aq. NaHCO$_3$, then aq. NaCl and dried (Na$_2$SO$_4$) and concentrated.

3. Addition of Amines to 2-chloropyridine or 2-chloro-6-methyl-pyridine

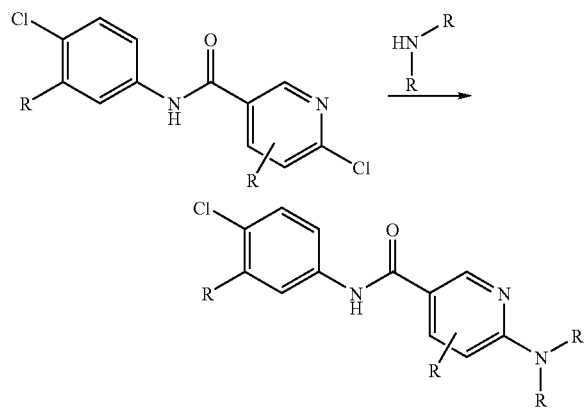

To a solution of the relevant pyridine (1.0 eq.) in n-BuOH was added secondary amine (3-5 eq.). The reaction mixture was heated at 165-170 C for 10 min to 2 hr in a sealed tube. The BuOH was removed under reduced pressure. The crude residue was purified by reverse phase HPLC to afford the desired product.

4. Tin(II) Chloride Reduction of Nitrobenzene Intermediate

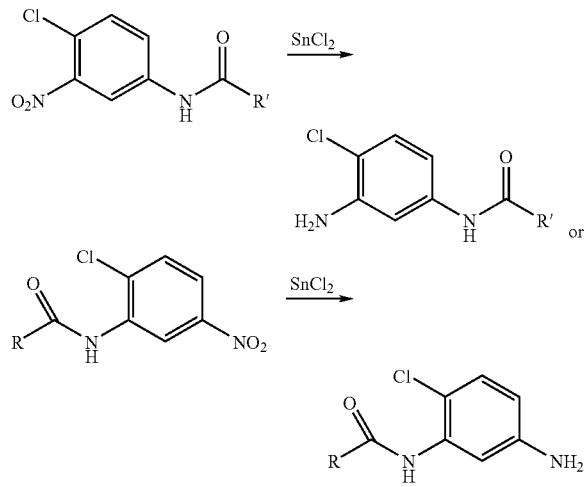

To a stirred solution of the appropriate nitrobenzene intermediate (1 mmol.) in either EtOH or EtOAc (0.25 M) was added portion wise Tin(II) Chloride (3.0 eq.). The reaction was heated at 78 C for 1-3 hours then equilibrated to room temperature. Next, TEA (10 eq.) was added to the reaction. The resulting slurry was concentrated on a rotary evaporator to remove the organic solvent and then triturated with a large volume of EtOAc. The liquid and solid were separated by vacuum filtration and the filtrate was washed with aq. NaHCO$_3$, then aq. NaCl and dried (Na$_2$SO$_4$) and concentrated.

5. Addition of Amines and Cyclic Amines to N-(3-benzamido-4-chlorophenyl)-6-(bromomethyl)nicotinamide

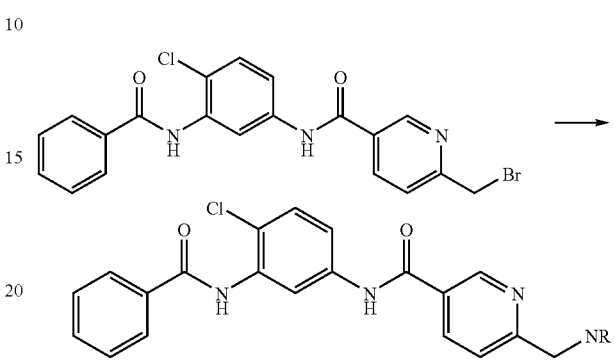

To a stirred solution of N-(3-benzamido-4-chlorophenyl)-6-(bromomethyl)nicotinamide (0.11 mmol, 1.0 eq.) in 200 μL of DMSO was added cyclic amine (1.1 eq,). The reaction was stirred overnight at room temperature to give the desired product.

Example 2

N-(4-chloro-3-nitrophenyl)-2-methyl-6-(trifluoromethyl)nicotinamide 3-nitro-4-chloroaniline (Aldrich), (11.6 mmol) was used in general procedure 1 with 2-methyl-6-(trifluoromethyl)nicotinyl chloride (12.7 mmol). The product was purified by silica gel chromatography (40% EtOAc/Hex) to give N-(4-chloro-3-nitrophenyl)-2-methyl-6-(trifluoromethyl)nicotinamide as a tan solid. MS (Q1) 360 (M)+

Example 3

N-(3-amino-4-chlorophenyl)-2-methyl-6-(trifluoromethyl)nicotinamide

N-(4-chloro-3-nitrophenyl)-2-methyl-6-(trifluoromethyl)nicotinamide (11.42 mmol) was used in general procedure 4 to give N-(3-amino-4-chlorophenyl)-2-methyl-6-(trifluoromethyl)nicotinamide as a white solid. MS (Q1) 330.0 (M)+

Example 4

N-(3-benzamido-4-chlorophenyl)-4-methyl-6-(trifluoromethyl)nicotinamide

N-(3-amino-4-chlorophenyl)-2-methyl-6-(trifluoromethyl)nicotinamide (0.376 mmol) was used in general procedure 1 with benzoyl chloride (0.30 mmol). The product was purified by RP-HPLC to give N-(3-benzamido-4-chlorophenyl)-4-methyl-6-(trifluoromethyl)nicotinamide. MS (Q1) 433.1 (M)+

Example 5

N-(4-chloro-3-(2-chlorobenzamido)phenyl)-2-methyl-6-(trifluoromethyl)-nicotinamide N-(3-amino-4-chlorophenyl)-2-methyl-6-(trifluoromethyl)nicotinamide (0.182 mmol) was used in general procedure 1 with 2-chlorobenzoyl chloride (0.228 mmol). The product was purified by RP-HPLC to give N-(4-chloro-3-(2-chlorobenzamido)phenyl)-2-methyl-6-(trifluoromethyl)-nicotinamide. MS (Q1) 469 (M)+

Example 6

N-(4-chloro-3-(3-chlorobenzamido)phenyl)-2-methyl-6-(trifluoromethyl)-nicotinamide N-(3-amino-4-chlorophenyl)-2-methyl-6-(trifluoromethyl)nicotinamide (0.182 mmol) was used in general procedure 1 with 3-chlorobenzoyl chloride (0.228 mmol). The product was purified by RP-HPLC to give N-(4-chloro-3-(3-chlorobenzoamido)phenyl)-2-methyl-6-(trifluoromethyl)-nicotinamide. MS (Q1) 469 (M)+

Example 7

N-(4-chloro-3-(4-chlorobenzamido)phenyl)-2-methyl-6-(trifluoromethyl)-nicotinamide N-(3-amino-4-chlorophenyl)-2-methyl-6-(trifluoromethyl)nicotinamide (0.182 mmol) was used in general procedure 1 with 4-chlorobenzoyl chloride (0.228 mmol). The product was purified by RP-HPLC to give N-(4-chloro-3-(4-chlorobenzoamido)phenyl)-2-methyl-6-(trifluoromethyl)-nicotinamide. MS (Q1) 469 (M)+

Example 8

N-(4-chloro-3-(2-fluorobenzamido)phenyl)-2-methyl-6-(trifluoromethyl)-nicotinamide N-(3-amino-4-chlorophenyl)-2-methyl-6-(trifluoromethyl)nicotinamide (0.15 mmol) was used in general procedure 2 with 2-fluorobenzoic acid (0.167 mmol). The product was purified by RP-HPLC to give N-(4-chloro-3-(2-fluorobenzoamido)phenyl)-2-methyl-6-(trifluoromethyl)-nicotinamide. MS (Q1) 452.3 (M)+

Example 9

N-(4-chloro-3-(3-fluorobenzamido)phenyl)-2-methyl-6-(trifluoromethyl)-nicotinamide N-(3-amino-4-chlorophenyl)-2-methyl-6-(trifluoromethyl)nicotinamide (0.15 mmol) was used in general procedure 2 with 3-fluorobenzoic acid (0.167 mmol). The product was purified by RP-HPLC to give N-(4-chloro-3-(3-fluorobenzamido)phenyl)-2-methyl-6-(trifluoromethyl)-nicotinamide. MS (Q1) 452.1 (M)+

Example 10

N-(4-chloro-3-(4-fluorobenzamido)phenyl)-2-methyl-6-(trifluoromethyl)-nicotinamide N-(3-amino-4-chlorophenyl)-2-methyl-6-(trifluoromethyl)nicotinamide (0.15 mmol) was used in general procedure 2 with 4-fluorobenzoic acid (0.167 mmol). The product was purified by RP-HPLC to give N-(4-chloro-3-(4-fluorobenzamido)phenyl)-2-methyl-6-(trifluoromethyl)-nicotinamide. MS (Q1) 452.0 (M)+

Example 11

N-(4-chloro-3-(3,4-difluorobenzamide)phenyl)-2-methyl-6-(trifluoromethyl)-nicotinamide N-(3-amino-4-chlorophenyl)-2-methyl-6-(trifluoromethyl)nicotinamide (0.15 mmol) was used in general procedure 2 with 3,4-difluorobenzoic acid (0.167 mmol). The product was purified by RP-HPLC to give N-(4-chloro-3-(3,4-difluorobenzamide)phenyl)-2-methyl-6-(trifluoromethyl)-nicotinamide. MS (Q1) 470.3 (M)+

Example 12

N-(4-chloro-3-(3-chloro-4-fluorobenzamido)phenyl)-2-methyl-6-(trifluoromethyl)-nicotinamide N-(3-amino-4-chlorophenyl)-2-methyl-6-(trifluoromethyl)nicotinamide (0.15 mmol) was used in general procedure 2 with 3-chloro-4-fluorobenzoic acid (0.167 mmol). The product was purified by RP-HPLC to give N-(4-chloro-3-(3-chloro-4-fluorobenzamido)phenyl)-2-methyl-6-(trifluoromethyl)nicotinamide. MS (Q1) 486.1 (M)+

Example 13

N-(4-chloro-3-(2-morpholinobenzamido)phenyl)-2-methyl-6-(trifluoromethyl)-nicotinamide N-(3-amino-4-chlorophenyl)-2-methyl-6-(trifluoromethyl)nicotinamide (0.15 mmol) was used in general procedure 2 with 2-morpholinobenzoic acid (0.167 mmol). The product was purified by RP-HPLC to give N-(4-chloro-3-(2-morpholinobenzamido)phenyl)-2-methyl-6-(trifluoromethyl)-nicotinamide. MS (Q1) 519.3 (M)+

Example 14

N-(4-chloro-3-(4-(4-methylpiperazin-1-yl)benzamido)phenyl)-2-methyl-6-(trifluoromethyl)nicotinamide N-(3-amino-4-chlorophenyl)-2-methyl-6-(trifluoromethyl)nicotinamide (0.15 mmol) was used in general procedure 2 with 4-(4-methylpiperazin-1-yl)benzoic acid (0.167 mmol). The product was purified by RP-HPLC to give N-(4-chloro-3-(4-(4-methylpiperazin-1-yl)benzamido)phenyl)-2-methyl-6-(trifluoromethyl)nicotinamide. MS (Q1) 532.0 (M)+

Example 15

N-(4-chloro-3-(4-methoxybenzamido)phenyl)-2-methyl-6-(trifluoromethyl)-nicotinamide N-(3-amino-4-chlorophenyl)-2-methyl-6-(trifluoromethyl)nicotinamide (0.15 mmol) was used in general procedure 2 with 4-methoxybenzoic acid (0.167 mmol). The product was purified by RP-HPLC to give N-(4-chloro-3-(4-(4-methoxybenzamido)phenyl)-2-methyl-6-(trifluoromethyl)-nicotinamide. MS (Q1) 464.1 (M)+

Example 16

N-(3-(4-(1,2,3-thiadiazol-4-yl)benzamido)-4-chlorophenyl)-2-methyl-6-(trifluoromethyl)nicotinamide N-(3-amino-4-chlorophenyl)-2-methyl-6-(trifluoromethyl)nicotinamide (0.15 mmol) was used in general procedure 2 with 4-(1,2,3-thiadiazol-4-yl)benzoic acid (0.167 mmol). The product was purified by RP-HPLC to give N-(3-(4-(1,2,3-thiadiazol-4-yl)benzamido)-4-chlorophenyl)-2-methyl-6-(trifluoromethyl)nicotinamide. MS (Q1) 518.1 (M)+

Example 17

N-(3-(4-(1H-imidazol-1-yl)benzamido)-4-chlorophenyl)-2-methyl-6-(trifluoromethyl)nicotinamide N-(3-amino-4-chlorophenyl)-2-methyl-6-(trifluoromethyl)nicotinamide (0.15 mmol) was used in general procedure 2 with 4-(1H-imidazol-1-yl)benzoic acid (0.167 mmol). The product was purified by RP-HPLC to give N-(3-(4-(1-H-imidazol-yl)benzamido)-4-chlorophenyl)-2-methyl-6-(trifluoromethyl)nicotinamide. MS (Q1) 500.0 (M)+

Example 18

N-(3-(4-(1H-1,2,4-triazol-1-yl)benzamido)-4-chlorophenyl)-2-methyl-6-(trifluoromethyl)nicotinamide N-(3-amino-4-chlorophenyl)-2-methyl-6-(trifluoromethyl)nicotinamide (0.15 mmol) was used in general procedure 2 with 1H-(1,2,4-triazol-1-yl)benzoic acid (0.167 mmol). The product was purified by RP-HPLC to give N-(3-(4-(1H-1,2,4-triazol-1-yl)benzamido)-4-chlorophenyl)-2-methyl-6-(trifluoromethyl)nicotinamide. MS (Q1) 501.0 (M)+

Example 19

N-(2-chloro-5-nitrophenyl)benzamide 2-chloro-5-nitroaniline (Aldrich), (10.0 mmol) was used in general procedure 1 with benzoyl chloride (12.2 mmol). The product was purified by silica gel chromatography (40% EtOAc/Hex) to give N-(2-chloro-5-nitrophenyl)benzamide as a tan solid. MS (Q1) 276.1 (M)+

Example 20

N-(5-amino-2-chlorophenyl)benzamide

N-(2-chloro-5-nitrophenyl)benzamidine (11.42 mmol) was used in general procedure 4 to give N-(5-amino-2-chlorophenyl)benzamide as a white solid. MS (Q1) 247.1 (M)+

Example 21

N-(3-benzamido-4-chlorophenyl)-6-morpholinonicotinamide

N-(5-amino-2-chlorophenyl)benzamide (0.24 mmol) was used in general procedure 2 with 6-morpholinonicotinic acid (0.30 mmol). The product was purified by RP-HPLC to give N-(3-benzamido-4-chlorophenyl)-6-morpholinonicotinamide. MS (Q1) 437.0 (M)+

Example 22

N-(3-benzamido-4-chlorophenyl)-2-methyl-4-phenylpyrimidin-5-carboxamide

N-(5-amino-2-chlorophenyl)benzamide (0.24 mmol) was used in general procedure 2 with 2-methyl-4-phenylpyrimidin-5-carboxylic acid (0.30 mmol). The product was purified by RP-HPLC to give N-(3-benzamido-4-chlorophenyl)-2-methyl-4-phenylpyrimidin-5-carboxamide. MS (Q1) 443.1 (M)+

Example 23

N-(3-benzamido-4-chlorophenyl)-1-(4-fluorophenyl)-4-methyl-1H-pyrazole-3-carboxamide N-(5-amino-2-chlorophenyl)benzamide (0.24 mmol) was used in general procedure 2 with 1-(4-fluorophenyl)-4-methyl-1H-pyrazole-3-carboxylic acid (0.30 mmol). The product was purified by RP-HPLC to give N-(3-benzamido-4-chlorophenyl)-1-(4-fluorophenyl)-4-methyl-1H-pyrazole-3-carboxamide. MS (Q1) 449.1 (M)+

Example 24

N-(3-benzamido-4-chlorophenyl)-4-methyl-2-phenylpyrimidin-5-carboxamide

N-(5-amino-2-chlorophenyl)benzamide (0.24 mmol) was used in general procedure 2 with 4-methyl-2-phenylpyrimidin-5-carboxylic acid (0.30 mmol). The product was purified by RP-HPLC to give N-(3-benzamido-4-chlorophenyl)-4-methyl-2-phenylpyridine-5-carboxamide. MS (Q1) 443.9 (M)+

Example 25

N-(3-benzamido-4-chlorophenyl)-6-chloronicotinamide

N-(5-amino-2-chlorophenyl)benzamide (2.0 mmol) was used in general procedure 1 with 6-chloronicotinyl chloride (2.2 mmol). The product was purified by RP-HPLC to give N-(3-benzamido-4-chlorophenyl)-6-chloronicotinamide. MS (Q1) 386.0 (M)+

Example 26

N-(3-benzamido-4-chlorophenyl)-6-((3S,5R)-3,5-dimethylpiperazine-1-yl)-nicotinamide N-(3-benzamido-4-chlorophenyl)-6-chloronicotinamide (0.15 mmol) was used in general procedure 3 with 2,6-dimethylpiperazine (0.77 mmol). The product was purified by RP-HPLC to give N-(3-benzamido-4-chlorophenyl)-6-(3S-,5R)-3-5-dimethylpiperazine-1-yl)nicotinamide. MS (Q1) 464.0 (M)+

Example 27

N-(3-benzamido-4-chlorophenyl)-6-(4-ethylpiperazin-1-yl)nicotinamide

N-(3-benzamido-4-chlorophenyl)-6-chloronicotinamide (0.15 mmol) was used in general procedure 3 with 1-ethylpiperazin (0.77 mmol). The product was purified by RP-HPLC to give N-(3-benzamido-4-chlorophenyl)-6-(4-ethylpiperazin-1-yl)nicotinamide. MS (Q1) 464.0 (M)+

Example 28

N-(3-benzamido-4-chlorophenyl)-6-(4-(2-hydroxyethyl)piperazin-1-yl)-nicotinamide N-(3-benzamido-4-chlorophenyl)-6-chloronicotinamide (0.15 mmol) was used in general procedure 3 with 2-piperazin-1-yl)ethanol (0.77 mmol). The product was purified by RP-HPLC to give N-(3-benzamido-4-chlorophenyl)-6-(4-(2-hydroxyethyl)piperazin-1-yl)nicotinamide. MS (Q1) 480.1 (M)+

Example 29

N-(3-benzamido-4-chlorophenyl)-6-(2,6-dimethylmorpholin)nicotinamide

N-(3-benzamido-4-chlorophenyl)-6-chloronicotinamide (0.15 mmol) was used in general procedure 3 with cis-2,6-dimethylmorpholine (0.77 mmol). The product was purified by RP-HPLC to give N-(3-benzamido-4-chlorophenyl)-6-(2,6-dimethylmorpholin))nicotinamide. MS (Q1) 465.0 (M)+

Example 30

6-(4-acetylpiperazin-1-yl)-N-(3-benzamido-4-chlorophenyl)nicotinamide

N-(3-benzamido-4-chlorophenyl)-6-chloronicotinamide (0.15 mmol) was used in general procedure 3 with 1-acetylpiperazine (0.77 mmol). The product was purified by RP-HPLC to give 6-(4-acetylpiperazin-1-yl)-N-(3-benzamido-4-chlorophenyl)nicotinamide. MS (Q1) 478.0 (M)+

Example 31

N-(3-benzamido-4-chlorophenyl)-6-(4-hydroxypiperidin-1-yl)nicotinamide

N-(3-benzamido-4-chlorophenyl)-6-chloronicotinamide (0.15 mmol) was used in general procedure 3 with piperidin-4-ol (0.77 mmol). The product was purified by RP-HPLC to give N-(3-benzamido-4-chlorophenyl)-6-(4-hydroxypiperidin-1-yl)nicotinamide. MS (Q1) 451.2 (M)+

Example 32

N-(3-benzamido-4-chlorophenyl)-6-(3-methylpiperazin-1-yl)nicotinamide

N-(3-benzamido-4-chlorophenyl)-6-chloronicotinamide (0.18 mmol) was used in general procedure 3 with 2-methylpiperazin (0.54 mmol). The product was purified by RP-HPLC to give N-(3-benzamido-4-chlorophenyl)-6-(3-methylpiperazin-1-yl)nicotinamide. MS (Q1) 450.1 (M)+

Example 33

(R)—N-(3-benzamido-4-chlorophenyl)-6-(3-methylpiperazin-1-yl)nicotinamide

N-(3-benzamido-4-chlorophenyl)-6-chloronicotinamide (0.18 mmol) was used in general procedure 3 with (R)-2-methylpiperazin (0.54 mmol). The product was purified by RP-HPLC to give (R)—N-(3-benzamido-4-chlorophenyl)-6-(3-methylpiperazin-1-yl)nicotinamide. MS (Q1) 450.4 (M)+

Example 34

(S)—N-(3-benzamido-4-chlorophenyl)-6-(3-methylpiperazin-1-yl)nicotinamide

N-(3-benzamido-4-chlorophenyl)-6-chloronicotinanmide (0.18 mmol) was used in general procedure 3 with (S)-2-methylpiperazin (0.54 mmol). The product was purified by RP-HPLC to give (S)—N-(3-benzamido-4-chlorophenyl)-6-(3-methylpiperazin-1-yl)nicotinamide. MS (Q1) 450.4 (M)+

Example 35

N-(3-benzamido-4-chlorophenyl)-6-(piperazin-1-yl)nicotinamide

N-(3-benzamido-4-chlorophenyl)-6-chloronicotinanmide (0.15 mmol) was used in general procedure 3 with Boc-piperazine (0.77 mmol). The product was purified by RP-HPLC and deprotected with TFA to give N-(3-benzamido-4-chlorophenyl)-6-(piperazin-1-yl)nicotinamide. MS (Q1) 451.2 (M)+

Example 36

N-(3-benzamido-4-chlorophenyl)-6-chloro-2-methylnicotinamide

N-(5-amino-2-chlorophenyl)benzamide (2.0 mmol) was used in general procedure 1 with 6-chloro-2-methylnicotinyl chloride (2.2 mmol). The product was purified by RP-HPLC to give N-(3-benzamido-4-chlorophenyl)-6-chloro-2-methylnicotinamide. MS (Q1) 401.0 (M)+

Example 37

N-(3-benzamido-4-chlorophenyl)-6-((3S,5R)-3,5-dimethylpiperazine-1'-yl)-2-methylnicotinamide N-(3-benzamido-4-chlorophenyl)-6-chloro-2-methylnicotinamide (0.15 mmol) was used in general procedure 3 with cis-2,6-dimethylpiperazine (0.77 mmol). The product was purified by RP-HPLC to give N-(3-benzamido-4-chlorophenyl)-6-(3S-,5R)-3-5-dimethylpiperazine-1-yl)-2-methylnicotinamide. MS (Q1) 464.0 (M)+

Example 38

N-(3-benzamido-4-chlorophenyl)-6-(bromomethyl)nicotinamide

N-(5-amino-2-chlorophenyl)benzamide (1.0 mmol) was used in general procedure 2 with 6-(bromomethyl)nicotinic acid (21.1 mmol) to give N-(3-benzamido-4-chlorophenyl)-6-(bromomethyl)-nicotinamide. MS (Q1) 444.0 (M)+

Example 39

N-(3-benzamido-4-chlorophenyl)-6-(morpholinomethyl)nicotinamide

N-(3-benzamido-4-chlorophenyl)-6-(bromomethyl)nicotinamide (0.11 mmol) was used in general procedure 5 with morpholine (0.12 mmol). The product was purified by RP- HPLC to give N-(3-benzamido-4-chlorophenyl)-6-(morpholinomethyl)nicotinamide. MS (Q1) 450.0 (M)+

Example 40

N-(3-benzamido-4-chlorophenyl)-6-(piperidin-1-ylmethyl)nicotinamide

N-(3-benzamido-4-chlorophenyl)-6-(bromomethyl)nicotinamide (0.11 mmol) was used in general procedure 5 with piperidine (0.12 mmol). The product was purified by RP-HPLC to give N-(3-benzamido-4-chlorophenyl)-6-(piperidin-1-ylmethyl)nicotinamide. MS (Q1) 448.1 (M)+

Example 41

N-(3-benzamido-4-chlorophenyl)-6-((4-methylpiperazin-1-yl)methyl)nicotinamide

N-(3-benzamido-4-chlorophenyl)-6-(bromomethyl)nicotinamide (0.11 mmol) was used in general procedure 5 with 1-methylpiperazin (0.12 mmol). The product was purified by RP-HPLC to give N-(3-benzamido-4-chlorophenyl)-6-(4-methylpiperazin-1-ylmethyl)nicotinamide. MS (Q1) 464.0 (M)+

Example 42

N-(3-benzamido-4-chlorophenyl)-2-phenylthiazole-4-carboxamide

N-(5-amino-2-chlorophenyl)benzamide (0.20 mmol) was used in general procedure 2 with 2-phenylthiazole-4-carboxylic acid (0.25 mmol). The product was purified by RP-HPLC to give N-(3-benzamido-4-chlorophenyl)-2-phenylthiazole-4-carboxamide. MS (Q1) 434.0 (M)+

Example 43

N-(2-chloro-5-nitrophenyl)nicotinamide 2-chloro-5-nitroaniline (Aldrich, 28.97 mmol) was used in general procedure 1 with nicotinyl chloride (31.87 mmol). The product was purified by silica gel chromatography (40% EtOAc/Hex) to give N-(2-chloro-5-nitrophenyl)nicotinamide as a brown solid. MS (Q1) 278.1 (M)+

Example 44

N-(5-amino-2-chlorophenyl)nicotinamide

N-(2-chloro-5-nitrophenyl)nicotinamide (18.0 mmol) was used in general procedure 4 to give N-(5-amino-2-chlorophenyl)nicotinamide as a white solid. MS (Q1) 248.1 (M)+

Example 45

N-(2-chloro-5-(2-chloro-4-(methylsulfonyl)benzamido)phenyl)nicotinamide

N-(5-amino-2-chlorophenyl)nicotinamide (0.40 mmol) was used in general procedure 2 with 2-chloro-4-(methylsulfonyl)benzoic acid (0.48 mmol). The product was purified by RP-HPLC to give N-(2-chloro-4-(methylsulfonyl)benzamido)phenyl)nicotinamide. MS (Q1) 464.0 (M)+

Example 46

N-(2-chloro-5-nitrophenyl)-4-fluorobenzamide 2-chloro-5-nitroaniline (Aldrich, 28.97 mmol) was used in general procedure 1 with 4-fluorobenzoyl chloride (31.87 mmol). The product was purified by silica gel chromatography (40% EtOAc/Hex) to give N-(2-chloro-5-nitrophenyl) fluorobenzamide as a brown solid. MS (Q1) 294.0 (M)+

Example 47

N-(5-amino-2-chlorophenyl)-4-fluorobenzamide

N-(2-chloro-5-nitrophenyl)fluorobenzamide (18.0 mmol) was used in general procedure 4 to give N-(5-amino-2-chlorophenyl)-4-fluorobenzamide as a white solid. MS (Q1) 265.0 (M)+

Example 48

6-chloro-N-(4-chloro-3-(4-fluorobenzamido)phenyl)nicotinamide

N-(5-amino-2-chlorophenyl)-4-fluorobenzamide (1.5 mmol) was used in general procedure 1 with 6-chloronicotinyl chloride (1.6 mmol). The product was purified by RP-HPLC to give 6-chloro-N-(4-chloro-3-(4-fluorobenzamido)phenyl)nicotinamide. MS (Q1) 404.0 (M)+

Example 49

N-(4-chloro-3-(4-fluorobenzamido)phenyl)-6-((3S,5R)-3,5-dimethylpiperazine-1-yl)nicotinamide 6-chloro-N-(4-chloro-3-(4-fluorobenzamido)phenyl) nicotinamide (0.15 mmol) was used in general procedure 3 with cis-2,6-dimethylpiperazine (0.77 mmol). The product was purified by RP-HPLC to give N-(4-fluorobenzamido) phenyl)-6-(3S-,5R)-3-5-dimethylpiperazine-1-yl)nicotinamide. MS (Q1) 482.3 (M)+

Example 50

N-(4-chloro-3-(4-fluorobenzamido)phenyl)-6-(4-hydroxypiperidin-1-yl)nicotinamide 6-chloro-N-(4-chloro-3-(4-fluorobenzamido)phenyl) nicotinamide (0.17 mmol) was used in general procedure 3 with 1-hydroxypiperidine (0.868 mmol). The product was purified by RP-HPLC to give N-(4-chloro-3-(4-fluorobenzamido)phenyl)-6-(4-hydroxypiperidin-1-yl)nicotinamide. MS (Q1) 469.1 (M)+

Example 51

6-(4-acetylpiperazin-1-yl)-N-(4-chloro-3-(4-fluorobenzamido)phenyl)nicotinamide 6-chloro-N-(4-chloro-3-(4-fluorobenzamido)phenyl) nicotinamide (0.17 mmol) was used in general procedure 3 with 1-acetylpiperazine (0.868 mmol). The product was purified by RP-HPLC to give 6-(4-acetylpiperazin-1-yl-N-(4-chloro-3-(4-fluorobenzamido)phenylnicotinamide. MS (Q1) 495.0 (M)+

Example 52

6-(4-methylsulfonylpiperazine-1-yl-N-(4-chloro-3-(4-fluorobenzamido)phenyl-nicotinamide N-(4-chloro-3-(4-fluorobenzamido)phenyl)-6-(piperazin-1-yl)nicotinamide (0.182 mmol) was used in general procedure 1 with methane sulfonyl chloride (0.20 mmol). The product was purified by RP-HPLC to give 6-(4-methylsulfonylpiperazine-1-yl-N-(4-chloro-3-(4-fluorobenzamido)-phenyl-nicotinamide. MS (Q1) 532.3 (M)+

Example 53

N-(3-(4-fluorobenzamido)-4-chlorophenyl)-6-(4-propionylpiperazin-1-yl)pyridine-3-carboxamide N-(4-chloro-3-(4-fluorobenzamido)phenyl)-6-(piperazin-1-yl)nicotinamide (0.182 mmol) was used in general procedure 1 with propionyl chloride (0.20 mmol). The product was purified by RP-HPLC to give N-(3-(4-fluorobenzamido)-4-chlorophenyl)-6-(4-propionylpiperazin-1-yl)pyridine-3-carboxamide. MS (Q1) 510.3 (M)+

Example 54

6-(4-(3-methylbutanoyl)piperazin-1-yl)-N-(3-(4-fluorobenzamido)-4-chlorophenyl)pyridine-3-carboxamide N-(4-chloro-3-(4-fluorobenzamido)phenyl)-6-(piperazin-1-yl)nicotinamide (0.182 mmol) was used in general procedure 1 with isovaleryl chloride (0.20 mmol). The product was purified by RP-HPLC to give 6-(4-(3-methylbutanoyl)piperazin-1-yl)-N-(3-(4-fluorobenzamido)-4-chlorophenyl)-pyridine-3-carboxamide. MS (Q1) 538.5 (M)+

Example 55

N-(3-(4-fluorobenzamido)-4-chlorophenyl)-6-(4-cyclopropylcarbonylpiperazin-1-yl)pyridine-3-carboxamide N-(4-chloro-3-(4-fluorobenzamido)phenyl)-6-(piperazin-1-yl)nicotinamide (0.182 mmol) was used in general procedure 1 with cyclopropyl chloride (0.20 mmol). The product was purified by RP-HPLC to give N-(3-(4-fluorobenzamido)-4-chlorophenyl)-6-(4-cyclopropylcarbonylpiperazin-1-yl)pyridine-3-carboxamide. MS (Q1) 522.3 (M)+

Example 56

N-(4-chloro-3-(4-fluorobenzamido)phenyl)-6-(4-ethylpiperazin-1-yl)nicotinamide 6-chloro-N-(4-chloro-3-(4-fluorobenzamido)phenyl) nicotinamide (0.17 mmol) was used in general procedure 3 with 1-ethylpiperazin (0.868 mmol). The product was purified by RP-HPLC to give N-(4-chloro-3-(4-fluorobenzamido)phenyl)-6-(4-ethylpiperazin-1-yl)nicotinamide. MS (Q1) 482.3 (M)+

Example 57

N-(4-chloro-3-(4-fluorobenzamido)phenyl)-6-(piperazin-1-yl)nicotinamide 6-chloro-N-(4-chloro-3-(4-fluorobenzamido)phenyl) nicotinamide (0.17 mmol) was used in general procedure 3 with Boc-piperazine (0.868 mmol). The product was deprotected by treatment with TFA and purified by RP-HPLC to give N-(4-chloro-3-(4-fluorobenzamido)phenyl)-6-(piperazin-1-yl)nicotinamide. MS (Q1) 554.0 (M)+

Example 58

N-(4-chloro-3-(4-fluorobenzamido)phenyl)-6-(3-methylpiperazin-1-yl)-nicotinamide 6-chloro-N-(4-chloro-3-(4-fluorobenzamido)phenyl) nicotinamide (0.18 mmol) was used in general procedure 3 with 2-methylpiperazin (0.54 mmol). The product was purified by RP-HPLC to give N-(4-chloro-3-(4-fluorobenzamido)phenyl)-6-(3-methylpiperazin-1-yl)nicotinamide. MS (Q1) 468.3 (M)+

Example 59

(R)—N-(4-chloro-3-(4-fluorobenzamido)phenyl)-6-(3-methylpiperazin-1-yl)-nicotinamide 6-chloro-N-(4-chloro-3-(4-fluorobenzamido)phenyl) nicotinamide (0.18 mmol) was used in general procedure 3 with (R)-2-methylpiperazin (0.54 mmol). The product was purified by RP-HPLC to give (R)—N-(4-chloro-3-(4-fluorobenzamido)phenyl)-6-(3-methylpiperazin-1-yl)nicotinamide. MS (Q1) 468.0 (M)+

Example 60

(S)—N-(4-chloro-3-(4-fluorobenzamido)phenyl)-6-(3-methylpiperazin-1-yl)-nicotinamide 6-chloro-N-(4-chloro-3-(4-fluorobenzamido)phenyl) nicotinamide (0.18 mmol) was used in general procedure 3 with (S)-2-methylpiperazin (0.54 mmol). The product was purified by RP-HPLC to give (S)—N-(4-chloro-3-(4-fluorobenzamido)phenyl)-6-(3-methylpiperazin-1-yl)nicotinamide. MS (Q1) 468.3 (M)+

Example 61

6-chloro-N-(4-chloro-3-(4-fluorobenzamido)phenyl)-2-methylnicotinamide

N-(5-amino-2-chlorophenyl)-4-fluorobenzamide (0.29 mmol) was used in general procedure 1 with 6-chloro-2-methylnicotinyl chloride (0.29 mmol). The product was purified by RP-HPLC to give 6-chloro-N-(4-chloro-3-(4-fluorobenzamido)phenyl)-2-methylnicotinamide. MS (Q1) 418.0 (M)+

Example 62

N-(4-chloro-3-(4-fluorobenzamido)phenyl)-6-(4-hydroxypiperidin-1-yl)-2-methylnicotinamide 6-chloro-N-(4-chloro-3-(4-fluorobenzamido)phenyl)-2-methylnicotinamide (0.17 mmol) was used in general procedure 3 with 1-hydroxypiperidine (0.868 mmol). The product was purified by RP-HPLC to give N-(4-chloro-3-(4-fluorobenzamido)phenyl)-6-(4-hydroxypiperidin-1-yl)-2-methylnicotinamide. MS (Q1) 500.0 (M)+

Example 63

N-(4-chloro-3-(4-fluorobenzamido)phenyl)-6-(3,5-dimethylpiperazine-1-yl)-2-methylnicotinamide 6-chloro-N-(4-chloro-3-(4-fluorobenzamido)phenyl)-2-methylnicotinamide (0.15 mmol) was used in general procedure 3 with cis-2,6-dimethylpiperazine (0.77 mmol). The product was purified by RP-HPLC to give N-(4-fluorobenzamido)phenyl))-6-(3S-,5R)-3-5-dimethylpiperazine-1-yl)-2-methylnicotinamide. MS (Q1) 496.0 (M)+

Example 64

6-(4-acetylpiperazin-1-yl)-N-(4-chloro-3-(4-fluorobenzamido)phenyl)-2-methylnicotinamide 6-chloro-N-(4-chloro-3-(4-fluorobenzamido)phenyl)-2-methylnicotinamide (0.17 mmol) was used in general procedure 3 with 1-acetylpiperazine (0.868 mmol). The product was purified by RP-HPLC to give 6-(4-acetylpiperazin-1-yl)-N-(4-chloro-3-(4-fluorobenzamido)phenyl)-2-methyl-nicotinamide. MS (Q1) 510.1 (M)+

Example 65

N-(2-chloro-5-(4-(methylsulfonylmethyl)benzamido)phenyl)nicotinamide

N-(5-amino-2-chlorophenyl)nicotinamide (0.36 mmol) was used in general procedure 2 with 4-(methylsulfonylmethyl)benzoic acid (0.36 mmol). The product was purified by RP-HPLC to give N-(2-chloro-5-(4-(methylsulfonyl)benzamido)phenyl)nicotinamide. MS (Q1) 464.0 (M)+

Example 66

3-chloro-N-(2-chloro-5-nitrophenyl)benzamide 2-chloro-5-nitroaniline (Aldrich, 25.7 mmol) was used in general procedure 1 with 3-chlorobenzoyl chloride (26.5 mmol). The product was purified by silica gel chromatography (40% EtOAc/Hex) to give 3-chloro-N-(2-chloro-5-nitrophenyl)benzamide as a brown solid. MS (Q1) 294.0 (M)+

Example 67

N-(5-amino-2-chlorophenyl)-3-chlorobenzamido 3-chloro-N-(2-chloro-5-nitrophenyl)benzamide (18.0 mmol) was used in general procedure 4 to give N-(5-amino-2-chlorophenyl)-3-chlorobenzamido as a white solid. MS (Q1) 281.0 (M)+

Example 68

N-(5-(4-(1H-1,2,4-triazol-1-yl)benzamido)-2-chlorophenyl)-3-chlorobenzamido

N-(5-amino-2-chlorophenyl)-3-chlorobenzamido (0.25 mmol) was used in general procedure 2 with 4-(1H-1,2,4-triazol-1-yl)benzoic acid (0.29 mmol). The product was purified by RP-HPLC to give N-(5-(4-(1H-1,2,4-triazol-1-yl)benzamido)-2-chlorophenyl)-3-chlorobenzamido. MS (Q1) 453.3 (M)+

Example 69

6-chloro-N-(4-chloro-3-(3-chlorobenzamido)phenyl)nicotinamide

N-(5-amino-2-chlorophenyl)-3-chlorobenzamido (1.15 mmol) was used in general procedure 1 with 6-chloronicotinyl chloride (1.26 mmol). The product was purified by RP-HPLC to give 6-chloro-N-(4-chloro-3-(3-chlorobenzamido)phenyl)nicotinamide. MS (Q1) 420.0 (M)+

Example 70

N-(4-chloro-3-(3-chlorobenzamido)phenyl)-6-((3S,5R)-3,5-dimethylpiperazine-1-yl)nicotinamide 6-chloro-N-(4-chloro-3-(3-chlorobenzamido)phenyl)nicotinamide (0.16 mmol) was used in general procedure 3 with cis-2,6-dimethylpiperazine (0.83 mmol). The product was purified by RP-HPLC to give N-(4-chloro-3-(3-chlorobenzamido)phenyl))-6-(3S,5R)-3-5-dimethylpiperazine-1-yl)-nicotinamide. MS (Q1) 498.0 (M)+

Example 71

N-(4-chloro-3-(3-chlorobenzamido)phenyl)-6-(4-hydroxypiperidin-1-yl)-nicotinamide 6-chloro-N-(4-chloro-3-(3-chlorobenzamido)phenyl)nicotinamide (0.16 mmol) was used in general procedure 3 with 1-hydroxypiperidine (0.83 mmol). The product was purified by RP-HPLC to give N-(4-chloro-3-(3-chlorobenzamido)phenyl))-6-(4-hydroxypiperidin-1-yl)nicotinamide. MS (Q1) 485.4 (M)+

Example 72

6-(4-acetylpiperazin-1-yl)-N-(4-chloro-3-(3-chlorobenzamido)phenyl)nicotinamide 6-chloro-N-(4-chloro-3-(3-chlorobenzamido)phenyl)nicotinamide (0.16 mmol) was used in general procedure 3 with 1-acetylpiperazine (0.83 mmol). The product was purified by RP-HPLC to give 6-(4-acetylpiperazin-1-yl)-N-(4-chloro-3-(3-chlorobenzamido)phenyl))phenyl)nicotinamide. MS (Q1) 512.0 (M)+

Example 73

N-(4-chloro-3-(3-chlorobenzamido)phenyl)-6-(4-ethylpiperazin-1-yl)nicotinamide 6-chloro-N-(4-chloro-3-(3-chlorobenzamido)phenyl)nicotinamide (0.16 mmol) was used in general procedure 3 with 1-ethylpiperazin (0.83 mmol). The product was purified by RP-HPLC to give N-(4-chloro-3-(3-chlorobenzamido)phenyl))-6-(4-ethylpiperazin-1-yl)nicotinamide. MS (Q1) 498.1 (M)+

Example 74

N-(4-chloro-3-(3-chlorobenzamido)phenyl)-6-(piperazin-1-yl)nicotinamide 6-chloro-N-(4-chloro-3-(3-chlorobenzamido)phenyl)nicotinamide (0.16 mmol) was used in general procedure 3 with Boc-piperazine (0.868 mmol). The product was deprotected by treatment with TFA and purified by RP-HPLC to give N-(4-chloro-3-(3-chlorobenzamido)phenyl))-6-(piperazin-1-yl)nicotinamide. MS (Q1) 470.1 (M)+

Example 75

N-(4-chloro-3-(3-chlorobenzamido)phenyl)-6-(4-(2-hydroxyethyl)piperazin-1-yl)-nicotinamide 6-chloro-N-(4-chloro-3-(3-chlorobenzamido)phenyl)nicotinamide (0.143 mmol) was used in general procedure 3 with 2-(piperazin-1-yl)ethanol (0.71 mmol). The product was purified by RP-HPLC to give N-(4-chloro-3-(3-chlorobenzamido)phenyl))-6-(4-(2-hydroxyethyl)piperazin-1-yl)-nicotinamide. MS (Q1) 498.0 (M)+

Example 76

6-(bromomethyl)-N-(4-chloro-3-(3-chlorobenzamido)phenyl)nicotinamide

N-(5-amino-2-chlorophenyl)-3-chlorobenzamido (1.0 mmol) was used in general procedure 2 with 6-(bromomethyl)nicotinic acid (2.1 mmol) to give 6-(bromomethyl)-N-(4-chloro-3-(3-chlorobenzamido)phenyl)nicotinamide. MS (Q1) 478.1 (M)+

Example 77

N-(4-chloro-3-(3-chlorobenzamido)phenyl)-6-((4-ethylpiperazin-1-yl)methyl)-nicotinamide 6-(bromomethyl)-N-(4-chloro-3-(3-chlorobenzamido)phenyl)nicotinamide (0.2 mmol) was used in general procedure 5 with 1-ethylpiperazine (0.4 mmol). The product was purified by RP-HPLC to give N-(4-chloro-3-(3-chlorobenzamido)phenyl))-6-(4-ethylpiperazin-1-yl)methylnicotinamide. MS (Q1) 512.2 (M)+

Example 78

N-(4-chloro-3-(3-chlorobenzamido)phenyl)-6-((4-methylpiperazin-1-yl)methyl)-nicotinamide 6-(bromomethyl)-N-(4-chloro-3-(3-chlorobenzamido)phenyl)nicotinamide (0.2 mmol) was used in general procedure 5 with 1-methylpiperazin (0.4 mmol). The product was purified by RP-HPLC to give N-(4-chloro-3-(3-chlorobenzamido)phenyl))-6-(4-ethylpiperazin-1-yl)methylnicotinamide. MS (Q1) 498.1 (M)+

Example 79

N-(4-chloro-3-(3-chlorobenzamido)phenyl)-6-((1-methylpiperidin-4-ylamino)methyl)nicotinamide 6-(bromomethyl)-N-(4-chloro-3-(3-chlorobenzamido)phenyl)nicotinamide (0.2 mmol) was used in general procedure 5 with 1-methylpiperidin-4-amine (0.4 mmol). The product was purified by RP-HPLC to give N-(4-chloro-3-(3-chlorobenzamido)phenyl))-6-((1-methylpiperidin-4-ylamino)-methyl)nicotinamide. MS (Q1) 512.3 (M)+

Example 80

6-((4-acetylpiperazin-1-yl)methyl)-N-(4-chloro-3-(3-chlorobenzamido)phenyl)-nicotinamide 6-(bromomethyl)-N-(4-chloro-3-(3-chlorobenzamido)phenyl)nicotinamide (0.2 mmol) was used in general procedure 5 with 1-acetylpiperazine (0.4 mmol). The product was purified by RP-HPLC to give 6-((4-acetylpiperazin-1-yl)methyl)-N-(4-chloro-3-(3-chlorobenzamido)phenyl)nicotinamide. MS (Q1) 526.0 (M)+

Example 81

N-(4-chloro-3-(3-chlorobenzamido)phenyl)-6-(((3S,5R)-3,5-dimethylpiperazine-1-yl)methyl)nicotinamide 6-(bromomethyl)-N-(4-chloro-3-(3-chlorobenzamido)phenyl)nicotinamide (0.2 mmol) was used in general procedure 5 with cis-2,6-dimethylpiperazine (0.4 mmol). The product was purified by RP-HPLC to give N-(4-chloro-3-(3-chlorobenzamido)phenyl))-6-(((3S,5R)-3-5-dimethylpiperazine-1-yl)methyl)nicotinamide. MS (Q1) 512.3 (M)+

Example 82

6-chloro-N-(4-chloro-3-(3-chlorobenzamido)phenyl)-2-methylnicotinamide

N-(5-amino-2-chlorophenyl)-3-chlorobenzamido (0.29 mmol) was used in general procedure 2 with 6-chloro-2-methylnicotinic acid (0.29 mmol). The product was purified by RP-HPLC to give 6-chloro-N-(4-chloro-3-(3-chlorobenzamido)phenyl)-2-methylnicotinamide. MS (Q1) 434.0 (M)+

Example 83

N-(4-chloro-3-(3-chlorobenzamido)phenyl)-6-((3S,5R)-3,5-dimethylpiperazine-1-yl)-2-methylnicotinamide 6-chloro-N-(4-chloro-3-(3-chlorobenzamido)phenyl)-2-methylnicotinamide (0.14 mmol) was used in general procedure 3 with cis-2,6-dimethylpiperazine (0.70 mmol). The product was purified by RP-HPLC to give N-(4-chloro-3-(3-chlorobenzamido)phenyl))-6-(3S,5R)-3-5-dimethylpiperazine-1-yl)-2-methylnicotinamide. MS (Q1) 512.0 (M)+

Example 84

N-(4-chloro-3-(3-chlorobenzamido)phenyl)-6-(4-hydroxypiperidin-1-yl)-2-methylnicotinamide 6-chloro-N-(4-chloro-3-(3-chlorobenzamido)phenyl)-2-methylnicotinamide (0.16 mmol) was used in general procedure 3 with 1-hydroxypiperidine (0.83 mmol). The product was purified by RP-HPLC to give N-(4-chloro-3-(3-chlorobenzamido)phenyl))-6-(4-hydroxypiperidin-1-yl)-2-methyl-nicotinamide. MS (Q1) 499.1 (M)+

Example 85

6-(4-acetylpiperazin-1-yl)-N-(4-chloro-3-(3-chlorobenzamido)phenyl)-2-methyl-nicotinamide 6-chloro-N-(4-chloro-3-(3-chlorobenzamido)phenyl)-2-methylnicotinamide (0.16 mmol) was used in general procedure 3 with 1-acetylpiperazine (0.83 mmol). The product was purified by RP-HPLC to give 6-(4-acetylpiperazin-1-yl)-N-(4-chloro-3-(3-chlorobenzamido)phenyl))phenyl)-2-methylnicotinamide. MS (Q1) 526.1 (M)+

Example 86

6-chloro-N-(4-chloro-3-nitrophenyl)nicotinamide 3-nitro-4-chloroaniline (Aldrich, 23.18 mmol) was used in general procedure 1 with 6-chloronicotinyl chloride (46.36 mmol). The product was purified by silica gel chromatography (40% EtOAc/Hex) to give 6-chloro-N-(4-chloro-3-nitrophenyl)nicotinamide as a tan solid. MS (Q1) 312.0 (M)+

Example 87

6-(4-acetylpiperazin-1-yl)-N-(4-chloro-3-nitrophenyl)nicotinamide 6-chloro-N-(4-chloro-3-nitrophenyl)nicotinamide (1.6 mmol) was used in general procedure 3 with 1-acetylpiperazine (4.8 mmol to give 6-(4-acetylpiperazin-1-yl)-N-(4-chloro-3-nitrophenyl))-nicotinamide. MS (Q1) 404.4 (M)+

Example 88

6-(4-acetylpiperazin-1-yl)-N-(3-amino-4-chlorophenyl)nicotinamide 6-(4-acetylpiperazin-1-yl)-N-(4-chloro-3-nitrophenyl))nicotinamide (2.47 mmol) was used in general procedure 4 to give 6-(4-acetylpiperazin-1-yl)-N-(3-amino-4-chlorophenyl)nicotinamide as a white solid. MS (Q1) 374.1 (M)+

Example 89

6-(4-acetylpiperazin-1-yl)-N-(4-chloro-3-(2-chlorobenzamido)phenyl)nicotinamide 6-(4-acetylpiperazin-1-yl)-N-(3-amino-4-chlorophenyl))nicotinamide (0.18 mmol) was used in general procedure 2 with 2-chlorobenzoic acid (0.26 mmol). The product was purified by RP-HPLC to give 6-(4-acetylpiperazin-1-yl)-N-(4-chloro-3-(2-chlorobenzamido)phenyl)nicotinamide. MS (Q1) 512.3 (M)+

Example 90

6-(4-acetylpiperazin-1-yl)-N-(4-chloro-3-(2-fluorobenzamido)phenyl)nicotinamide 6-(4-acetylpiperazin-1-yl)-N-(3-amino-4-chlorophenyl))nicotinamide (0.18 mmol) was used in general procedure 2 with 2-fluorobenzoic acid (0.26 mmol). The product was purified by RP-HPLC to give 6-(4-acetylpiperazin-1-yl)-N-(4-chloro-3-(2-fluorobenzamido)phenyl)nicotinamide. MS (Q1) 496.1 (M)+

Example 91

N-(3-amino-4-chlorophenyl)-6-chloronicotinamide 6-chloro-N-(4-chloro-3-nitrophenyl)nicotinamide (18.0 mmol) was used in general procedure 4 to give N-(3-amino-4-chlorophenyl)-6-chloronicotinamide as a white solid. MS (Q1) 282.1 (M)+

Example 92

6-chloro-N-(4-chloro-3-(3-fluorobenzamido)phenyl)nicotinamide

N-(3-amino-4-chlorophenyl)-6-chloronicotinamide (0.16 mmol) was used in general procedure 2 with 3-fluorobenzoic acid (0.83 mmol). The product was purified by RP-HPLC to give 6-chloro-N-(4-chloro-3-(3-fluorobenzamido)phenyl)nicotinamide. MS (Q1) 404.3 (M)+

Example 93

N-(4-chloro-3-(3-fluorobenzamido)phenyl)-6-((3S, 5R)-3,5-dimethylpiperazine-1-yl)-nicotinamide 6-chloro-N-(4-chloro-3-(3-fluorobenzamido)phenyl)nicotinamide (0.117 mmol) was used in general procedure 3 with 2,6-dimethylpiperazine (0.35 mmol). The product was purified by RP-HPLC to give N-(4-chloro-3-(3-fluorobenzamido)phenyl))-6-(3S,5R)-3-5-dimethylpiperazine-1-yl)nicotinamide. MS (Q1) 482.1 (M)+

Example 94

N-(4-chloro-3-(3-fluorobenzamido)phenyl)-6-(4-hydroxypiperidin-1-yl)-nicotinamide 6-chloro-N-(4-chloro-3-(3-fluorobenzamido)phenyl)nicotinamide (0.117 mmol) was used in general procedure 3 with 1-hydroxypiperidine (0.35 mmol). The product was purified by RP-HPLC to give N-(4-chloro-3-(3-fluorobenzamido)phenyl))-6-(4-hydroxypiperidin-1-yl)nicotinamide. MS (Q1) 469.0 (M)+

Example 95

6-(4-acetylpiperazin-1-yl)-N-(4-chloro-3-(3-fluorobenzamido)phenyl)nicotinamide 6-chloro-N-(4-chloro-3-(3-fluorobenzamido)phenyl)nicotinamide (0.117 mmol) was used in general procedure 3 with 1-acetylpiperazine (0.35 mmol). The product was purified by RP-HPLC to give 6-(4-acetylpiperazin-1-yl)-N-(3-fluoro-3-(3-chlorobenzamido)phenyl))phenyl)nicotinamide. MS (Q1) 496.1 (M)+

Example 96

6-chloro-N-(4-chloro-3-(2-fluorobenzamido)phenyl)nicotinamide

N-(3-amino-4-chlorophenyl)-6-chloronicotinamide (0.16 mmol) was used in general procedure 2 with 2-fluorobenzoic acid (0.83 mmol). The product was purified by RP-HPLC to give 6-chloro-N-(4-chloro-3-(2-fluorobenzamido)phenyl) nicotinamide. MS (Q1) 404.3 (M)+

Example 97

N-(4-chloro-3-(2-fluorobenzamido)phenyl)-6-((3S, 5R)-3,5-dimethylpiperazine-1-yl)nicotinamide 6-chloro-N-(4-chloro-3-(2-fluorobenzamido)phenyl) nicotinamide (0.177 mmol) was used in general procedure 3 with 2,6-dimethylpiperazine (0.70 mmol). The product was purified by RP-HPLC to give N-(4-chloro-3-(2-fluorobenzamido)phenyl))-6-(3S,5R)-3-5-dimethylpiperazine-1-yl) nicotinamide. MS (Q1) 482.1 (M)+

Example 98

N-(4-chloro-3-(2-fluorobenzamido)phenyl)-6-(4-hydroxypiperidin-1-yl)-nicotinamide 6-chloro-N-(4-chloro-3-(2-fluorobenzamido)phenyl) nicotinamide (0.177 mmol) was used in general procedure 3 with 1-hydroxypiperidine (0.70 mmol). The product was purified by RP-HPLC to give N-(4-chloro-3-(3-fluorobenzamido)phenyl))-6-(4-hydroxypiperidin-1-yl)nicotinamide. MS (Q1) 469.0 (M)+

Example 99

6-chloro-N-(4-chloro-3-(4-chlorobenzamido)phenyl) nicotinamide

N-(3-amino-4-chlorophenyl)-6-chloronicotinamide (0.71 mmol) was used in general procedure 2 with 4-chlorobenzoic acid (0.78 mmol). The product was purified by RP-HPLC to give 6-chloro-N-(4-chloro-3-(4-chlorobenzamido)phenyl) nicotinamide. MS (Q1) 419.8 (M)+

Example 100

N-(4-chloro-3-(4-chlorobenzamido)phenyl)-6-((3S, 5R)-3,5-dimethylpiperazine-1-yl)nicotinamide 6-chloro-N-(4-chloro-3-(4-chlorobenzamido)phenyl) nicotinamide (0.19 mmol) was used in general procedure 3 with cis-2,6-dimethylpiperazine (0.57 mmol). The product was purified by RP-HPLC to give N-(4-chloro-3-(4-chlorobenzamido)phenyl))-6-(3S,5R)-3-5-dimethylpiperazine-1-yl)-nicotinamide. MS (Q1) 498.0 (M)+

Example 101

N-(4-chloro-3-(4-chlorobenzamido)phenyl)-6-(4-hydroxypiperidin-1-yl)-nicotinamide 6-chloro-N-(4-chloro-3-(4-chlorobenzamido)phenyl) nicotinamide (0.19 mmol) was used in general procedure 3 with 1-hydroxypiperidine (0.57 mmol). The product was purified by RP-HPLC to give N-(4-chloro-3-(4-chlorobenzamido)phenyl))-6-(4-hydroxypiperidin-1-yl)nicotinamide. MS (Q1) 485.4 (M)+

Example 102

6-(4-acetylpiperazin-1-yl)-N-(4-chloro-3-(4-chlorobenzamido)phenyl)nicotinamide 6-chloro-N-(4-chloro-3-(4-chlorobenzamido)phenyl) nicotinamide (0.16 mmol) was used in general procedure 3 with 1-acetylpiperazine (0.83 mmol). The product was purified by RP-HPLC to give 6-(4-acetylpiperazin-1-yl)-N-(4-chloro-3-(4-chlorobenzamido)phenyl)nicotinamide. MS (Q1) 512.3 (M)+

Example 103

6-chloro-N-(4-chloro-3-(2-chlorobenzamido)phenyl) nicotinamide

N-(3-amino-4-chlorophenyl)-6-chloronicotinamide (0.2 mmol) was used in general procedure 2 with 2-chlorobenzoic acid (0.8 mmol). The product was purified by RP-HPLC to give 6-chloro-N-(4-chloro-3-(2-chlorobenzamido)phenyl) nicotinamide. MS (Q1) 419.8 (M)+

Example 104

N-(4-chloro-3-(2-chlorobenzamido)phenyl)-6-((3S, 5R)-3,5-dimethylpiperazine-1-yl)nicotinamide 6-chloro-N-(4-chloro-3-(2-chlorobenzamido)phenyl) nicotinamide (0.2 mmol) was used in general procedure 3 with cis-2,6-dimethylpiperazine (0.8 mmol). The product was purified by RP-HPLC to give N-(4-chloro-3-(2-chlorobenzamido)phenyl))-6-(3S,5R)-3-5-dimethylpiperazine-1-yl)-nicotin-amide. MS (Q1) 498.1 (M)+

Example 105

N-(4-chloro-3-(2-chlorobenzamido)phenyl)-6-(4-hydroxypiperidin-1-yl)-nicotinamide 6-chloro-N-(4-chloro-3-(2-chlorobenzamido)phenyl) nicotinamide (0.2 mmol) was used in general procedure 3 with 1-hydroxypiperidine (0.8 mmol). The product was purified by RP-HPLC to give N-(4-chloro-3-(2-chlorobenzamido)phenyl))-6-(4-hydroxypiperidin-1-yl)nicotinamide. MS (Q1) 485.1 (M)+

Example 106

6-chloro-N-(4-chloro-3-(4-methylbenzamide)phenyl) nicotinamide

N-(3-amino-4-chlorophenyl)-6-chloronicotinamide (0.71 mmol) was used in general procedure 2 with 4-methylbenzoic acid (0.78 mmol). The product was purified by RP-HPLC to give 6-chloro-N-(4-chloro-3-(4-methylbenzamide)phenyl) nicotinamide. MS (Q1) 400.1 (M)+

Example 107

N-(4-chloro-3-(4-methylbenzamide)phenyl)-6-((3S, 5R)-3,5-dimethylpiperazine-1-yl)nicotinamide 6-chloro-N-(4-chloro-3-(4-methylbenzamide)phenyl) nicotinamide (0.19 mmol) was used in general procedure 3 with cis-2,6-dimethylpiperazine (0.57 mmol). The product was purified by RP-HPLC to give N-(4-chloro-3-(4-methylbenzamide)phenyl))-6-(3S,5R)-3-5-dimethylpiperazine-1-yl)-nicotinamide. MS (Q1) 478.3 (M)+

Example 108

N-(4-chloro-3-(4-methylbenzamide)phenyl)-6-(4-hydroxypiperidin-1-yl)-nicotinamide 6-chloro-N-(4-chloro-3-(4-chlorobenzamido)phenyl) nicotinamide (0.18 mmol) was used in general procedure 3 with 1-hydroxypiperidine (0.54 mmol). The product was purified by RP-HPLC to give N-(4-chloro-3-(4-methylbenzamide)phenyl))-6-(4-hydroxypiperidin-1-yl)nicotinamide. MS (Q1) 465.3 (M)+

Example 109

6-(4-acetylpiperazin-1-yl)-N-(4-chloro-3-(4-methylbenzamide)phenyl)-nicotinamide 6-chloro-N-(4-chloro-3-(4-methylbenzamide)phenyl)-nicotinamide (0.16 mmol) was used in general procedure 3 with 1-acetylpiperazine (0.83 mmol). The product was purified by RP-HPLC to give 6-(4-acetylpiperazin-1-yl)-N-(4-chloro-3-(4-methylbenzamide)phenyl)-nicotinamide. MS (Q1) 492.3 (M)+

Example 110

6-chloro-N-(4-chloro-3-(2-methylbenzamide)phenyl) nicotinamide

N-(3-amino-4-chlorophenyl)-6-chloronicotinamide (0.71 mmol) was used in general procedure 2 with 2-methylbenzoic acid (0.78 mmol). The product was purified by RP-HPLC to give 6-chloro-N-(4-chloro-3-(2-methylbenzamide)phenyl) nicotinamide. MS (Q1) 400.1 (M)+

Example 111

N-(4-chloro-3-(2-methylbenzamide)phenyl)-6-((3S, 5R)-3,5-dimethylpiperazine-1-yl)nicotinamide 6-chloro-N-(4-chloro-3-(2-methylbenzamide)phenyl) nicotinamide (0.186 mmol) was used in general procedure 3 with cis-2,6-dimethylpiperazine (0.744 mmol). The product was purified by RP-HPLC to give N-(4-chloro-3-(2-methylbenzamide)phenyl))-6-(3S,5R)-3-5-dimethylpiperazine-1-yl)nicotinamide. MS (Q1) 478.3 (M)+

Example 112

N-(4-chloro-3-(2-methylbenzamide)phenyl)-6-(4-hydroxypiperidin-1-yl)-nicotinamide 6-chloro-N-(4-chloro-3-(2-chlorobenzamido)phenyl) nicotinamide (0.18 mmol) was used in general procedure 3 with 1-hydroxypiperidine (0.54 mmol). The product was purified by RP-HPLC to give N-(4-chloro-3-(2-methylbenzamide)phenyl))-6-(4-hydroxypiperidin-1-yl)nicotinamide. MS (Q1) 465.3 (M)+

Example 113

6-(4-acetylpiperazin-1-yl)-N-(4-chloro-3-(2-methylbenzamide)phenyl)-nicotinamide 6-(4-acetylpiperazin-1-yl)-N-(3-amino-4-chlorophenyl) nicotinamide (0.18 mmol) was used in general procedure 2 with 2-methyl benzoic acid (0.26 mmol). The product was purified by RP-HPLC to give N-(3-(2-methylbenzamide)-4-chlorophenyl)-6-(4-acetylpiperazin-1-yl)pyridine-3-carboxamide. MS (Q1) 492.0 (M)+

Example 114

6-chloro-N-(4-chloro-3-(3-methylbenzamide)phenyl) nicotinamide

N-(3-amino-4-chlorophenyl)-6-chloronicotinamide (0.71 mmol) was used in general procedure 2 with 3-methylbenzoic acid (0.78 mmol). The product was purified by RP-HPLC to give 6-chloro-N-(4-chloro-3-(3-methylbenzamide)phenyl) nicotinamide. MS (Q1) 400.1 (M)+

Example 115

N-(4-chloro-3-(3-methylbenzamide)phenyl)-6-((3S, 5R)-3,5-dimethylpiperazine-1-yl)nicotinamide 6-chloro-N-(4-chloro-3-(3-methylbenzamide)phenyl) nicotinamide (0.186 mmol) was used in general procedure 3 with cis-2,6-dimethylpiperazine (0.744 mmol). The product was purified by RP-HPLC to give N-(4-chloro-3-(3-methylbenzamide)phenyl))-6-(3S,5R)-3-5-dimethylpiperazine-1-yl)nicotinamide. MS (Q1) 478.3 (M)+

Example 116

N-(4-chloro-3-(3-methylbenzamide)phenyl)-6-(4-hydroxypiperidin-1-yl)-nicotinamide 6-chloro-N-(4-chloro-3-(3-chlorobenzamido)phenyl) nicotinamide (0.18 mmol) was used in general procedure 3 with 1-hydroxypiperidine (0.54 mmol). The product was purified by RP-HPLC to give N-(4-chloro-3-(3-methylbenzamide)phenyl))-6-(4-hydroxypiperidin-1-yl)nicotinamide. MS (Q1) 465.3 (M)+

Example 117

6-(4-acetylpiperazin-1-yl)-N-(4-chloro-3-(3-methylbenzamide)phenyl)-nicotinamide 6-chloro-N-(4-chloro-3-(3-methylbenzamide)phenyl)-nicotinamide (0.16 mmol) was used in general procedure 3 with 1-acetylpiperazine (0.83 mmol). The product was purified by RP-HPLC to give 6-(4-acetylpiperazin-1-yl)-N-(4-chloro-3-(3-methylbenzamide)phenyl)-nicotinamide. MS (Q1) 492.3 (M)+

Example 118

Hedgehog Signaling Inhibition Assays

Mouse Reporter Cell lines—10T½-GliLuc [S 12] cells (derived from cell line C3H10T½ ATCC #CCL-226); Mouse Embryonic Fibroblasts); Growth Medium: Dulbecco's modified Eagles' Medium (DMEM) supplemented with 10% Fetal Bovine Serum (FBS), 10 units/mL penicillin, 100 ug/mL streptomycin, 2 mM glutamine, and 10 mM HEPES.

Human Reporter Cell lines—HEPM-GliLuc [MZ24]—cells (derived from HEPM, Human Embryonic Palatal Mesenchyme ATCC #CRL-1486); Growth Medium: Minimum Essential Medium (MEM; with Earle's salts) supplemented with 10-20% Fetal Bovine Serum (FBS), 10 units/mL penicillin, 100 ug/mL streptomycin, 2 mM glutamine, and 10 mM HEPES pH 7.2.

Sonic hedgehog—recombinant human SHh N-terminal octylated conjugate.

Microtiter Plates (MTPs)—For the Luciferase assay cells are plated in 96-well MTPs (White, Flat-bottom, Clear-View).

Luciferase-Assay Medium—DMEM supplemented with 0.5% FBS, 10 units/mL penicillin, 100 ug/mL streptomycin, 2 mM glutamine, and 10 mM HEPES pH 7.2.

PBS/Ca/Mg Mix—Phosphate Buffered Saline (PBS) supplemented with 0.5 mM $CaCl_2$ and 1 mM $MgCl_2$.

Assay Procedure

S12 and MZ24 cells genetically modified to contain a luciferase reporter gene driven by the hedgehog-responsive Gli promoter were maintained on tissue culture dishes in Growth Medium at 37° C. and 5% $CO_2$. Cell cultures were passaged at sub-confluency at every 3-4 days. (1:20 to 1:40 for s12; 1:3 to 1:10 for MZ24). Cells were harvested and diluted in Growth Medium such that they could be plated in a microtitre plate at 10,000-20,000 cells (s12), or 20,000-30,000 cells (MZ24), per 100 ul, per well. Cells were further incubated for ~24-48 hours at 37° C. and 5% $CO_2$.

After ~24-48 hour incubation the Growth Medium in the microtitre plates was replaced by Luciferase-Assay Medium (100 ul per well), with and without Sonic hedgehog-octyl conjugate, at 0.1-0.3 ug/ml (S12) or 0.5-1.0 ug/ml (MZ24), and test compounds. Cells were then further incubated for and additional 24 hrs.

Microtitre plates were then subjected to the luciferase reporter gene assay kit (LucLite™), with modifications to the manufacturer's procedure wherein medium was removed and the substrate was reconstituted with 1:1 PBS/Ca/Mg:lysis buffer instead of straight lysis buffer. In brief, the PBS/Ca/Mg was mixed 1:1 with lysis buffer and 10 mL were added to each substrate vial (of the 1000-assay kit). Then the assay media from the microtitre plate was discarded, and 100 ul of this substrate mix was added to each well. Plates were incubated at room temperature for 20-30 minutes and then the Relative Light Units (RLUS) representing the relative expression level of the luciferase reporter gene were determined with a Topcount reader (Packard) or an Analyst reader (Molecular Devices). Compounds of the invention tested in the assays demonstrated reduced Gli expression in the reporter cell lines indicating hedgehog pathway signalling inhibition.

We claim:

1. A method for inhibiting hedgehog signaling in a cell comprising contacting said cell with a compound of formula I:

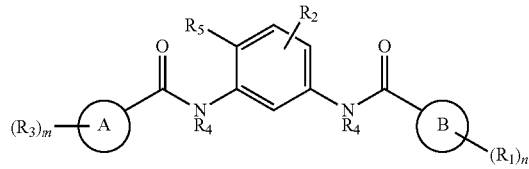

I wherein
ring A is benzene;
ring B is pyridine, pyrazine, pyrimidine, 1,2,4-triazine, thiophene, thiazole, imidazole, pyrrole or pyrazole;
carbocycle is a mono-, bi-, or tricyclic aliphatic ring having 3 to 14 carbon atoms which is saturated or unsaturated, aromatic or non-aromatic;
heterocycle is a mono-, bi-, or tricyclic, saturated or unsaturated, aromatic or non-aromatic ring having from 5 to about 14 ring atoms, where the ring atoms are 1 to 4 nitrogen, sulfur or oxygen heteroatoms and the balance carbon atoms;

$R_1$ is hydroxyl, halogen, amino, nitro, cyano, alkyl, acyl sulfonyl, sulfinyl, alkoxy, carbamoyl, acylamine, sulfamoyl or sulfonamide; wherein said amino, alkyl, acyl, sulfonyl, sulfinyl, alkoxy, carbamoyl, acylamine, sulfamoyl and sulfonamide substituent is optionally substituted with amino, halogen, hydroxyl, oxo, or is substituted with a carbocycle or heterocycle, as defined above, that is optionally substituted with hydroxyl, amino, halogen, haloalkyl, alkyl, alkoxy or acyl;

or $R_1$ is a carbocycle or a heterocycle, as defined above, that is optionally substituted with hydroxyl, halogen, amino, nitro, cyano, alkyl, acyl, sulfonyl, sulfinyl, alkoxy, carbamoyl, acylamine, sulfamoyl, sulfonamide, a carbocycle or heterocycle, as defined above; wherein said amino, alkyl, acyl, sulfonyl, sulfinyl, alkoxy, carbamoyl, acylamine, sulfamoyl, sulfonamide, carbocycle and heterocycle substituent is optionally substituted with amino, halogen, hydroxyl, oxo, or is substituted with a carbocycle or heterocycle, as defined above, that is optionally substituted with hydroxyl, amino, halogen, haloalkyl, alkyl, alkoxy or acyl;

$R_2$ is hydrogen;

$R_3$ is Me, F, Cl, —$CH_2$—$SO_2$—Me, —$SO_2$—Me, 1H-1,2,4-triazol-1-yl, 1H-imidazol-1-yl, morpholino, thiomorpholino-methyl with S in the oxidized form $SO_2$, 1,2,3-thiadiazol-4-yl or N-methyl-piperizinyl;

each $R_4$ is independently H or alkyl;

$R_5$ is chloro;

m is 0-3;

n is 0-4;

or a salt or solvate thereof.

2. The method of claim 1, wherein ring B is pyridine.

3. The method of claim 1, wherein $R_1$ is alkyl, haloalkyl, aryl, a heterocycle, as defined above, or a heterocycloalkyl, which is a heterocycle group as defined above covalently bonded to an alkyl group, wherein said aryl, heterocycle and heterocycloalkyl is optionally substituted with hydroxy, halogen, alkyl, alkanoyl or hydroxyalkyl.

4. The method of claim 1, wherein $R_1$ is Me, $CF_3$, Ph, 4-F-phenyl, piperazin-1-yl, 4-methylpiperazin-1-yl, 4-ethylpiperazin-1-yl, 4-acetylpiperazin-1-yl, 3,5-dimethylpiperazin-1-yl, 4-(2-hydroxyethyl)-piperazin-1-yl, (4-methylpiperazin-1-yl)methyl, (4-ethylpiperazin-1-yl)methyl, (4-acetylpiperazin-1-yl)methyl, (3,5-dimethylpiperazin-1-yl)methyl, 4-hydroxypiperidin-1-yl, (piperidin-1-yl)methyl, (1-methylpiperidin-4-ylamino)methyl, morpholino, (3,5-dimethyl)morpholino, morpholinomethyl or 1H-1,2,4-triazol-1-yl.

5. The method of claim 1, wherein both $R_4$ groups are H.

6. A method for treating basal cell carcinoma associated with the hedgehog signaling in a mammal, comprising administering to said mammal an effective amount of a compound of formula I

I

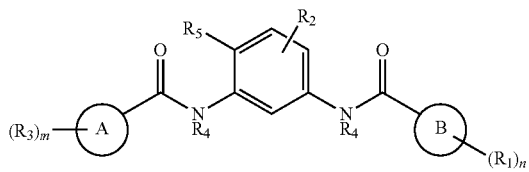

wherein
ring A is benzene;
ring B is pyridine, pyrazine, pyrimidine, 1,2,4-triazine, thiophene, thiazole, imidazole, pyrrole or pyrazole;
carbocycle is a mono-, bi-, or tricyclic aliphatic ring having 3 to 14 carbon atoms which is saturated or unsaturated, aromatic or non-aromatic;
heterocycle is a mono-, bi-, or tricyclic, saturated or unsaturated, aromatic or non-aromatic ring having from 5 to about 14 ring atoms, where the ring atoms are 1 to 4 nitrogen, sulfur or oxygen heteroatoms and the balance carbon atoms;
$R_1$ is hydroxyl, halogen, amino, nitro, cyano, alkyl, acyl sulfonyl, sulfinyl, alkoxy, carbamoyl, acylamine, sulfamoyl or sulfonamide; wherein said amino, alkyl, acyl, sulfonyl, sulfinyl, alkoxy, carbamoyl, acylamine, sulfamoyl and sulfonamide substituent is optionally substituted with amino, halogen, hydroxyl, oxo, or is substituted with a carbocycle or heterocycle, as defined above, that is optionally substituted with hydroxyl, amino, halogen, haloalkyl, alkyl, alkoxy or acyl;
or $R_1$ is a carbocycle or a heterocycle, as defined above, that is optionally substituted with hydroxyl, halogen, amino, nitro, cyano, alkyl, acyl, sulfonyl, sulfinyl, alkoxy, carbamoyl, acylamine, sulfamoyl, sulfonamide, a carbocycle or heterocycle, as defined above; wherein said amino, alkyl, acyl, sulfonyl, sulfinyl, alkoxy, carbamoyl, acylamine, sulfamoyl, sulfonamide, carbocycle and heterocycle substituent is optionally substituted with amino, halogen, hydroxyl, oxo, or is substituted with a carbocycle or heterocycle, as defined above, that is optionally substituted with hydroxyl, amino, halogen, haloalkyl, alkyl, alkoxy or acyl;
$R_2$ is hydrogen;
$R_3$ is Me, F, Cl, —$CH_2$—$SO_2$-Me, —$SO_2$-Me, 1H-1,2,4-triazol-1-yl, 1H-imidazol-1-yl, morpholino, thiomorpholino-methyl with S in the oxidized form $SO_2$, 1,2,3-thiadiazol-4-yl or N-methyl-piperizinyl;
each $R_4$ is independently H or alkyl;
$R_5$ is chloro;
m is 0-3;
n is 0-4;
or a salt or solvate thereof.

7. The method of claim 6, wherein ring B is pyridine.
8. The method of claim 6, wherein $R_1$ is alkyl, haloalkyl, aryl, a heterocycle or a heterocycloalkyl, which is a heterocycle group as defined above covalently bonded to an alkyl group, wherein said aryl, heterocycle and heterocycloalkyl is optionally substituted with hydroxy, halogen, alkyl, alkanoyl or hydroxyalkyl.
9. The method of claim 6, wherein $R_1$ is Me, $CF_3$, Ph, 4-F-phenyl, piperazin-1-yl, 4-methylpiperazin-1-yl, 4-ethylpiperazin-1-yl, 4-acetylpiperazin-1-yl, 3,5-dimethylpiperazin-1-yl, 4-(2-hydroxyethyl)-piperazin-1-yl, (4-methylpiperazin-1-yl)methyl, (4-ethylpiperazin-1-yl)methyl, (4-acetylpiperazin-1-yl)methyl, (3,5-dimethylpiperazin-1-yl)methyl, 4-hydroxypiperidin-1-yl, (piperidin-1-yl)methyl, (1-methylpiperidin-4-ylamino)methyl, morpholino, (3,5-dimethyl)morpholino, morpholinomethyl or 1H-1,2,4-triazol-1-yl.
10. The method of claim 6, wherein both $R_4$ groups are H.
11. A compound of formula II:

II

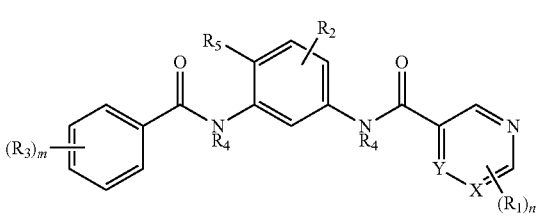

wherein:
X is $CR_1$, or N;
Y is $CR_1$, or N;
$R_1$ is hydroxyl, halogen, amino, nitro, cyano, alkyl, acyl, sulfonyl, sulfinyl, alkoxy, carbamoyl, acylamine, sulfamoyl or sulfonamide; wherein said amino, alkyl, acyl, sulfonyl, sulfinyl, alkoxy, carbamoyl, acylamine, sulfamoyl and sulfonamide substituent is optionally substituted with amino, halogen, hydroxyl, oxo, or is substituted with a carbocycle or heterocycle that is optionally substituted with hydroxyl, amino, halogen, haloalkyl, alkyl, alkoxy or acyl;
or $R_1$ is a carbocycle or a heterocycle that is optionally substituted with hydroxyl, halogen, amino, nitro, cyano, alkyl, acyl, sulfonyl, sulfinyl, alkoxy, carbamoyl, acylamine, sulfamoyl, sulfonamide, a carbocycle or heterocycle; wherein said amino, alkyl, acyl, sulfonyl, sulfinyl, alkoxy, carbamoyl, acylamine, sulfamoyl, sulfonamide, carbocycle and heterocycle substituent is optionally substituted with amino, halogen, hydroxyl, oxo, or is substituted with a carbocycle or heterocycle that is optionally substituted with hydroxyl, amino, halogen, haloalkyl, alkyl, alkoxy or acyl;
carbocycle is a mono-, bi-, or tricyclic aliphatic ring having 3 to 14 carbon atoms which is saturated or unsaturated, aromatic or non-aromatic;
heterocycle is a mono-, bi-, or tricyclic, saturated or unsaturated, aromatic or non-aromatic ring having from 5 to about 14 ring atoms, where the ring atoms are 1 to 4 nitrogen, sulfur or oxygen heteroatoms and the balance carbon atoms;
$R_2$ is hydrogen;
$R_3$ is halogen, hydroxyl, carboxyl, alkyl, acyl, alkoxy, alkoxycarbonyl, carbamoyl, sulfide, sulfinyl, sulfonyl, a carbocycle or a heterocycle, as defined above, wherein each alkyl, acyl, alkoxy, alkoxycarbonyl, carbamoyl, sulfide, sulfinyl, sulfonyl, carbocycle and heterocycle is optionally substituted with hydroxyl, halogen, amino, nitro, alkyl, acyl, sulfonyl or alkoxy;
$R_4$ is H or alkyl;
$R_5$ is chloro;
m is 0-3;
n is 0-4;
or a salt or solvate thereof.

12. A compound selected from the group consisting of:

N-(3-benzamido-4-chlorophenyl)-4-methyl-6-(trifluoromethyl)nicotinamide;
N-(4-chloro-3-(2-chlorobenzamido)phenyl)-2-methyl-6-(trifluoromethyl)-nicotinamide;
N-(4-chloro-3-(3-chlorobenzamido)phenyl)-2-methyl-6-(trifluoromethyl)-nicotinamide;
N-(4-chloro-3-(4-chlorobenzamido)phenyl)-2-methyl-6-(trifluoromethyl)-nicotinamide;
N-(4-chloro-3-(2-fluorobenzamido)phenyl)-2-methyl-6-(trifluoromethyl)-nicotinamide;
N-(4-chloro-3-(3-fluorobenzamido)phenyl)-2-methyl-6-(trifluoromethyl)-nicotinamide;
N-(4-chloro-3-(4-fluorobenzamido)phenyl)-2-methyl-6-(trifluoromethyl)-nicotinamide;
N-(4-chloro-3-(3,4-difluorobenzamido)phenyl)-2-methyl-6-(trifluoromethyl)-nicotinamide;
N-(4-chloro-3-(3-chloro-4-fluorobenzamido)phenyl)-2-methyl-6-(trifluoromethyl)-nicotinamide;
N-(4-chloro-3-(2-morpholinobenzamido)phenyl)-2-methyl-6-(trifluoromethyl)-nicotinamide;
N-(4-chloro-3-(4-(4-methylpiperazin-1-yl)benzamido)phenyl)-2-methyl-6-(trifluoromethyl)nicotinamide;
N-(4-chloro-3-(4-methoxybenzamido)phenyl)-2-methyl-6-(trifluoromethyl)-nicotinamide;
N-(3-(4-(1,2,3-thiadiazol-4-yl)benzamido)-4-chlorophenyl)-2-methyl-6-(trifluoromethyl)nicotinamide;
N-(3-(4-(1H-imidazol-1-yl)benzamido)-4-chlorophenyl)-2-methyl-6-(trifluoromethyl)nicotinamide;
N-(3-(4-(1H-1,2,4-triazol-1-yl)benzamido)-4-chlorophenyl)-2-methyl-6-(trifluoromethyl)nicotinamide;
N-(3-benzamido-4-chlorophenyl)-6-morpholinonicotinamide;
N-(3-benzamido-4-chlorophenyl)-2-methyl-4-phenylpyrimidine-5-carboxamide;
N-(3-benzamido-4-chlorophenyl)-1-(4-fluorophenyl)-4-methyl-1H-pyrazole-3-carboxamide;
N-(3-benzamido-4-chlorophenyl)-4-methyl-2-phenylpyrimidine-5-carboxamide;
N-(3-benzamido-4-chlorophenyl)-6-chloronicotinamide;
N-(3-benzamido-4-chlorophenyl)-6-((3S,5R)-3,5-dimethylpiperazin-1-yl)-nicotinamide;
N-(3-benzamido-4-chlorophenyl)-6-(4-ethylpiperazin-1-yl)nicotinamide;
N-(3-benzamido-4-chlorophenyl)-6-(4-(2-hydroxyethyl)piperazin-1-yl)-nicotinamide;
N-(3-benzamido-4-chlorophenyl)-6-(2,6-dimethylmorpholino)nicotinamide;
6-(4-acetylpiperazin-1-yl)-N-(3-benzamido-4-chlorophenyl)nicotinamide;
N-(3-benzamido-4-chlorophenyl)-6-(4-hydroxypiperidin-1-yl)nicotinamide;
N-(3-benzamido-4-chlorophenyl)-6-(3-methylpiperazin-1-yl)nicotinamide;
(R)—N-(3-benzamido-4-chlorophenyl)-6-(3-methylpiperazin-1-yl)nicotinamide;
(S)—N-(3-benzamido-4-chlorophenyl)-6-(3-methylpiperazin-1-yl)nicotinamide;
N-(3-benzamido-4-chlorophenyl)-6-(piperazin-1-yl)nicotinamide;
N-(3-benzamido-4-chlorophenyl)-6-chloro-2-methylnicotinamide;
N-(3-benzamido-4-chlorophenyl)-6-((3S,5R)-3,5-dimethylpiperazin-1-yl)-2-methyl-nicotinamide;
N-(3-benzamido-4-chlorophenyl)-6-(bromomethyl)nicotinamide;
N-(3-benzamido-4-chlorophenyl)-6-(morpholinomethyl)nicotinamide;
N-(3-benzamido-4-chlorophenyl)-6-(piperidin-1-ylmethyl)nicotinamide;
N-(3-benzamido-4-chlorophenyl)-6-((4-methylpiperazin-1-yl)methyl)nicotinamide;
N-(3-benzamido-4-chlorophenyl)-2-phenylthiazole-4-carboxamide;
6-chloro-N-(4-chloro-3-(4-fluorobenzamido)phenyl)nicotinamide;
N-(4-chloro-3-(4-fluorobenzamido)phenyl)-6-((3S,5R)-3,5-dimethylpiperazin-1-yl)nicotinamide;
N-(4-chloro-3-(4-fluorobenzamido)phenyl)-6-(4-hydroxypiperidin-1-yl)nicotinamide;
6-(4-acetylpiperazin-1-yl)-N-(4-chloro-3-(4-fluorobenzamido)phenyl)nicotinamide;
6-(4-methylsulfonylpiperazin-1-yl-N-(4-chloro-3-(4-fluorobenzamido)phenyl-nicotinamide;
N-(3-(4-fluorobenzamido)-4-chlorophenyl)-6-(4-propionylpiperazin-1-yl)pyridine-3-carboxamide;
6-(4-(3-methylbutanoyl)piperazin-1-yl)-N-(3-(4-fluorobenzamido)-4-chlorophenyl)pyridine-3-carboxamide;
N-(3-(4-fluorobenzamido)-4-chlorophenyl)-6-(4-cyclopropylcarbonylpiperazin-1-yl)pyridine-3-carboxamide;
N-(4-chloro-3-(4-fluorobenzamido)phenyl)-6-(4-ethylpiperazin-1-yl)nicotinamide;
N-(4-chloro-3-(4-fluorobenzamido)phenyl)-6-(piperazin-1-yl)nicotinamide;
N-(4-chloro-3-(4-fluorobenzamido)phenyl)-6-(3-methylpiperazin-1-yl)nicotinamide;
(R)—N-(4-chloro-3-(4-fluorobenzamido)phenyl)-6-(3-methylpiperazin-1-yl)-nicotinamide;
(S)—N-(4-chloro-3-(4-fluorobenzamido)phenyl)-6-(3-methylpiperazin-1-yl)-nicotinamide;
6-chloro-N-(4-chloro-3-(4-fluorobenzamido)phenyl)-2-methylnicotinamide;
N-(4-chloro-3-(4-fluorobenzamido)phenyl)-6-(4-hydroxypiperidin-1-yl)-2-methylnicotinamide;
N-(4-chloro-3-(4-fluorobenzamido)phenyl)-6-(3,5-dimethylpiperazin-1-yl)-2-methylnicotinamide;
6-(4-acetylpiperazin-1-yl)-N-(4-chloro-3-(4-fluorobenzamido)phenyl)-2-methylnicotinamide;
6-chloro-N-(4-chloro-3-(3-chlorobenzamido)phenyl)nicotinamide;
N-(4-chloro-3-(3-chlorobenzamido)phenyl)-6-((3S,5R)-3,5-dimethylpiperazin-1-yl)nicotinamide;
N-(4-chloro-3-(3-chlorobenzamido)phenyl)-6-(4-hydroxypiperidin-1-yl)-nicotinamide;
6-(4-acetylpiperazin-1-yl)-N-(4-chloro-3-(3-chlorobenzamido)phenyl)nicotinamide;
N-(4-chloro-3-(3-chlorobenzamido)phenyl)-6-(4-ethylpiperazin-1-yl)nicotinamide;
N-(4-chloro-3-(3-chlorobenzamido)phenyl)-6-(piperazin-1-yl)nicotinamide;
N-(4-chloro-3-(3-chlorobenzamido)phenyl)-6-(4-(2-hydroxyethyl)piperazin-1-yl)-nicotinamide;
6-(bromomethyl)-N-(4-chloro-3-(3-chlorobenzamido)phenyl)nicotinamide;
N-(4-chloro-3-(3-chlorobenzamido)phenyl)-6-((4-ethylpiperazin-1-yl)methyl)-nicotinamide;
N-(4-chloro-3-(3-chlorobenzamido)phenyl)-6-((4-methylpiperazin-1-yl)methyl)-nicotinamide;
N-(4-chloro-3-(3-chlorobenzamido)phenyl)-6-((1-methylpiperidin-4-ylamino)methyl)nicotinamide;

6-((4-acetylpiperazin-1-yl)methyl)-N-(4-chloro-3-(3-chlorobenzamido)phenyl)-nicotinamide;
N-(4-chloro-3-(3-chlorobenzamido)phenyl)-6-((3S,5R)-3,5-dimethylpiperazin-1-yl)methyl)nicotinamide;
6-chloro-N-(4-chloro-3-(3-chlorobenzamido)phenyl)-2-methylnicotinamide;
N-(4-chloro-3-(3-chlorobenzamido)phenyl)-6-((3S,5R)-3,5-dimethylpiperazin-1-yl)-2-methylnicotinamide;
N-(4-chloro-3-(3-chlorobenzamido)phenyl)-6-(4-hydroxypiperidin-1-yl)-2-methylnicotinamide;
6-chloro-N-(4-chloro-3-(3-chlorobenzamido)phenyl)-2-methylnicotinamide;
N-(4-chloro-3-(3-chlorobenzamido)phenyl)-6-((3S,5R)-3,5-dimethylpiperazin-1-yl)-2-methylnicotinamide;
N-(4-chloro-3-(3-chlorobenzamido)phenyl)-6-(4-hydroxypiperidin-1-yl)-2-methylnicotinamide;
6-(4-acetylpiperazin-1-yl)-N-(4-chloro-3-(3-chlorobenzamido)phenyl)-2-methyl-nicotinamide;
6-(4-acetylpiperazin-1-yl)-N-(4-chloro-3-(2-chlorobenzamido)phenyl)nicotinamide;
6-(4-acetylpiperazin-1-yl)-N-(4-chloro-3-(2-fluorobenzamido)phenyl)nicotinamide;
6-chloro-N-(4-chloro-3-(3-fluorobenzamido)phenyl) nicotinamide;
N-(4-chloro-3-(3-fluorobenzamido)phenyl)-6-((3S,5R)-3,5-dimethylpiperazin-1-yl)-nicotinamide;
N-(4-chloro-3-(3-fluorobenzamido)phenyl)-6-(4-hydroxypiperidin-1-yl)-nicotinamide;
6-(4-acetylpiperazin-1-yl)-N-(4-chloro-3-(3-fluorobenzamido)phenyl)nicotinamide;
6-chloro-N-(4-chloro-3-(2-fluorobenzamido)phenyl) nicotinamide;
N-(4-chloro-3-(2-fluorobenzamido)phenyl)-6-((3S,5R)-3,5-dimethylpiperazin-1-yl)nicotinamide;
N-(4-chloro-3-(2-fluorobenzamido)phenyl)-6-(4-hydroxypiperidin-1-yl)-nicotinamide;
6-chloro-N-(4-chloro-3-(4-chlorobenzamido)phenyl) nicotinamide;
N-(4-chloro-3-(4-chlorobenzamido)phenyl)-6-((3S,5R)-3,5-dimethylpiperazin-1-yl)nicotinamide;
N-(4-chloro-3-(4-chlorobenzamido)phenyl)-6-(4-hydroxypiperidin-1-yl)-nicotinamide;
6-(4-acetylpiperazin-1-yl)-N-(4-chloro-3-(4-chlorobenzamido)phenyl)nicotinamide;
6-chloro-N-(4-chloro-3-(2-chlorobenzamido)phenyl) nicotinamide;
N-(4-chloro-3-(2-chlorobenzamido)phenyl)-6-((3S,5R)-3,5-dimethylpiperazin-1-yl)nicotinamide;
N-(4-chloro-3-(2-chlorobenzamido)phenyl)-6-(4-hydroxypiperidin-1-yl)-nicotinamide;
6-chloro-N-(4-chloro-3-(4-methylbenzamido)phenyl) nicotinamide;
N-(4-chloro-3-(4-methylbenzamido)phenyl)-6-((3S,5R)-3,5-dimethylpiperazin-1-yl)nicotinamide;
N-(4-chloro-3-(4-methylbenzamido)phenyl)-6-(4-hydroxypiperidin-1-yl)-nicotinamide;
6-(4-acetylpiperazin-1-yl)-N-(4-chloro-3-(4-methylbenzamido)phenyl)-nicotinamide;
6-chloro-N-(4-chloro-3-(2-methylbenzamido)phenyl) nicotinamide;
N-(4-chloro-3-(2-methylbenzamido)phenyl)-6-((3S,5R)-3,5-dimethylpiperazin-1-yl)nicotinamide;
N-(4-chloro-3-(2-methylbenzamido)phenyl)-6-(4-hydroxypiperidin-1-yl)-nicotinamide;
6-(4-acetylpiperazin-1-yl)-N-(4-chloro-3-(2-methylbenzamido)phenyl)-nicotinamide;
6-chloro-N-(4-chloro-3-(3-methylbenzamido)phenyl) nicotinamide;
N-(4-chloro-3-(3-methylbenzamido)phenyl)-6-((3S,5R)-3,5-dimethylpiperazin-1-yl)nicotinamide;
N-(4-chloro-3-(3-methylbenzamido)phenyl)-6-(4-hydroxypiperidin-1-yl)-nicotinamide; and
6-(4-acetylpiperazin-1-yl)-N-(4-chloro-3-(3-methylbenzamido)phenyl)-nicotinamide.

13. The method of claim 1, wherein the compound is of the formula II:

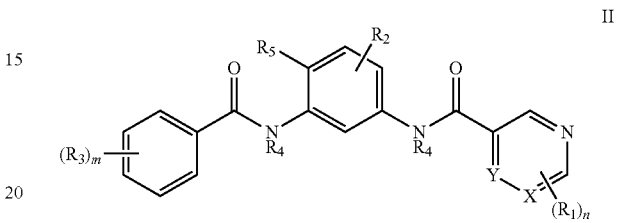

wherein:
X is CR$_1$, or N;
Y is CR$_1$, or N;
R$_1$ is hydroxyl, halogen, amino, nitro, cyano, alkyl, acyl, sulfonyl, sulfinyl, alkoxy, carbamoyl, acylamine, sulfamoyl or sulfonamide; wherein said amino, alkyl, acyl, sulfonyl, sulfinyl, alkoxy, carbamoyl, acylamine, sulfamoyl and sulfonamide substituent is optionally substituted with amino, halogen, hydroxyl, oxo, or is substituted with a carbocycle or heterocycle that is optionally substituted with hydroxyl, amino, halogen, haloalkyl, alkyl, alkoxy or acyl;
or R$_1$ is a carbocycle or a heterocycle that is optionally substituted with hydroxyl, halogen, amino, nitro, cyano, alkyl, acyl, sulfonyl, sulfinyl, alkoxy, carbamoyl, acylamine, sulfamoyl, sulfonamide, a carbocycle or heterocycle; wherein said amino, alkyl, acyl, sulfonyl, sulfinyl, alkoxy, carbamoyl, acylamine, sulfamoyl, sulfonamide, carbocycle and heterocycle substituent is optionally substituted with amino, halogen, hydroxyl, oxo, or is substituted with a carbocycle or heterocycle that is optionally substituted with hydroxyl, amino, halogen, haloalkyl, alkyl, alkoxy or acyl;
wherein carbocycle and heterocycle are as defined above;
R$_2$ is hydrogen;
R$_3$ is Me, F, Cl, —CH$_2$—SO$_2$—Me, —SO$_2$—Me, 1H-1,2,4-triazol-1-yl, 1H-imidazol-1-yl, morpholino, thiomorpholino-methyl with S in the oxidized form SO$_2$, 1,2,3-thiadiazol-4-yl or N-methyl-piperizinyl;
each R$_4$ is independently H or alkyl;
R$_5$ is chloro;
m is 0-3;
n is 0-4;
or a salt or solvate thereof.

14. The method of claim 1, wherein the compound is selected from the group consisting of:
N-(3-benzamido-4-chlorophenyl)-4-methyl-6-(trifluoromethyl)nicotinamide;
N-(4-chloro-3-(2-chlorobenzamido)phenyl)-2-methyl-6-(trifluoromethyl)-nicotinamide;
N-(4-chloro-3-(3-chlorobenzamido)phenyl)-2-methyl-6-(trifluoromethyl)-nicotinamide;

N-(4-chloro-3-(4-chlorobenzamido)phenyl)-2-methyl-6-(trifluoromethyl)-nicotinamide;
N-(4-chloro-3-(2-fluorobenzamido)phenyl)-2-methyl-6-(trifluoromethyl)-nicotinamide;
N-(4-chloro-3-(3-fluorobenzamido)phenyl)-2-methyl-6-(trifluoromethyl)-nicotinamide;
N-(4-chloro-3-(4-fluorobenzamido)phenyl)-2-methyl-6-(trifluoromethyl)-nicotinamide;
N-(4-chloro-3-(3,4-difluorobenzamido)phenyl)-2-methyl-6-(trifluoromethyl)-nicotinamide;
N-(4-chloro-3-(3-chloro-4-fluorobenzamido)phenyl)-2-methyl-6-(trifluoromethyl)-nicotinamide;
N-(4-chloro-3-(2-morpholinobenzamido)phenyl)-2-methyl-6-(trifluoromethyl)-nicotinamide;
N-(4-chloro-3-(4-(4-methylpiperazin-1-yl)benzamido)phenyl)-2-methyl-6-(trifluoromethyl)nicotinamide;
N-(4-chloro-3-(4-methoxybenzamido)phenyl)-2-methyl-6-(trifluoromethyl)-nicotinamide;
N-(3-(4-(1,2,3-thiadiazol-4-yl)benzamido)-4-chlorophenyl)-2-methyl-6-(trifluoromethyl)nicotinamide;
N-(3-(4-(1H-imidazol-1-yl)benzamido)-4-chlorophenyl)-2-methyl-6-(trifluoromethyl)nicotinamide;
N-(3-(4-(1H-1,2,4-triazol-1-yl)benzamido)-4-chlorophenyl)-2-methyl-6-(trifluoromethyl)nicotinamide;
N-(3-benzamido-4-chlorophenyl)-6-morpholinonicotinamide;
N-(3-benzamido-4-chlorophenyl)-2-methyl-4-phenylpyrimidine-5-carboxamide;
N-(3-benzamido-4-chlorophenyl)-1-(4-fluorophenyl)-4-methyl-1H-pyrazole-3-carboxamide;
N-(3-benzamido-4-chlorophenyl)-4-methyl-2-phenylpyrimidine-5-carboxamide;
N-(3-benzamido-4-chlorophenyl)-6-chloronicotinamide;
N-(3-benzamido-4-chlorophenyl)-6-((3S,5R)-3,5-dimethylpiperazin-1-yl)-nicotinamide;
N-(3-benzamido-4-chlorophenyl)-6-(4-ethylpiperazin-1-yl)nicotinamide;
N-(3-benzamido-4-chlorophenyl)-6-(4-(2-hydroxyethyl)piperazin-1-yl)-nicotinamide;
N-(3-benzamido-4-chlorophenyl)-6-(2,6-dimethylmorpholino)nicotinamide;
6-(4-acetylpiperazin-1-yl)-N-(3-benzamido-4-chlorophenyl)nicotinamide;
N-(3-benzamido-4-chlorophenyl)-6-(4-hydroxypiperidin-1-yl)nicotinamide;
N-(3-benzamido-4-chlorophenyl)-6-(3-methylpiperazin-1-yl)nicotinamide;
(R)—N-(3-benzamido-4-chlorophenyl)-6-(3-methylpiperazin-1-yl)nicotinamide;
(S)—N-(3-benzamido-4-chlorophenyl)-6-(3-methylpiperazin-1-yl)nicotinamide;
N-(3-benzamido-4-chlorophenyl)-6-(piperazin-1-yl)nicotinamide;
N-(3-benzamido-4-chlorophenyl)-6-chloro-2-methylnicotinamide;
N-(3-benzamido-4-chlorophenyl)-6-((3S,5R)-3,5-dimethylpiperazin-1-yl)-2-methyl-nicotinamide;
N-(3-benzamido-4-chlorophenyl)-6-(bromomethyl)nicotinamide;
N-(3-benzamido-4-chlorophenyl)-6-(morpholinomethyl)nicotinamide;
N-(3-benzamido-4-chlorophenyl)-6-(piperidin-1-ylmethyl)nicotinamide;
N-(3-benzamido-4-chlorophenyl)-6-((4-methylpiperazin-1-yl)methyl)nicotinamide;
N-(3-benzamido-4-chlorophenyl)-2-phenylthiazole-4-carboxamide;
6-chloro-N-(4-chloro-3-(4-fluorobenzamido)phenyl)nicotinamide;
N-(4-chloro-3-(4-fluorobenzamido)phenyl)-6-((3S,5R)-3,5-dimethylpiperazin-1-yl)nicotinamide;
N-(4-chloro-3-(4-fluorobenzamido)phenyl)-6-(4-hydroxypiperidin-1-yl)nicotinamide;
6-(4-acetylpiperazin-1-yl)-N-(4-chloro-3-(4-fluorobenzamido)phenyl)nicotinamide;
6-(4-methylsulfonylpiperazin-1-yl-N-(4-chloro-3-(4-fluorobenzamido)phenyl-nicotinamide;
N-(3-(4-fluorobenzamido)-4-chlorophenyl)-6-(4-propionylpiperazin-1-yl)pyridine-3-carboxamide;
6-(4-(3-methylbutanoyl)piperazin-1-yl)-N-(3-(4-fluorobenzamido)-4-chlorophenyl)pyridine-3-carboxamide;
N-(3-(4-fluorobenzamido)-4-chlorophenyl)-6-(4-cyclopropylcarbonylpiperazin-1-yl)pyridine-3-carboxamide;
N-(4-chloro-3-(4-fluorobenzamido)phenyl)-6-(4-ethylpiperazin-1-yl)nicotinamide;
N-(4-chloro-3-(4-fluorobenzamido)phenyl)-6-(piperazin-1-yl)nicotinamide;
N-(4-chloro-3-(4-fluorobenzamido)phenyl)-6-(3-methylpiperazin-1-yl)nicotinamide;
(R)—N-(4-chloro-3-(4-fluorobenzamido)phenyl)-6-(3-methylpiperazin-1-yl)-nicotinamide;
(S)—N-(4-chloro-3-(4-fluorobenzamido)phenyl)-6-(3-methylpiperazin-1-yl)-nicotinamide;
6-chloro-N-(4-chloro-3-(4-fluorobenzamido)phenyl)-2-methylnicotinamide;
N-(4-chloro-3-(4-fluorobenzamido)phenyl)-6-(4-hydroxypiperidin-1-yl)-2-methylnicotinamide;
N-(4-chloro-3-(4-fluorobenzamido)phenyl)-6-(3,5-dimethylpiperazin-1-yl)-2-methylnicotinamide;
6-(4-acetylpiperazin-1-yl)-N-(4-chloro-3-(4-fluorobenzamido)phenyl)-2-methylnicotinamide;
6-chloro-N-(4-chloro-3-(3-chlorobenzamido)phenyl)nicotinamide;
N-(4-chloro-3-(3-chlorobenzamido)phenyl)-6-((3S,5R)-3,5-dimethylpiperazin-1-yl)nicotinamide;
N-(4-chloro-3-(3-chlorobenzamido)phenyl)-6-(4-hydroxypiperidin-1-yl)-nicotinamide;
6-(4-acetylpiperazin-1-yl)-N-(4-chloro-3-(3-chlorobenzamido)phenyl)nicotinamide;
N-(4-chloro-3-(3-chlorobenzamido)phenyl)-6-(4-ethylpiperazin-1-yl)nicotinamide;
N-(4-chloro-3-(3-chlorobenzamido)phenyl)-6-(piperazin-1-yl)nicotinamide;
N-(4-chloro-3-(3-chlorobenzamido)phenyl)-6-(4-(2-hydroxyethyl)piperazin-1-yl)-nicotinamide;
6-(bromomethyl)-N-(4-chloro-3-(3-chlorobenzamido)phenyl)nicotinamide;
N-(4-chloro-3-(3-chlorobenzamido)phenyl)-6-((4-ethylpiperazin-1-yl)methyl)-nicotinamide;
N-(4-chloro-3-(3-chlorobenzamido)phenyl)-6-((4-methylpiperazin-1-yl)methyl)-nicotinamide;
N-(4-chloro-3-(3-chlorobenzamido)phenyl)-6-((1-methylpiperidin-4-ylamino)methyl)nicotinamide;
6-((4-acetylpiperazin-1-yl)methyl)-N-(4-chloro-3-(3-chlorobenzamido)phenyl)-nicotinamide;
N-(4-chloro-3-(3-chlorobenzamido)phenyl)-6-((3S,5R)-3,5-dimethylpiperazin-1-yl)methyl)nicotinamide;
6-chloro-N-(4-chloro-3-(3-chlorobenzamido)phenyl)-2-methylnicotinamide;
N-(4-chloro-3-(3-chlorobenzamido)phenyl)-6-((3S,5R)-3,5-dimethylpiperazin-1-yl)-2-methylnicotinamide;

N-(4-chloro-3-(3-chlorobenzamido)phenyl)-6-(4-hydroxypiperidin-1-yl)-2-methylnicotinamide;
6-chloro-N-(4-chloro-3-(3-chlorobenzamido)phenyl)-2-methylnicotinamide;
N-(4-chloro-3-(3-chlorobenzamido)phenyl)-6-((3S,5R)-3,5-dimethylpiperazin-1-yl)-2-methylnicotinamide;
N-(4-chloro-3-(3-chlorobenzamido)phenyl)-6-(4-hydroxypiperidin-1-yl)-2-methylnicotinamide;
6-(4-acetylpiperazin-1-yl)-N-(4-chloro-3-(3-chlorobenzamido)phenyl)-2-methyl-nicotinamide;
6-(4-acetylpiperazin-1-yl)-N-(4-chloro-3-(2-chlorobenzamido)phenyl)nicotinamide;
6-(4-acetylpiperazin-1-yl)-N-(4-chloro-3-(2-fluorobenzamido)phenyl)nicotinamide;
6-chloro-N-(4-chloro-3-(3-fluorobenzamido)phenyl)nicotinamide;
N-(4-chloro-3-(3-fluorobenzamido)phenyl)-6-((3S,5R)-3,5-dimethylpiperazin-1-yl)-nicotinamide;
N-(4-chloro-3-(3-fluorobenzamido)phenyl)-6-(4-hydroxypiperidin-1-yl)-nicotinamide;
6-(4-acetylpiperazin-1-yl)-N-(4-chloro-3-(3-fluorobenzamido)phenyl)nicotinamide;
6-chloro-N-(4-chloro-3-(2-fluorobenzamido)phenyl)nicotinamide;
N-(4-chloro-3-(2-fluorobenzamido)phenyl)-6-((3S,5R)-3,5-dimethylpiperazin-1-yl)nicotinamide;
N-(4-chloro-3-(2-fluorobenzamido)phenyl)-6-(4-hydroxypiperidin-1-yl)-nicotinamide;
6-chloro-N-(4-chloro-3-(4-chlorobenzamido)phenyl)nicotinamide;
N-(4-chloro-3-(4-chlorobenzamido)phenyl)-6-((3S,5R)-3,5-dimethylpiperazin-1-yl)nicotinamide;
N-(4-chloro-3-(4-chlorobenzamido)phenyl)-6-(4-hydroxypiperidin-1-yl)-nicotinamide;
6-(4-acetylpiperazin-1-yl)-N-(4-chloro-3-(4-chlorobenzamido)phenyl)nicotinamide;
6-chloro-N-(4-chloro-3-(2-chlorobenzamido)phenyl)nicotinamide;
N-(4-chloro-3-(2-chlorobenzamido)phenyl)-6-((3S,5R)-3,5-dimethylpiperazin-1-yl)nicotinamide;
N-(4-chloro-3-(2-chlorobenzamido)phenyl)-6-(4-hydroxypiperidin-1-yl)-nicotinamide;
6-chloro-N-(4-chloro-3-(4-methylbenzamido)phenyl)nicotinamide;
N-(4-chloro-3-(4-methylbenzamido)phenyl)-6-((3S,5R)-3,5-dimethylpiperazin-1-yl)nicotinamide;
N-(4-chloro-3-(4-methylbenzamido)phenyl)-6-(4-hydroxypiperidin-1-yl)-nicotinamide;
6-(4-acetylpiperazin-1-yl)-N-(4-chloro-3-(4-methylbenzamido)phenyl)-nicotinamide;
6-chloro-N-(4-chloro-3-(2-methylbenzamido)phenyl)nicotinamide;
N-(4-chloro-3-(2-methylbenzamido)phenyl)-6-((3S,5R)-3,5-dimethylpiperazin-1-yl)nicotinamide;
N-(4-chloro-3-(2-methylbenzamido)phenyl)-6-(4-hydroxypiperidin-1-yl)-nicotinamide;
6-(4-acetylpiperazin-1-yl)-N-(4-chloro-3-(2-methylbenzamido)phenyl)-nicotinamide;
6-chloro-N-(4-chloro-3-(3-methylbenzamido)phenyl)nicotinamide;
N-(4-chloro-3-(3-methylbenzamido)phenyl)-6-((3S,5R)-3,5-dimethylpiperazin-1-yl)nicotinamide;
N-(4-chloro-3-(3-methylbenzamido)phenyl)-6-(4-hydroxypiperidin-1-yl)-nicotinamide; and
6-(4-acetylpiperazin-1-yl)-N-(4-chloro-3-(3-methylbenzamido)phenyl)-nicotinamide.

15. The method of claim 1, wherein $R_3$ is $R_3$ is Me, F, Cl, —$CH_2$—$SO_2$-Me, or —$SO_2$-Me.

16. The method of claim 6, wherein $R_3$ is Me, F, Cl, —$CH_2$—$SO_2$-Me, or —$SO_2$-Me.

17. The method of claim 1, wherein $R_1$ is $CF_3$.

18. The method of claim 6, wherein $R_1$ is $CF_3$.

19. The method of claim 2, wherein $R_1$ is $CF_3$.

20. The method of claim 7, wherein $R_1$ is $CF_3$.

* * * * *